(12) United States Patent
Gil et al.

(10) Patent No.: US 10,654,893 B2
(45) Date of Patent: May 19, 2020

(54) SELF-ASSEMBLING PEPTIDE COMPOSITIONS

(71) Applicant: 3-D MATRIX, LTD., Tokyo (JP)

(72) Inventors: Eun Seok Gil, Acton, MA (US); Karl Gilbert, Danvers, MA (US); Manav Mehta, Brighton, MA (US)

(73) Assignee: 3-D Matrix, Ltd., Tokyo (JP)

( * ) Notice: Subject to any disclaimer, the term of this patent is extended or adjusted under 35 U.S.C. 154(b) by 0 days.

(21) Appl. No.: 15/121,251

(22) PCT Filed: Mar. 10, 2015

(86) PCT No.: PCT/US2015/019796
§ 371 (c)(1),
(2) Date: Aug. 24, 2016

(87) PCT Pub. No.: WO2015/138514
PCT Pub. Date: Sep. 17, 2015

(65) Prior Publication Data
US 2016/0362451 A1    Dec. 15, 2016

Related U.S. Application Data

(60) Provisional application No. 61/950,529, filed on Mar. 10, 2014.

(51) Int. Cl.
| C07K 7/08 | (2006.01) |
| A61L 27/22 | (2006.01) |
| A61L 24/10 | (2006.01) |
| A61K 38/00 | (2006.01) |

(52) U.S. Cl.
CPC .............. C07K 7/08 (2013.01); A61L 24/108 (2013.01); A61L 27/227 (2013.01); A61K 38/00 (2013.01)

(58) Field of Classification Search
None
See application file for complete search history.

(56) References Cited

U.S. PATENT DOCUMENTS

| 4,466,641 A | 8/1984 | Heilman et al. |
| 4,582,640 A | 4/1986 | Smestad et al. |
| 4,642,117 A | 2/1987 | Nguyen et al. |
| 4,947,840 A | 8/1990 | Yannas et al. |
| 5,110,604 A | 5/1992 | Chu et al. |
| 5,126,141 A | 6/1992 | Henry |
| 5,236,903 A | 8/1993 | Saiki et al. |
| 5,292,514 A | 3/1994 | Capecchi et al. |
| 5,510,102 A | 4/1996 | Cochrum |
| 5,527,610 A | 6/1996 | Urry |
| 5,550,187 A | 8/1996 | Rhee et al. |
| 5,670,483 A | 9/1997 | Zhang et al. |
| 5,747,452 A | 5/1998 | Ruoslahti et al. |
| 5,773,577 A | 6/1998 | Cappello |
| 5,955,343 A | 9/1999 | Holmes et al. |
| 6,046,160 A | 4/2000 | Obi-Tabot |
| 6,224,893 B1 | 5/2001 | Langer et al. |
| 6,280,474 B1 | 8/2001 | Cassidy et al. |
| 6,548,630 B1 | 4/2003 | Zhang et al. |
| 6,730,298 B2 | 5/2004 | Griffith-Cima et al. |
| 6,800,481 B1 | 10/2004 | Holmes et al. |
| 7,098,028 B2 | 8/2006 | Holmes et al. |
| 7,449,180 B2 | 11/2008 | Kisiday et al. |
| 7,713,923 B2 | 5/2010 | Genove et al. |
| 7,846,891 B2 | 12/2010 | Ellis-Behnke et al. |
| 8,022,178 B2 | 9/2011 | Horii et al. |
| 9,012,404 B2 | 4/2015 | Spirio et al. |
| 9,084,837 B2 | 7/2015 | Ellis-Behnke et al. |
| 9,162,005 B2 | 10/2015 | Ellis-Behnke et al. |
| 9,327,010 B2 | 5/2016 | Ellis-Behnke et al. |
| 9,339,476 B2 | 5/2016 | Norchi et al. |
| 9,364,513 B2 | 6/2016 | Ellis-Behnke et al. |
| 9,415,084 B2 | 8/2016 | Ellis-Behnke et al. |
| 9,439,941 B2 | 9/2016 | Ellis-Behnke et al. |
| 9,724,448 B2* | 8/2017 | Kobayashi ............ A61L 27/227 |
| 10,245,299 B2 | 4/2019 | Mehta et al. |

(Continued)

FOREIGN PATENT DOCUMENTS

| CA | 2572964 A1 | 2/2006 |
| CA | 2618184 A1 | 12/2006 |

(Continued)

OTHER PUBLICATIONS 2005 memo describing claim interpretation "a" vs "the".*
The University of Waterloo web site for buffers (https://web.archive.org/web/20001213162000/http://www.science.uwaterloo.ca/~cchieh/cact/c123/buffer.htm, available online 2000).*
The Sigma Aldrich catalog page for this compound, https://www.sigmaaldrich.com/catalog/product/sigma/s5761?lang=en&region=US, downloaded Apr. 25, 2018.*
The dokindo catalog page for this product, http://www.dojindo.eu.com/store/p/885-SulfoBiotics-Sodium-sulfide-Na2S.aspx, downloaded Apr. 25, 2018.*
Kyle, Stuart et al, "Recombinant self-assembling peptides as biomaterials for tissue engineering." Biomaterials (2010) 31 p. 9395-9405.*
Cunha, C. et al., 3D culture of adult mouse meural stem cells within functionalized self-assembling peptide scaffolds, International Journal of Nanomedicine, 943-955 (2011).

(Continued)

*Primary Examiner* — Fred H Reynolds
(74) *Attorney, Agent, or Firm* — Choate, Hall & Stewart LLP

(57) ABSTRACT

The present disclosure provides peptide compositions (e.g., of self-assembling peptides) with particular attributes (e.g., peptide identity, peptide concentration, pH, ionic strength [including salt identity and/or concentration], etc. that show particularly useful material properties. The present disclosure also provides technologies for selecting and/or formulating particular peptide compositions useful in specific contexts. In some embodiments, provided peptide compositions have an elevated pH within the range of about 2.5 to about 3.5 and/or an ionic strength that is above that of a corresponding composition of the same peptide, at the same concentration, in water, but is below a critical salt point for the peptide (e.g., so that the composition is not cloudy).

14 Claims, 53 Drawing Sheets

Specification includes a Sequence Listing.

(56) References Cited

U.S. PATENT DOCUMENTS

| | | |
|---|---|---|
| 10,369,237 B2 | 8/2019 | Gil et al. |
| 10,576,123 B2 | 3/2020 | Takamura et al. |
| 2002/0160471 A1 | 10/2002 | Kisiday et al. |
| 2003/0069177 A1 | 4/2003 | Dubaquie et al. |
| 2003/0166846 A1 | 9/2003 | Rothstein et al. |
| 2004/0204561 A1 | 10/2004 | Ellison |
| 2004/0242469 A1 | 12/2004 | Lee et al. |
| 2005/0181973 A1 | 8/2005 | Genove et al. |
| 2005/0287186 A1 | 12/2005 | Ellis-Behnke et al. |
| 2006/0084607 A1 | 4/2006 | Spirio et al. |
| 2006/0148703 A1 | 7/2006 | Lee et al. |
| 2006/0293243 A1 | 12/2006 | Puri et al. |
| 2007/0128175 A1 | 6/2007 | Ozbas et al. |
| 2007/0190603 A1 | 8/2007 | Holmes et al. |
| 2008/0032934 A1 | 2/2008 | Ellis-Behnke et al. |
| 2008/0091233 A1 | 4/2008 | Ellis-Behnke et al. |
| 2009/0053103 A1 | 2/2009 | Mortimer et al. |
| 2009/0111734 A1 | 4/2009 | Ellis-Behnke et al. |
| 2009/0162437 A1 | 6/2009 | Horii et al. |
| 2009/0169598 A1 | 7/2009 | Crutcher |
| 2010/0143504 A1 | 6/2010 | Spirio et al. |
| 2010/0311640 A1 | 12/2010 | Genove et al. |
| 2011/0002880 A1 | 1/2011 | Takamura et al. |
| 2011/0201541 A1* | 8/2011 | Takamura ............... A61K 38/16 514/1.1 |
| 2012/0010140 A1 | 1/2012 | Ellis-Behnke et al. |
| 2012/0058066 A1 | 3/2012 | Nagai et al. |
| 2013/0281547 A1 | 10/2013 | Spirio et al. |
| 2013/0296239 A1 | 11/2013 | Takamura et al. |
| 2014/0038909 A1 | 2/2014 | Takamura et al. |
| 2014/0286888 A1 | 9/2014 | Nagai et al. |
| 2014/0329914 A1 | 11/2014 | Kobayashi et al. |
| 2015/0105336 A1 | 4/2015 | Takamura et al. |
| 2015/0197359 A1 | 7/2015 | Nohara et al. |
| 2015/0258166 A1 | 9/2015 | Spirio et al. |
| 2015/0328279 A1 | 11/2015 | Ellis-Behnke et al. |
| 2016/0000966 A1* | 1/2016 | Kobayashi ............ A61L 31/047 514/13.2 |
| 2016/0015855 A1* | 1/2016 | Nohara ................. A61K 38/00 514/13.5 |
| 2016/0030628 A1 | 2/2016 | Kobayashi |
| 2016/0213906 A1 | 7/2016 | Horita et al. |
| 2016/0287744 A1* | 10/2016 | Kobayashi ............ A61L 31/047 |
| 2016/0317607 A1 | 11/2016 | Spirio et al. |
| 2016/0362451 A1 | 12/2016 | Gil et al. |
| 2017/0072008 A1* | 3/2017 | Mehta .................... A61K 38/10 |
| 2017/0128622 A1* | 5/2017 | Spirio ................... A61L 27/227 |
| 2017/0173105 A1* | 6/2017 | Mehta .................. A61L 26/0047 |
| 2017/0173221 A1* | 6/2017 | Mehta ................... A61L 31/047 |
| 2017/0202986 A1 | 7/2017 | Gil et al. |
| 2018/0369452 A1 | 12/2018 | Maki et al. |
| 2019/0111165 A1 | 4/2019 | Gil et al. |

FOREIGN PATENT DOCUMENTS

| | | |
|---|---|---|
| CN | 101198350 A | 6/2008 |
| CN | 101378773 A | 3/2009 |
| CN | 101514225 A | 8/2009 |
| CN | 103251690 A | 8/2013 |
| EP | 2146667 A2 | 1/2010 |
| EP | 2345433 A1 | 7/2011 |
| EP | 2823830 A1 | 1/2015 |
| EP | 3031466 A1 | 6/2016 |
| JP | 2004-508140 A | 3/2004 |
| JP | 2005-515796 A | 6/2005 |
| JP | 2005-263631 A | 9/2005 |
| JP | 2007-105186 A | 4/2007 |
| JP | 2007-526232 A | 9/2007 |
| JP | 2008-505919 A | 2/2008 |
| JP | 2008-539257 A | 11/2008 |
| JP | 2008-546689 A | 12/2008 |
| JP | 2009-011341 A | 1/2009 |
| JP | 2009-535338 A | 10/2009 |
| JP | 2010-280719 A | 12/2010 |
| JP | 2012-082180 A | 4/2012 |
| JP | 5255274 B2 | 8/2013 |
| JP | 2014-527543 A | 10/2014 |
| JP | 5730828 B2 | 6/2015 |
| JP | 5922749 B2 | 5/2016 |
| WO | WO-94/17811 A1 | 8/1994 |
| WO | WO-1996/040033 A1 | 12/1996 |
| WO | WO-1997/037694 A1 | 10/1997 |
| WO | WO-99/53019 A1 | 10/1999 |
| WO | WO-00/01238 A1 | 1/2000 |
| WO | WO-02/22072 A2 | 3/2002 |
| WO | WO-2002/058749 A2 | 8/2002 |
| WO | WO-2002/062961 A2 | 8/2002 |
| WO | WO-2002/062969 A2 | 8/2002 |
| WO | WO-03/084980 A2 | 10/2003 |
| WO | WO-03/096972 A2 | 11/2003 |
| WO | WO-2004/007532 A2 | 1/2004 |
| WO | WO-2005/001076 A2 | 1/2005 |
| WO | WO-2005/014615 A2 | 2/2005 |
| WO | WO-2005/082399 A2 | 9/2005 |
| WO | WO-2006/014570 A2 | 2/2006 |
| WO | WO-2006/116524 A1 | 11/2006 |
| WO | WO-2006/138023 A1 | 12/2006 |
| WO | WO-2007/076032 A2 | 7/2007 |
| WO | WO-2007/142757 A2 | 12/2007 |
| WO | WO-2008/039483 A2 | 4/2008 |
| WO | WO-2008/073392 A2 | 6/2008 |
| WO | WO-2008/73395 A2 | 6/2008 |
| WO | WO-2008/113030 A2 | 9/2008 |
| WO | WO-2008/127607 A2 | 10/2008 |
| WO | WO-2008/134544 A1 | 11/2008 |
| WO | WO-2009/072556 A1 | 6/2009 |
| WO | WO-2010/017369 A2 | 2/2010 |
| WO | WO-2010/041636 A1 | 4/2010 |
| WO | WO-2010/147763 A2 | 12/2010 |
| WO | WO-2012/008967 A1 | 1/2012 |
| WO | WO-2013/030673 A2 | 3/2013 |
| WO | WO-2013/133413 A1 | 9/2013 |
| WO | WO-2014/008400 A2 | 1/2014 |
| WO | WO-2014/017913 A1 | 1/2014 |
| WO | WO-2014/076660 A1 | 5/2014 |
| WO | WO-2014/136081 A1 | 9/2014 |
| WO | WO-2014/141143 A1 | 9/2014 |
| WO | WO-2014/141160 A1 | 9/2014 |
| WO | WO-2015/027203 A1 | 2/2015 |
| WO | WO-2015/030063 A1 | 3/2015 |
| WO | WO-2015/136370 A2 | 9/2015 |
| WO | WO-2015/138473 A1 | 9/2015 |
| WO | WO-2015/138475 A1 | 9/2015 |
| WO | WO-2015/138478 A1 | 9/2015 |
| WO | WO-2015/138514 A1 | 9/2015 |
| WO | WO-2017/120092 A1 | 7/2017 |

OTHER PUBLICATIONS

International Search Report for PCT/US2015/019738 (Autoassembling Peptides for the Treatment of Pulmonary Leakage, filed Mar. 10, 2015), issued by ISA/EPO, 4 pages (dated Jun. 19, 2015).

International Search Report for PCT/US2015/019740 (Self-Assembling Peptides as Bronchial Obstruction Agents, filed Mar. 10, 2015), issued by ISA/EPO, 5 pages (dated May 26, 2015).

International Search Report for PCT/US2015/019743 (Material for Treating Pulmonary Bulla, filed Mar. 10, 2015), issued by ISA/EPO, 5 pages (dated Jun. 12, 2015).

Moser, C. et al, Autologous fibrin sealant reduces the incidence of prolonged air leak and duration of the chest tube drainage after lung volume reduction surgery: a prospective randomized blinded study, Journal of Thoracic and Cardiovascular Surgery, 136(4): 843-849 (2008).

Week 201413 Thomson Scientific, London, GB; AN 2013-U98585, XP0027 40500, Use of nigella glandulifera freyn 3 seed grass volatile oil for preparing medicine for treating chronic obstructive pulmonary disease, & CN 103 251 690 A People's Liberation Army Xinjiang Milita) Aug. 21, 2013 (Aug. 21, 2013) abstract.

Written Opinion for PCT/US2015/019738 (Autoassembling Peptides for the Treatment of Pulmonary Leakage, Mar. 10, 2015), issued by ISA/EPO, 5 pages (dated Jun. 19, 2015).

(56) References Cited

OTHER PUBLICATIONS

Written Opinion for PCT/US2015/019740 (Self-Assembling Peptides As Bronchial Obstruction Agents, Mar. 10, 2015), issued by ISA/EPO, 5 pages (dated May 26, 2015).
Written Opinion for PCT/US2015/019743 (Material for Treating Pulmonary Bulla, filed Mar. 10, 2015), issued by ISA/EPO, 5 pages (dated Jun. 12, 2015).
Zhou, X-R. et al., Self-assembly of PH and calcium dual-respondive peptide-amphiphillic hydrogel, Journal of Peptide Science, 19: 737-744 (2013).
3-D Matrix Japan, Ltd. Company Profile Power Point, 32 pages, May 2005 (with English translation).
3-D Matrix Japan, Ltd., Products and FAQs, with English Translation, 14 pages. URL: http:/web.archive.org [Retrieved Oct. 21, 2016].
3D Matrix Japan, Company, Technology, Products, Technology, FAQs, Publication, Company, News, Contact, no English translation, 17 pages. URL: http://www.3d-matrix.co.jp/cm02.html [Retrieved Feb. 25, 2005].
3D Matrix Japan, Product Features, with English translation, 2 pages. URL: http://web.archive.org/web/20050416044014/http://www.3d-matrix.eo.jp/pr03.html [Retrieved Feb. 20, 2013].
3D Matrix Japan, Product List, with English translation, 2 pages. URL: http://web.archive.org/web/20050416043834/http://www.3d-matrix.co.jp/pr02.html [Retrieved Aug. 1, 2013].
3D Matrix Japan, Products, with English translation, 2 pages. URL: http://web.archive.org/web/20050415004502/http://www.3d-matrix.eo.jp/pr01.html [Retrieved Feb. 20, 2013].
3D-Matrix Japan, Products, FAQs, 8 pages, dispatched Sep. 20, 2011 [English translation].
BD PuraMatrix Peptide Hydrogel, Catalog No. 354250, BD Biosciences, 1-16 (2004).
Declaration of Dr. Terence Norchi, MD, for use in proceedings against EP 1879606, 4 pages (Mar. 31, 2016).
Declaration of Rutledge Ellis-Behnke for WO 2006/116524, 6 pages, Aug. 10, 2015.
Eisenbud, D. et al, Hydrogel Wound Dressings: Where Do We Stand in 2003?, Ostomy Wound Manage, 49(10): 52-57 (2003).
Ellis-Behnke, R. et al, Crystal clear surgery with self-assembling molecules that act as a barrier in the brain and intestine, Abstracts/Nanomedicine: Nanotechnology, Biology, and Medicine, 1:269-270 (2005).
Ellis-Behnke, R., At the nanoscale: nanohemostat, a new class of hemostatic agent, WIREs Nanomedicine and Nanobiotechnology, 3: 70-78 (2011).
English Translation of Office Action for JP2007-520521 (dated Aug. 24, 2011).
European Search Report for EP 15195734.7, 4 pages (dated Mar. 4, 2016).
Experimental Report conducted at Arch Therapeutics, $(EAKA)_4$ Acetate, 6 pages, (Jul. 2014).
Experimental Report conducted by Ellis-Behnke, 1. Kidneys (rats), received May 12, 2017.
Extended European Search Report for EP 09819170.3, 6 pages (dated Nov. 27, 2013).
Extended European Search Report for EP05770153.4, 7 pages (dated Apr. 7, 2011).
Gervaso, F. et al, The biomaterialist's task: scaffold biomaterials and fabrication technologies, Joints 1(3): 130-137 (2013).
Hilton, J. R. et al, Wound Dressings in Diabetic Foot Disease, Clinical Infectious Diseases, 39: S100-3 (2004).
International Preliminary Report on Patentability, PCT/IB2015/00868, 10 pages, dated Sep. 13, 2016.
International Search Report for PCT/IB2015/000868, 7 pages (dated Dec. 8, 2015).
International Search Report for PCT/JP2009/067367, 2 pages (dated Dec. 15, 2009).
International Search Report for PCT/US2005/024198, 3 pages (dated Feb. 23, 2006).
International Search Report for PCT/US2007/025271, 6 pages (dated Sep. 4, 2008).
Kates, Declaration of Steven Kates, Ph.D., RE: Japanese Patent Application No. 2008-509090 ("Third Party Declaration") (2012).
Komatsu, S. et al, The Neutral Self-Assembling Peptide Hydrogel SPG-178 as a Topical Hemostatic Agent, PLoS ONE, 9(7): e102778 (2014).
Takei, J., 3-Dimensional Cell Culture Scaffold for Everyone: Drug Screening, Tissue Engineering and Cancer Biology, AATEX, 11(3): 170-176 (2006).
Third Party Observation for EP 05770153.4, with exhibits, 71 pages (dated Aug. 25, 2014).
Third Party Observation for JP 2008-509090, 43 pages, references in English (dated Aug. 10, 2011).
Tortora, G. J., Principles of Human Anatomy, Fifth Edition, Chapter 4: The Integumentary System, 98-100 (1989).
Wang. T. et al, Molecular Mechanisms of RAD16-1 Peptide on Fast Stop Bleeding in Rat Models, Int. J. Mol. Sci., 13: 15279-15290 (2012).
Written Opinion for PCT/IB2015/000868, 9 pages (dated Dec. 8, 2015).
Written Opinion for PCT/JP2009/067367, 5 pages (dated Dec. 15, 2009).
Written Opinion for PCT/US2005/024198, 4 pages (dated Feb. 23, 2006).
Zhang, S. et al, PuraMatrix: Self-Assembling Peptide Nanofiber Scaffolds, Scaffolding in Tissue Engineering, Chapter 15, 217-238 (1992).
Zhang, S. et al, Self-assembling peptides in biology, materials science and engineering, Peptide Science—Present and Future, 737-744 (1999).
Zhang, S. et al, Self-complementary oligopeptide matrices support mammalian cell attachment, Biomaterials, 16(18): 1385-1393 (1995).
Abukawa, H. et al, Reconstructing Mandibular Defects Using Autologous Tissue-Engineered Tooth and Bone Constructs, J. Oral Maxillofac. Surg., 67(2):335-347 (2009).
Allen, P. et al, Type I collagen, fibrin and PuraMatrix matrices provide permissive environments for human endothelial and mesenchymal progenitor cells to form neovascular networks, J. Tissue Eng. Regen Med., 5(4):e74-86 (2011).
Altman, M. et al., Conformational behavior of ionic self-complementary peptides, Protein Sci., 9(6):1095-105 (2000).
Anderson, I. The properties of hyaluronan and its role in wound healing, Prof. Nurse., 17(4):232-5 (2001).
Author Not Known, Medical Devices: Guidance Document, Borderline products, drug-delivery products and medical devices incorporating, as an integral part, an ancillary medicinal substance or an ancillary human blood derivative, European Commission, DG Enterprise and Industry, Directorate F, Unit F3 "Cosmetics and medical devices", 22 pages (Dec. 3, 2009) <http://ec.europa.eu/health/medical-devices/files/meddev/2_1_3_rev_3-12_2009_en.pdf> [last accessed on May 4, 2015].
Bouten, C.V. et al, Substrates for cardiovascular tissue engineering, Adv. Drug Deliv. Rev., 63(4-5):221-41 (2011).
Branco, M.G. and Schneider, J.P., Self-assembling materials for therapeutic delivery, Acta. Biomaterialia, 5(3): 817-831 (2009).
Caplan, M.R. et al., Control of self-assembling oligopeptide matrix formation through systematic variation of amino acid sequence, Biomaterials, 23(1):219-27 (2002).
Caplan, M.R. et al., Effects of systematic variation of amino acid sequence on the mechanical properties of a self-assembling, oligopeptide biomaterial, J. Biomater. Sci. Polymer Edn., 13(3):225-236 (2002).
Caplan, M.R. et al., Self-assembly of a beta-sheet protein governed by relief of electrostatic repulsion relative to van der Waals attraction, Biomacromolecules, 1(4):627-31 (2000).
Censi, R. et al, Hydrogels for protein delivery in tissue engineering, J. Control Release, 161(2):680-692 (2012).
Chen, K. et al, A Hybrid Silk/RADA-Based Fibrous Scaffold with Triple Hierarchy for Ligament Regeneration, Tissue Eng. Part A., 18(13-14):1399-409 (2012).
Chen, P., Self-assembly of ionic-complementary peptides: a physicochemical viewpoint, Colloids and Surfaces A: Physicochemical and Engineering Aspects, 261(1-3): 3-24 (2005).

(56) References Cited

OTHER PUBLICATIONS

Cigognini, D. et al, Evaluation of early and late effects into the acute spinal cord injury of an injectable functionalized self-assembling scaffold, PLoS One., 6(5): e19782 (2011).

Concaro, S. et al, Effect of different materials on the proliferation and migration of articular chondrocytes, Osteoarthritis and Cartilage, 15:Supplement B, pp. B119 (2007).

Cooper et al., "Testing the "critical-size" in calvarial bone defects: revisiting the concept of a critical-sized defect (CSD)," Plast Reconstr Surg. 125(6): 1685-1692, 2010.

Cunha, C. et al, Emerging nanotechnology approaches in tissue engineering for peripheral nerve regeneration, Nanomedicine, 7(1):50-59 (2011).

Curley, J.L. et al, Fabrication of micropatterned hydrogels for neural culture systems using dynamic mask projection photolithography, J. Vis. Exp., 48: 2636 (2011).

Davis, M.E. et al, Custom design of the cardiac microenvironment with biomaterials, Circ Res., 97(1):8-15 (2005).

Davis, M.E. et al, Injectable self-assembling peptide nanofibers create intramyocardial microenvironments for endothelial cells, Circulation, 111(4):442-450 (2005).

Davis, M.E. et al, Local myocardial insulin-like growth factor 1 (IGF-1) delivery with biotinylated peptide nanofibers improves cell therapy for myocardial infarction, Proc. Natl. Acad. Sci. USA. ,103(21):8155-8160 (2006).

Dutta, R.C. and Dutta, A.K., Comprehension of ECM-Cell dynamics: A prerequisite for tissue regeneration, Biotechnol. Adv., 28(6):764-769 (2010).

Dégano, I.R. et al, The effect of self-assembling peptide nanofiber scaffolds on mouse embryonic fibroblast implantation and proliferation, Biomaterials, 30(6):1156-65 (2009).

Ellis-Behnke, R.G. et al, Nano neuro knitting: peptide nanofiber scaffold for brain repair and axon regeneration with functional return of vision, Proc. Natl. Acad. Sci. USA, 103(13):5054-5059 (2006).

Ellis-Behnke, R.G. et al., Nano hemostat solution: immediate hemostasis at the nanoscale, Nanomedicine, (4):207-215 (2006).

Garreta, E. et al, Osteogenic differentiation of mouse embryonic stem cells and mouse embryonic fibroblasts in a three-dimensional self-assembling peptide scaffold, Tissue Eng., 12(8):2215-27 (2006).

Gelain, F. et al, Slow and sustained release of active cytokines from self-assembling peptide scaffolds, J. Control Release, 145(3):231-239 (2010).

Gelain, F. et al., Designer self-assembling peptide scaffolds for 3-d tissue cell cultures and regenerative medicine, Macromol. Biosci. 7(5):544-551 (2007).

Gherli, T. et al., Comparing warfarin with aspirin after biological aortic valve replacement: a prospective study, Circulation, 110(5):496-500 (2004).

Giri, S. and Bader, A., Improved preclinical safety assessment using micro-BAL devices: The potential impact on human discovery and drug attrition, Drug Discov. Today, 16(9-10):382-397 (2011).

Gonzales, A.L. et al., Integrin interactions with immobilized peptides in polyethylene glycol diacrylate hydrogels, Tissue Eng., 10(11-12):1775-86 (2004).

Guo, H.D. et al, Sustained delivery of VEGF from designer self-assembling peptides improves cardiac function after myocardial infarction, Biochem. Biophys. Res. Commun., 424(1):105-111 (2012).

Guo, H.D. et al, Transplantation of marrow-derived cardiac stem cells carried in designer self-assembling peptide nanofibers improves cardiac function after myocardial infarction, Biochem. Biophys. Res. Commun., 399(1):42-48 (2010).

Guo, J. et al, Reknitting the injured spinal cord by self-assembling peptide nanofiber scaffold, Nanomedicine, 3(4):311-321 (2007).

Gurski, L.A. et al, 3D Matrices for Anti-Cancer Drug Testing and Development, Oncology, Issues Jan./Feb. 2010: 20-25.

Hartgerink, J.D. et al., Peptide-amphiphile nanofibers: a versatile scaffold for the preparation of self-assembling materials, Proc. Natl. Acad. Sci. U S A., 99(8):5133-8 (2002).

Hemmrich, K. et al., Implantation of preadipocyte-loaded hyaluronic acid-based scaffolds into nude mice to evaluate potential for soft tissue engineering, Biomaterials, 26(34):7025-37 (2005).

Henriksson, H. et al, Investigation of different cell types and gel carriers for cell-based intervertebral disc therapy, in vitro and in vivo studies, J. Tissue Eng. Regen. Med., doi: 10.1002/term.480 (2011).

Henriksson, H.B. et al, Transplantation of human mesenchymal stems cells into intervertebral discs in a senogeneic porcine model, Spine (Phila Pa 1976), 34(2):141-148 (2009).

Hollinger, J.O. and Kleinschmidt, J.C., The critical size defect as an experimental model to test bone repair materials, J. Craniofac Surg 1990(1): 60-68.

Holmes, T.C. et al., Extensive neurite outgrowth and active synapse formation on self-assembling peptide scaffolds, Proc. Natl. Acad. Sci. U S A., 97(12):6728-33 (2000).

Horii, A. et al, Biological designer self-assembling peptide nanofiber scaffolds significantly enhance osteoblast proliferation, differentiation and 3-D migration, PLoS One, 2(2):e190 (2007).

Hsieh, P.C. et al, Controlled delivery of PDGF-BB for myocardial protection using injectable self-assembling peptide nanofibers, J. Clin. Invest.,116(1):237-248 (2006).

Hsieh, P.C.H. et al, Local controlled intramyocardial delivery of platelet-derived growth factor improves postinfarction ventricular function without pulmonary toxicity, Circulation, 114(7):637-644 (2006).

Huang, A.H. et al, Mechanics and mechanobiology of mesenchymal stem cell-based engineered cartilage, J. Biomech., 43(1):128-136 (2010).

Hwang, W. et al., Supramolecular structure of helical ribbons self-assembled from a beta-sheet peptide, The Journal of Chemical Physics, 118(1): 389-397 (2003).

International Search Report on Patentability for PCT/US2015/019796, 6 pages, dated Sep. 13, 2016.

Kim, J.H. et al, The enhancement of mature vessel formation and cardiac function in infarcted hearts using dual growth factor delivery with self-assembling peptides, Biomaterials, 32(26):6080-6088 (2011).

Kisiday, J. et al, Self-assembling peptide hydrogel fosters chondrocyte extracellular matrix production and cell division: implications for cartilage tissue repair, Proc. Natl. Acad. Sci. USA, 99(15):9996-10001 (2002).

Kohgo, T. et al, Poster 110: Bone Regeneration for Dental Implants Using Tissue-Engineered Bone With Self-Assembling Peptide Nanofiber 3-Dimensional (3D) Scaffolds, Journal of Oral and Maxillofacial Surgery, 65(9): Supplement, p. 43.e63 (2007).

Kopecek, J. and Yang, J., Peptide-directed self-assembly of hydrogels, Acta Biomaterialia, 5(3): 805-816 (2009).

Kumada, Y. and Zhang, S., Significant type I and type III collagen production from human periodontal ligament fibroblasts in 3D peptide scaffolds without extra growth factors, PLoS One, 5(4):e10305 (2010).

Kumada, Y. et al., Functionalized scaffolds of shorter self-assembling peptides containing MMP-2 cleavable motif promote fibroblast proliferation and significantly accelerate 3-D cell migration independent of scaffold stiffness, Soft Matter, The Royal Society of Chemistry, 7 pages (2010).

Kyle, S. et al., Production of self-assembling biomaterials for tissue engineering, Trends Biotechnol., 27(7):423-33 (2009).

Lampe, K.J. and Heilshorn, S.C., Building stem cell niches from the molecule up through engineered peptide materials, Neurosci. Lett., 519(2):138-46 (2012).

Lee, J. et al., Three-dimensional cell culture matrices: state of the art, Tissue Eng. Part B Rev., 14(1):61-86 (2008).

Leon, E.J. et al., Mechanical properties of a self-assembling oligopeptide matrix, J. Biomater. Sci. Polymer Edn., 9(3):297-312 (1998).

Leung, G.K. et al, Peptide nanofiber scaffold for brain tissue reconstruction, Methods Enzymol., 508:177-190 (2012).

Li, X. et al, Engineering neural stem cell fates with hydrogel design for central nervous system regeneration, Progress in Polymer Science, 37(8):1105-1129 (2012).

(56) References Cited

OTHER PUBLICATIONS

Liedmann, A. et al, Cultivation of human neural progenitor cells in a 3-dimensional self-assembling peptide hydrogel, J. Vis. Exp., (59):e3830 (2012).
Liu, J. et al, Controlled release of paclitaxel from a self-assembling peptide hydrogel formed in situ and antitumor study in vitro, Int. J. Nanomedicine, 6:2143-53 (2011).
Liu, W-M. et al., Diversification of Microfluidic Chip for Applications in Cell-Based Bioanalysis, Chinese Journal of Analytical Chemistry, 40(1): 24-31 (2012).
Loo, Y. et al., From short peptides to nanofibers to macromolecular assemblies in biomedicine, Biotechnol. Adv., 30(3):593-603 (2012).
Luo, Z. and Zhang, S., Designer nanomaterials using chiral self-assembling peptide systems and their emerging benefit for society, Chem. Soc. Rev., 41(13):4736-54 (2012).
Luo, Z. et al, Fabrication of self-assembling d-form peptide nanofiber scaffold d-EAK16 for rapid hemostasis, Biomaterials, 32(8):2013-20 (2011).
Maher, S.A. et al, A nano-fibrous cell-seeded hydrogel promotes integration in a cartilage gap model, J. Tissue Eng. Regen. Med., 4(1):25-29 (2010).
Marini, D.M. et al., Left-Handed Helical Ribbon Intermediates in the Self-Assembly of a beta-Sheet Peptide, Nano Letters, 2(4):295-299 (2002).
Marston, W.A. et al., Initial report of the use of an injectable porcine collagen-derived matrix to stimulate healing of diabetic foot wounds in humans, Wound Repair Regen., 13(3):243-7 (2005).
Masuhara, H. et al, Novel infectious agent-free hemostatic material (TDM-621) in cardiovascular surgery, Ann. Thorac. Cardiovasc. Surg. Methods Enzymol., 18(5):444-451 (2012).
McGrath, A.M. et al, BD © PuraMatrix® peptide hydrogel seeded with Schwann cells for peripheral nerve regeneration, Brain Res. Bull., 83(5):207-213 (2010).
Meng, H. et al, Peripferal Nerve Regeneration in Response to Synthesized Nanofiber Scaffold Hydrogel, Life Science Journal, 9(1): 42-46 (2012).
Misawa, H. et al, PuraMatrix facilitates bone regeneration in bone defects of calvaria in mice, Cell Transplant, 15(10):903-910 (2006).
Mooney, M.P. and Siegel, M.I., Animal models for bone tissue engineering of critical-sized defects (CSDs), bone pathologies, and orthopedic disease states, In: Hollinger, JO.; Einhorn, TA.; Doll, BA.; Sfeir, C.,editors. Bone Tissue Engineering. Boca Raton, FL: C.R.C. Press, pp. 217-244 (2005).
Nakahara, H. et al, Bone repair using a hybrid scaffold of self-assembling peptide PuraMatrix and polyetheretherketone cage in rats, Cell Transplant, 19(6):791-797 (2010).
Narmoneva, D.A. et al, Endothelial cells promote cardiac myocyte survival and spatial reorganization: implications for cardiac regeneration, Circulation, 110(8):962-968 (2004).
Narmoneva, D.A. et al., Self-assembling short oligopeptides and the promotion of angiogenesis, Biomaterials, 26(23):4837-46 (2005).
Nichol, J.W. et al, Co-culture induces alignment in engineered cardiac constructs via MMP-2 expression, Biochem. Biophys. Res. Commun., 373(3):360-365 (2008).
Nishimura, A. et al, Controlled release of insulin from self-assembling nanofiber hydrogel, PuraMatrix®: application for the subcutaneous injection in rats, Eur. J. Pharm. Sci., 45(1-2):1-7 (2012).
Ortinau, S. et al, Effect of 3D-scaffold formation on differentiation and survival in human neural progenitor cells, Biomed. Eng. Online, 9(1):70 (2010).
Osterman, D.G. and Kaiser, E.T., Design and characterization of peptides with amphiphilic beta-strand structures, J. Cell Biochem., 29(2):57-72 (1985).
Patterson, J. et al., Biomimetic materials in tissue engineering, Materialstoday, 13(1-2):14-22 (2010).
Saiga, K. et al, Combined use of bFGF and GDF-5 enhances the healing of medial collateral ligament injury, Biochem. Biophys. Res. Commun., 402(2):329-334 (2010).

Sanborn, T.J. et al., A Thermally Triggered, Enzymatically Cross-linked PEG-Peptide Hydrogel for Biomaterial Applications, Presented at 2001 Annual Meeting, Americal Institute of Chemical Engineers, Reno, NV, Nov. 4-9, 2001.
Scalfani, A.P. and Romo III., T., Injectable fillers for facial soft tissue enhancement, Facial Plast. Surg., 16(1):29-34 (2000).
Segers, V.F. and Lee, R.T., Local delivery of proteins and the use of self-assembling peptides, Drug Discov. Today, 12(13-14):561-8 (2007).
Segers, V.F.M. and Lee, R.T., Stem-cell therapy for cardiac disease, Nature 451, 937-942 (2008).
Segers, V.F.M. et al, Local delivery of protease-resistant stromal cell derived factor-1 for stem cell recruitment after myocardial infarction, Circulation, 116(15):1683-1692 (2007).
Semino, C.E. et al., Entrapment of migrating hippocampal neural cells in three-dimensional peptide nanofiber scaffold, Tissue Eng., 10(3-4):643-55 (2004).
Semino, C.E., Self-assembling peptides: from bio-inspired materials to bone regeneration, J. Dent Res., 87(7):606-616 (2008).
Serban, M.A. et al, Effects of extracellular matrix analogues on primary human fibroblast behavior, Acta Biomater., 4(1):67-75 (2008).
Shirai, K. et al, Multipotency of clonal cells derived from swine periodontal ligament and differential regulation by fibroblast growth factor and bone morphogenetic protein, J. Periodontal Res., 44(2):238-247 (2009).
Shivachar, A.C., Isolation and Culturing of Glial, Neuronal and Neural Stem Cell Types Encapsulated in Biodegradable Peptide Hydrogel, Topics in Tissue Engineering, vol. 4. Eds. N Ashammakhi, R Reis, & F Chiellini © 2008.
Song, H. et al, Hemostatic efficacy of biological self-assembling peptide nanofibers in a rat kidney model, Macromol Biosci., 10(1):33-39 (2010).
Spencer, N.J. et al, Peptide- and collagen-based hydrogel substrates for in vitro culture of chick cochleae, Biomaterials, 29(8):1028-1042 (2008).
Sur, S. et al, A hybrid nanofiber matrix to control the survival and maturation of brain neurons, Biomaterials, 33(2):545-55 (2012).
Thonhoff, J.R. et al, Compatibility of human fetal neural stem cells with hydrogel biomaterials in vitro, Brain Res., 1187:42-51 (2008).
Tokunaga, M. et al, Implantation of cardiac progenitor cells using self-assembling peptide improves cardiac function after myocardial infarction, J. Mol. Cell. Cardiol., 49(6):972-983 (2010).
Tokunou, T. et al, Engineering insulin-like growth factor-1 for local delivery, FASEB J., 22(6):1886-1893 (2008).
Uemura, M. et al, Matrigel supports survival and neuronal differentiation of grafted embryonic stem cell-derived neural precursor cells, J. Neurosci. Res., 88(3):542-551 (2010).
Van Putten, S.M. et al, The downmodulation of the foreign body reaction by cytomegalovirus encoded interleukin-10, Biomaterials, 30(5):730-735 (2008).
Wang, Q.G. et al, The composition of hydrogels for cartilage tissue engineering can influence glycosaminoglycan profile, Eur. Cell Mater, 19:86-95 (2010).
Yamaoka, H. et al, Cartilage tissue engineering using human auricular chondrocytes embedded in different hydrogel materials, J. Biomed. Mater Res. A., 78(1):1-11 (2006).
Ye, Z. et al, Temperature and pH effects on biophysical and morphological properties of self-assembling peptide RADA16-I., J. Pept. Sci.,14(2):152-162 (2008).
Yla-Outinen, L. et al, Three-dimensional growth matrix for human embryonic stem cell-derived neuronal cells, J. Tissue Eng. Regen. Med., doi: 10.1002/term.1512 (2012).
Yokoi, H. et al., Dynamic reassembly of peptide RADA16 nanofiber scaffold, Proc. Natl. Acad. Sci. U S A, 102(24):8414-9 (2005).
Yoshimi, R. et al, Self-assembling peptide nanofiber scaffolds, platelet-rich plasma, and mesenchymal stem cells for injectable bone regeneration with tissue engineering, J. Craniofac. Surg., 20(5):1523-1530 (2009).
Yu, Y.C. et al., Construction of biologically active protein molecular architecture using self-assembling peptide-amphiphiles, Methods Enzymol., 289:571-87 (1997).

(56) References Cited

OTHER PUBLICATIONS

Zarzhitsky, S. and Rapaport, H., The interactions between doxorubicin and amphiphilic and acidic β-sheet peptides towards drug delivery hydrogels, J. Colloid Interface Sci. 360(2):525-531 (2011).
Zhang, S. et al., Building from the bottom up, Materials Today, 20-27 (2003).
Zhang, S. Self-assembling peptide materials, Amino Acids, Pept. Proteins, 37:40-65 (2012).
Zhang, S., Beyond the Petri dish, Nat. Biotechnol., 22(2):151-2 (2004).
Zhang, S., Designer Self-Assembling Peptide Nanofiber Scaffolds for Study of 3-D Cell Biology and Beyond, Cancer Research, 335-362 (2008).
Zhang, S., Emerging biological materials through molecular self-assembly, Biotechnol. Adv., 20(5-6):321-39 (2002).
Zhang, S., Fabrication of novel biomaterials through molecular self-assembly, Nat. Biotechnol., 21(10):1171-8 (2003).
Zhang, S., Hydrogels: Wet or let die, Nat. Mater., 3(1):7-8 (2004).
Zhao, X. et al., Recent development of peptide self-assembly, Progress in Natural Science 18, 6(10):653-660 (2008).
Zhaoyang, Y. et al., Temperature and pH effects on biophysical and morphological properties of self-assembling peptide RADA16-T, Journal of Peptide Science, 14(2):152-162 (2008).
BD PuraMatrix Peptide Hydrogel, Product Specification Sheet, 1 page (2004).
Chemical Abstracts Service, Columbus, Ohio, US; Jin, Meng-Zhe et al, Impacts of ligustrazine combined with ICS\LABA on inflammation of lung tissues in rats with chronic obstructive pulmonary disease, XP002740499, retrieved from STN Database accession No. 161:239385 abstract & Jin, Ming-Zhe et al.: "Impacts of ligustrazine combined with ICS/LABA on inflammation of lung tissues in rats with chronic obstructive pulmonary disease", Shiyong Yixue Zazhi, 29(16), 2621-2623 CODEN: SYZAFM, ISSN. entered STN 2014.
European Exam Report for EP15712233.4, 4 pages (dated Jul. 13, 2017).
Boyle, A. L., Applications of de novo designed peptides, Peptide Applications in Biomedicine, Biotechnology and Bioengineering, 51-86 (2017).
Criner, G. J. et al, Biologic Lung Volume Reduction in Advanced Upper Lobe Emphysema Phase 2 Results, Am. J. Respir. Crit. Care Med., 179: 791-798 (2009).
Ingenito, E. P. et al, Bronchoscopic Lung Volume Reduction in Severe Emphysema, Proc. Am. Thorac Soc., 5(4): 454-460 (2008).
Olson, E. J., Hyperinflated Lungs: What does it mean?, A recent chest X-ray showed that I have hyperinflated lungs. What could cause this?, Mayo Clinic, Nov. 30, 2017, retrieved from <<https://www.mayoclinic.org/diseases-conditions/emphysema/expert-answers/hyperinflated-lungs/faq-20058169>>, 3 pages, accessed Feb. 14, 2019.
PuraStat® Synthetic Surgical Hemostatic Agent, Product Information, Nanotechnology Products Database, registration date Mar. 30, 2017, retrieved from <https://product.statnano.com/product/8558> accessed on Oct. 11, 2019.
Aguado, B. A. et al., Improving Viability of Stem Cells During Syringe Needle Flow Through the Design of Hydrogel Cell Carriers, Tissue Eng Part A., 18(7-8): 806-815. (2012).
Anderson, J. M. et al., Modulating the Gelation Properties of Self-Assembling Peptide Amphiphiles, ACS Nano., 3(11): 3447-3454 (2009).
Hsu, B. B. et al, Clotting Mimicry from Robust Hemostatic Bandages Based on Self-Assembling Peptides, ACS Nano, 9(9): 9394-9406 (2015).
Meng, H. et al, The effect of a self-assembling peptide nanofiber scaffold (peptide) when used as a wound dressing for the treatment of deep second degree burns in rats, J. Biomed. Mater Res. B. Appl. Biomater., 89(2): 379-91 (2009).
Paradís-Bas, M. et al, RADA-16: A Tough Peptide—Strategies for Synthesis and Purification, Eur. J. Org. Chem., 5871-5878 (2013).
Taghavi, L, et al, Evaluation of the hemocompatability of RADA 16-1 peptide, J. Biomat. App.. 32(8): 1024-1031 (2018).

Xu, F. F. et al, Comparison between self-assembling peptide nanofiber scaffold (SAPNS) and fibrin sealant in neurosurgical hemostasis, Clin. Transl. Sci., 8(5): 490-4 (2015).
[No Author Listed] Fluid. Iwanami Rikagaku Dictionary, 3rd edition Incremental version, 2nd Print, Oct. 20, 1981, p. 1430, Partial English Translation, 1 Page.
Akers, M. J., Chapter 26: Parenteral Preparations, Remington: Essentials of Pharmaceutics, Edited by Linda Felton, Pharmaceutical Press, p. 497 (2012).
Arista™ Information Sheet, Medafor, Inc., 6 pages (2006).
Arosio, P. et al, End-to-end self-assembly of RADA 16-I nanofibrils in aqueous solutions, Biophys. J., 102(7): 1617-26 (2012).
Author Unknown, Acrodisc® Syringe Filter with Supor® Membrane −0.2 μm, 13mm (1000/pkg), Product ID: 4692, Pall Shop, accessed from <<https://shop.pall.com/us/en/laboratory/sterile-filtration-and-clarification/mycoplasma-reduction/acrodisc-syringe-filters-with-supor-membrane-zid4692>> (2019).
Author Unknown, AORNs Recommended Practices for Maintaining a Sterile Field is Up for Review and Public Comment Through Mar. 25, 2005, retrieved from <<https://www.infectioncontroltoday.com/guidelines/aorns-recommended-practices-maintaining-sterile-field-review-and-public-comment-through>>, accessed on Dec. 19, 2018 (23 pages).
Author Unknown, ISO 13485, Wikipedia, retrieved from <<https://en.wikipedia.org/w/index.php?title=IS0 13485&oldid=694123721>>. Accessed on Dec. 2, 2016.
Author Unknown, Medical Device, Wikipedia, retrieved from <<https://en.wikipedia.org/w/index.php?title=Medical_device&oldid=699710004>>, retrieved on Dec. 2, 2016.
Basford, P.J., et al., Endoscopic resection of sporadic duodenal adenomas: comparison of endoscopic mucosal resection (EMR) with hybrid endoscopic submucosal dissection (ESD) techniques and the risks of late delayed bleeding, Surg. Endosc., 28: 1594-1600 (2014).
Baumfalk and Finazzo, Filter Integrity testing helps to ensure that GMP sterility requirements are met, BioPharm International, 19(6): 1-3 (2006).
Beam, J., Wound Cleansing: Water or Saline?, Journal of Athletic Training, 41(2): 196-197 (2006).
Becton, Dickinson and Company, Positively Unique: BD PosiFlush™ Pre-Filled Syringes, Brochure, 6 pages (Jun. 2010).
Cai, L. et al, Injectable Hydrogels with In Situ Double Network Formation Enhance Retention of Transplanted Stem Cells, Adv. Funct. Mater., 1-8 (2015).
CoSeal® Surgical Sealant, Information Sheet, Baxter Healthcare Corporation, 8 pages (2006).
CryoLife®, Life Restoring Technologies, BioGlue® Instructions for Use: Surgical Adhesive Syringe Instructions for Use, L6312.008—(Apr. 2014), pp. 1-15, 16 pages (2014).
CyroLife: BioGlue® Surgical Adhesive, Products & Services, Website ©2007-2012,<http://web.archive.org/web/20120226221438/http://cryolife.com/products/bioglue-surgical-adhesive>, Retrieved Sep. 1, 2017.
Driscoll, P., What are the differences and similarities between laparoscopy and endoscopy?, 1 page (2016), <https//www.quora.com/what-are-the-differences-and-similiarities-between-laparoscopy-and-endoscopy> Retrieved on Oct. 4, 2017.
Ginsberg, M., Good Medicine/Bad Medicine and the Law of Evidence: Is There a Role for Proof of Character, Propensity, or Prior Bad Conduct in Medical Negligence Litigation?, South Caroline Law Review, 63:367-402 (2011).
Hielscher Ultrasound Technology, 2008, Ultrasonic Degassing and Defoaming of Liquids, accessed from https://www.hielscher.com/degassing_01.htm, on Mar. 27, 2019.
Hirai, K. et al, The fundamental study of Matrigel (PuraMatrix TM) for the hemostasis of bleeding from pulmonary artery and vein or the prevention of lung fistel, Gen Thorac Cardiovasc Surg, 59 (Supplement): 600 (2011).
InjectorForce Max™, Olympus, Brochure, 3 pages (2012).
Koh, R., et al. Antithrombotic drugs are risk factors for delayed postoperative bleeding after endoscopic submucosal dissection for gastric neoplasms, Gastrointest. Endosc., 78: 476-483 (2013).

(56) References Cited

OTHER PUBLICATIONS

Kubba, A.K. and Palmer, K. R., Role of endoscopic injection therapy in the treatment of bleeding peptic ulcer, British Journal of Surgery, 83: 461-468 (1996).

Lin, H-J. et al, A prospective, randomized trial of large-versus small-volume endoscopic injection of epinephrine for peptic ulcer bleeding, Gastrointestinal Endoscopy, 55(6): 615-619 (2002).

Louie, M. K. et al, Bovine Serum Albumin Glutaraldehyde for Completely Sutureless Laparoscopic Heminephrectomy in a Survival Porcine Model, Journal of Endourology, 24(3): 451-455 (2010).

Lépilliez, V., et al., Endoscopic resection of sporadic duodenal adenomas: an efficient technique with a substantial risk of delayed bleeding, Endoscopy, 40: 806-810 (2008).

McFadden, P. M., Minimally Invasive Thoracic Surgery, vol. 2, No. 3, Jul. 2000, pp. 137-144.

Mimotopes, A Guide to Handling and Storing Peptides, PU3-004-1, Feb. 20, 2011, Date established via internet achieve http://www.mimotopes.com/files/editor_upload/File/PeptidesAndAntibodies/PU3004- 1Handling-and-Storing-Peptides.PDF.

Ono, S. et al., Thienopyridine derivatives as risk factors for bleeding following high risk endoscopic treatments: Safe Treatment on Antiplatelets (STRAP) study, Endoscopy, 47: 632-637 (2015).

Paramasivam, E., Air leaks, pneumothorax, and chest drains, Continuing Education in Anesthesia, Critical Care & Pain, vol. 8 No. 6 2008.

Pioche, M. et al, A self-assembling matrix-forming gel can be easily and safely applied to prevent delayed bleeding after endoscopic resections, Endoscopy International Open, 4: E415-E419 (2016).

Reich, I. et al., Chapter 36: Tonicity, Osmoticity, Osmolality, and Osmolarity, Remington: Practice of The Science and Pharmacy, 19th edition, Mack Publishing Company, 613-621 (1995).

Spotnitz, W. D. and Banks, S., Hemostats, sealants and adhesives: components of the surgical toolbox, Transfusion, 48: 1502-1516 (2008).

Stark, J. and De Leval, M., Experience with fibrin seal (Tisseel) in operations for congenital heart defects, Ann. Thorac, Surg., 38(4):411-3 (1984).

Stiuso, P. et al., The self-association of protein SV-IV and its possible functional implications, Eur. J. Biochem., 266(3):1029-35 (1999).

Sun-Sri, TITAN2® 17mm filter, 2009, accessed from https://sun-sri.com/products/17mm_filters.aspx, accessed on May 22, 2019.

Tam, J. et al., Fractional skin harvesting: autologous skin grafting without donor-site morbidity, Plastic and Reconstructive Surgery Global Open, 1(6): e47 (2013).

Thermo Scientific, MaxQ 2000 Open-Air Platform Shaker, 30 pages (2010).

Whatman Product Guide, 2 pages (1997).

Wu, M. et al., Self-assembling peptide nanofibrous hydrogel on immediate hemostasis and accelerative osteosis, Biomacromolecules, 16: 3112-3118 (2015).

Wu, X. et al, Functional self-assembling peptide nanofiber hydrogel for peripheral nerve regeneration, Regenerative Biomaterials, 21-30 (2016).

Yamamoto, H. et al, A novel method of endoscopic mucosal resection using sodium hyaluronate, Gastrointestinal Endoscopy, 50(2): 251-256 (1999).

Yoshida, M, et al., Initial clinical trial of a novel hemostat, TDM-621, in the endoscopic treatments of the gastric tumors, J. Gastroenterol Hepatol., 29: 77-79 (2014).

\* cited by examiner

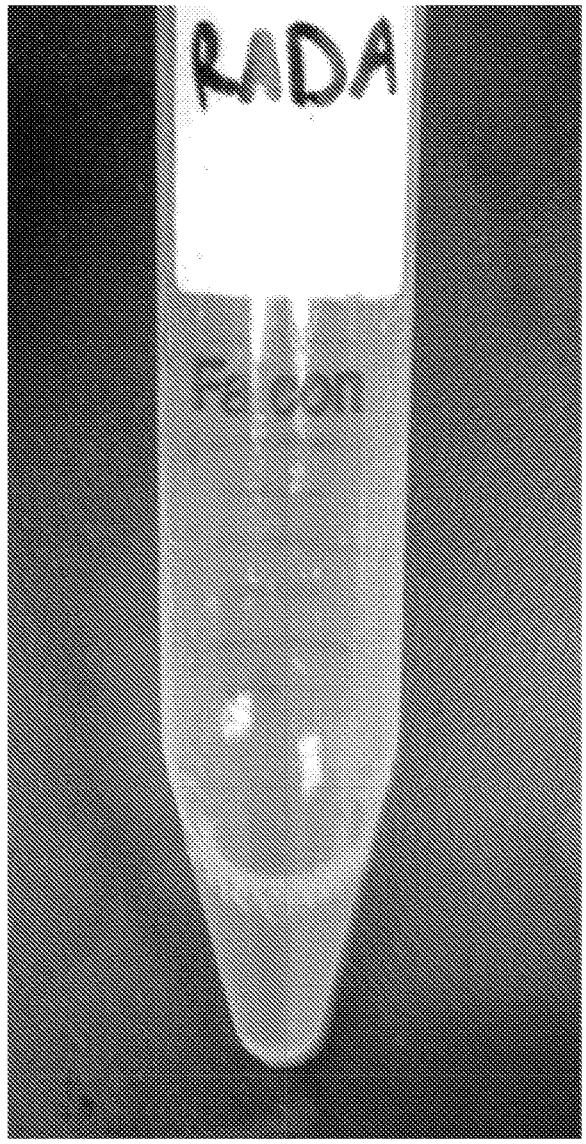 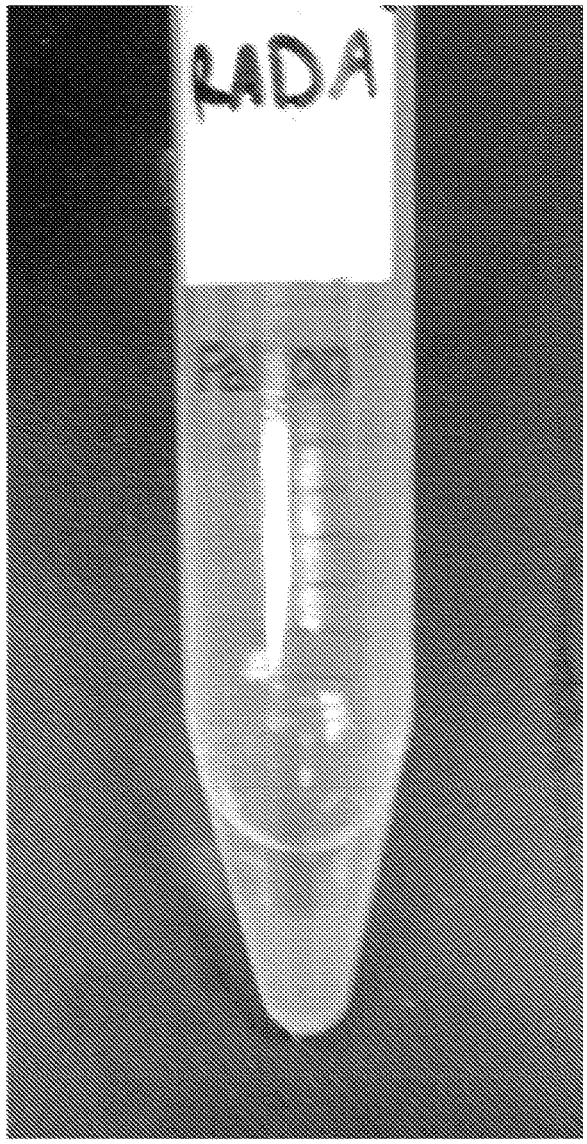
*Figure 6A*         *Figure 6B*

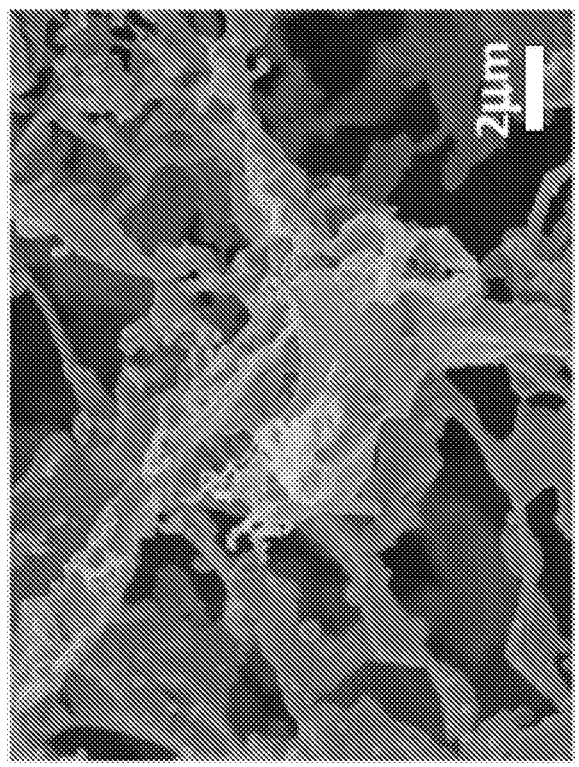
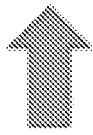
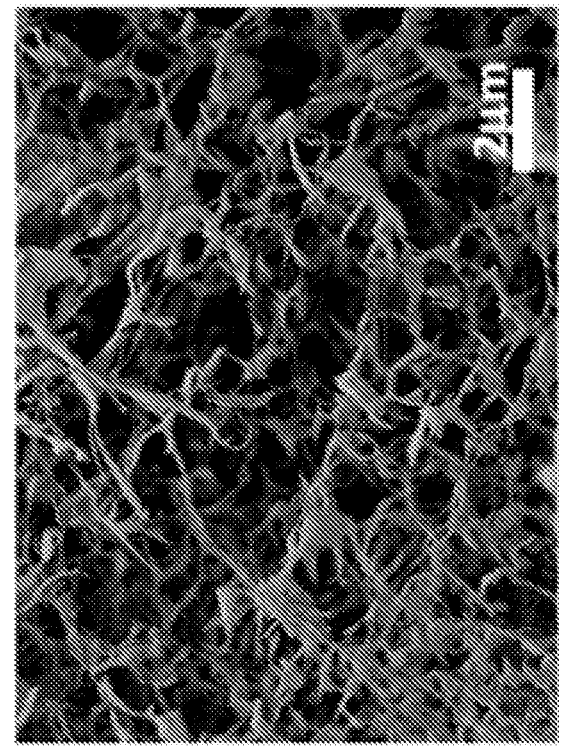
Figure 17B

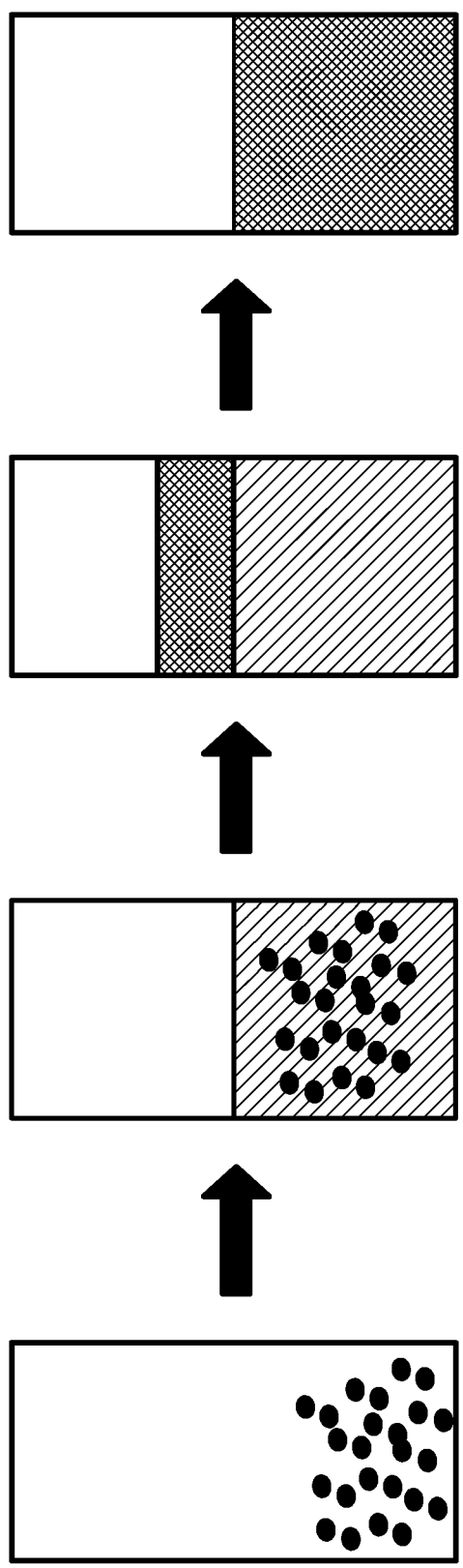

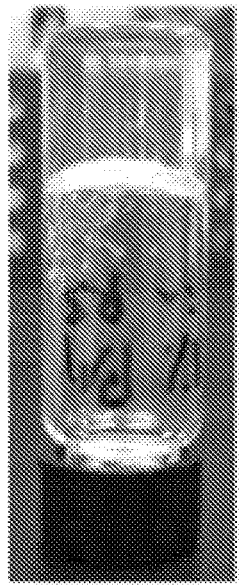 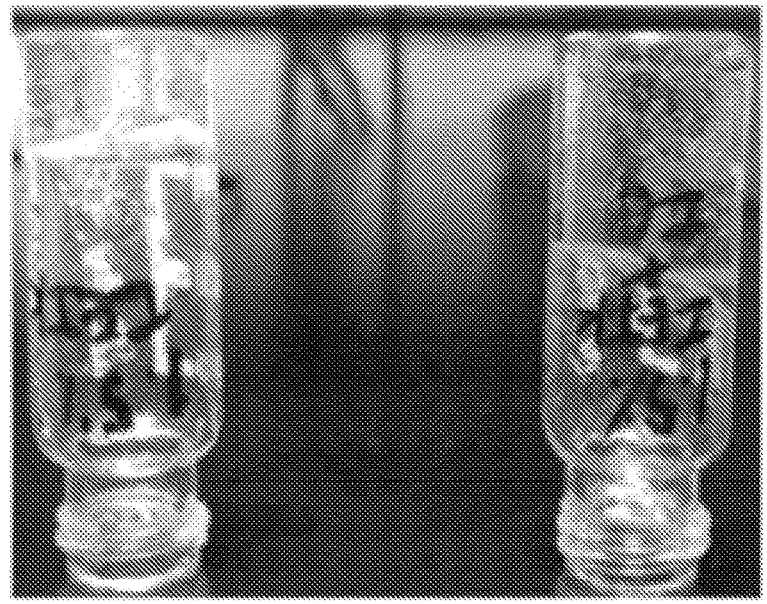
*Figure 47D*      *Figure 47E*
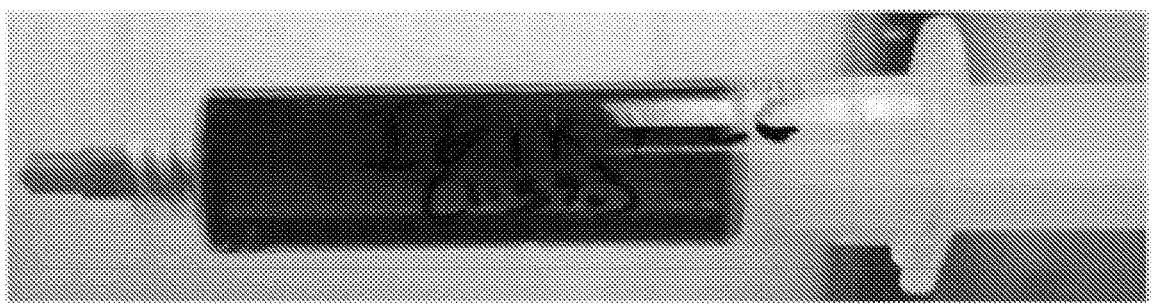
*Figure 47F*

SELF-ASSEMBLING PEPTIDE COMPOSITIONS

CROSS REFERENCE TO RELATED APPLICATIONS

This application is a U.S. National Stage Application filed under 35 U.S.C. § 371 based on International Application No. PCT/US2015/019796, filed Mar. 10, 2015, which claims benefit under 35 U.S.C. § 119(e) of U.S. provisional patent application Ser. No. 61/950,529, filed Mar. 10, 2014, the entire contents of each of which are hereby incorporated by reference.

SEQUENCE LISTING

This application makes reference to a sequence listing submitted in electronic form as an ascii.txt file named "2004837-0120_Sequences.txt". The .txt file was generated on Jun. 16, 2017 and is 2 kb in size. The entire contents of the Sequence Listing are herein incorporated by reference.

BACKGROUND

Peptide agents with the ability to self-assemble into gel structures have a wide variety of uses in therapeutic and research contexts. One such peptide agent, for example, a synthetic, 16-amino acid polypeptide with a repeating sequence of arginine, alanine, and aspartic acid (i.e., RADARADARADARADA [SEQ ID NO:1], also known as "RADA16"), is commercially available under the trade names PuraStat®, PuraMatrix®, and PuraMatrix GMP® from 3-D Matrix Medical Technology, and has demonstrated utility in a wide range of laboratory and clinical applications, including cell culture, drug delivery, accelerated cartilage and bone growth, and regeneration of CNS, soft tissue, and cardiac muscle, and furthermore as a matrix, scaffold, or tether that can be associated with one or more detectable agents, biologically active agents, cells, and/or cellular components.

SUMMARY

The present disclosure provides, among other things, certain peptide compositions (and particularly certain compositions of self-assembling peptide agents), and technologies relating thereto. In some embodiments, such compositions may be or comprise solutions. In some embodiments, such compositions may be or comprise gels. In some embodiments, such compositions may be or comprise solid (e.g., dried/lyophilized) peptides.

For example, the present disclosure demonstrates that particular peptide compositions (i.e., peptide compositions having specific concentration, ionic strength, pH, viscosity and/or other characteristics) have useful and/or surprising attributes (e.g., gelation or self-assembly kinetics [e.g., rate of gelation and/or rate and reversibility of peptide self-assembly], stiffness [e.g., as assessed via storage modulus], and/or other mechanical properties). In some embodiments, the present disclosure demonstrates particular utility of certain such compositions in specific contexts (e.g., in certain in vivo or in vitro applications).

Among other things, the present disclosure provides guidelines that permit selection, design, and/or formulation of particular peptide compositions useful in certain contexts or applications.

The present disclosure establishes the extent to which certain cations and anions interact with self-assembling peptide agents, and furthermore how such interactions can alter certain material (e.g., rheological) properties (e.g., increase mechanical stiffness and/or viscosity) of peptide compositions. Still further, the present disclosure establishes how such interactions can influence, among other things, gelation kinetics, restoration of gelled state (e.g., timing and/or extent of gelation and/or restoration of gel properties) after exposure to deformation (e.g., mechanical perturbation or other disruption).

Studies described herein have identified the source of various problems with certain existing self-assembling peptide technologies, and furthermore define particularly useful and/or necessary attributes and/or characteristics specific to particular applications of peptide composition technologies.

In some embodiments, peptides included in provided compositions are self-assembling peptides. In some embodiments, peptides included in provided compositions are amphiphilic peptides. In some embodiments, peptides included in provided compositions have an amino acid sequence characterized by at least one stretch (e.g., of at least 4, 5, 6, 7, 8, 9, 10, 11, 12, 13, 14, 15, 16, 17, 18, 19, 20 etc. amino acids) of alternating hydrophilic and hydrophobic amino acids. In some embodiments, peptides included in provided compositions have an amino acid sequence that includes one or more repeats of Arg-Ala-Asp-Ala (RADA; SEQ ID NO:4). In some embodiments, peptides included in provided compositions have an amino acid sequence that comprises or consists of repeated units of the sequence Lys-Leu-Asp-Leu (KLDL; SEQ ID NO:5). In some embodiments, peptides included in provided compositions have an amino acid sequence that comprises or consists of repeated units of the sequence Ile-Glu-Ile-Lys (IEIK; SEQ ID NO:6). In some embodiments, the peptides may be IEIK13 (SEQ ID NO:3), KLD12 (SEQ ID NO:2), or RADA16 (SEQ ID NO:1). In some embodiments, compositions of these peptides may have enhanced properties relative to appropriate reference compositions that have different (e.g., lower) pH level, and/or ionic strength.

Peptide compositions at a milder pH level may have stiffer rheological properties rendering them suitable for a broader range of applications. Environmental pH change to over 4.0 may also beneficially impact gelation kinetics from peptide compositions. In some embodiments, the increased pH may be physiological pH which may occur when the peptide compositions are placed into the body.

In accordance with one or more aspects, rheological properties of certain peptide compositions, including but not limited to IEIK13 (SEQ ID NO:3), KLD12 (SEQ ID NO:2), and RADA16 (SEQ ID NO:1), may be enhanced by maintaining increased ionic strength. In some embodiments, the ionic strength may be lower than critical ionic strength. In some embodiments, peptides compositions may be dissolved in water with salts instead of pure water. In some embodiments, the ionic strengths may be lower than their critical ionic strengths.

In some embodiment, increased ionic strength may beneficially impact stiffness and/or gelation kinetics to peptide compositions rendering them suitable for a broader range of applications. In some embodiments, increased ionic strength may be physiological ionic strength, which may occur when peptide compositions are placed into the body.

In accordance with one or more aspects, properties of certain peptide compositions, including but not limited to IEIK13 (SEQ ID NO:3), KLD12 (SEQ ID NO:2), and RADA16 (SEQ ID NO:1), may be enhanced by maintaining their pH level at about 3.5 or less and, at the same time, their salt concentrations at less than their critical ionic strength levels (i.e. no precipitation).

In accordance with one or more aspects, self-assembling peptides, for example, IEIK13 (SEQ ID NO:3), KLD12 (SEQ ID NO:2), and RADA16 (SEQ ID NO:1), may be characterized in terms of properties including appearance, pH level, ionic strength level, gelation kinetics, rheological properties, and cell viability to optimize peptide formulations for various applications. IEIK13 (SEQ ID NO:3) and KLD12 (SEQ ID NO:2) may be characterized as similar peptide compositions to RADA16 (SEQ ID NO:1) in terms of basic gelation properties and other characteristics.

In some embodiments, a peptide may have a length within the range of about 6 to about 20 amino acids and an amino acid sequence of alternating hydrophobic amino acid and hydrophilic amino acids.

In some embodiments, a peptide composition may be solution, gel, or any combination thereof.

In some embodiments, a peptide composition may be at a concentration of at least 0.05%. In some embodiments, a peptide composition may be present at a concentration of less than 3%

In some embodiments, a peptide composition may have a pH within the range of about 2.5 to about 4.0, or within the range of about 3.0 to about 4.0. In some embodiments, pH of a peptide composition can be achieved with a solution selected from the group consisting of sodium hydroxide or, potassium hydroxide, calcium hydroxide, sodium carbonate, sodium acetate, sodium sulfide, DMEM (Dulbecco's modified Eagle's medium), and PBS (Phosphate-Buffered Saline).

In some embodiments, an ionic strength of a peptide composition may be about 0.0001 M to about 1.5 M. In some embodiments, an ionic strength of a peptide composition may be adjusted by mixing common salts, for example, NaCl, KCl, $MgCl_2$, $CaCl_2$, $CaSO_4$, DPBS (Dulbecco's Phosphate-Buffered Saline, 10×). In some embodiments, ionic strengths of peptide compositions may be adjusted by mixing common salts, wherein one or more common salts are composed of one or more salt forming cations and one or more salt forming anions, wherein the salt forming cations are selected from the group consisting of ammonium, calcium, iron, magnesium, potassium, pyridinium, quaternary ammonium, and sodium, wherein the salt forming anions are selected from the group consisting of acetate, carbonate, chloride, citrate, cyanide, fluoride, nitrate, nitrite, and phosphate.

In some embodiments, a peptide composition may have a viscosity with the range of about 1 to about 10000 Pa·S. In some embodiments, a peptide composition may have a storage modulus with the range of about 50 to about 2500 Pa.

In some embodiments, a method of selecting a peptide composition for applications to a particular in vivo site may comprise steps of determining one or more parameters selected from the group consisting of storage modulus, viscosity, gelation time, restoration time and/or extent, etc. for the peptide composition, comparing the determined parameters to specifications for various applications, choosing the peptide composition in light of the comparison; and administering the chosen peptide composition to the site.

In some particular embodiments, the present disclosure provides liquid peptide compositions that may, for example, comprise a peptide having a length within the range of about 6 to about 20 amino acids and an amino acid sequence of alternating hydrophobic amino acid and hydrophilic amino acids, and may be characterized in that (i) it has a viscosity within the range of about 1 Pa·s to about 500,000 Pa·s at room temperature; (ii) it has a storage modulus at 1 rad/sec of frequency and 1 Pa of oscillation stress within the range of about 1 to about 5000 Pa; and/or (iii) it forms a gel within a time period about 0 to about 30 s when exposed to/maintained under pH within the range of about 2.5 to about 4.0 or and/or ionic strength within the range of about 0.0001 M to about 1.5 M. In some embodiments, such a composition is an aqueous composition.

Also in some particular embodiments, the present disclosure provides methods of designing, selecting, and or producing a peptide composition that is particularly appropriate for use in a certain specific context. In some such embodiments, the certain specific context is or comprises application to a particular in vivo site. In some embodiments, such provided methods may comprise, for example: (i) determining one or more parameters selected from the group consisting of storage modulus, viscosity, gelation time, shear-thinning property, peptide nano-fiber re-assembly time that is, and/or one or more other parameters as described herein that is appropriate for application to the particular in vivo site; and (ii) designing, selecting, and/or producing a peptide composition characterized by such parameters, in accordance with guidance provided herein.

Alternatively or additionally, in some particular embodiments, the present disclosure provides methods of selecting particular peptide compositions, for example for administration to certain in vivo sites; exemplary such methods may comprise steps of (i) determining one or more parameters selected from the group consisting of storage modulus, viscosity, gelation time, shear-thinning property, peptide nano-fiber re-assembly time that is, and/or one or more other parameters as described herein for a peptide composition; (ii) comparing the determined one or more parameters to a set of characteristics determined to be appropriate for application to the particular in vivo site; (iii) choosing the peptide composition in light of the comparison; and (iv) administering the chosen peptide composition to the site.

BRIEF DESCRIPTION OF THE DRAWING

Objects and features of the invention can be better understood with reference to the drawings described below, and the claims.

FIG. 2A depicts a stress sweep test performed at 1 Pa and 10 rad/s. FIG. 2B shows measured storage modulus as a function of RADA16 (SEQ ID NO:1) concentration. Storage modulus of RADA16 (SEQ ID NO:1) compositions may have a linear relationship with their concentration.

FIG. 3A depicts a stress sweep test performed at 1 Pa and 10 rad/s. FIG. 3B shows measured storage moduli as a function of IEIK13 (SEQ ID NO:3) concentration. Storage moduli of IEIK13 (SEQ ID NO:3) compositions may have a linear relationship with their concentrations.

FIG. 4A depicts a stress sweep test performed at 1 Pa and 10 rad/s. FIG. 4B shows measured storage moduli as a function of KLD12 (SEQ ID NO:2) concentration. Storage moduli of KLD12 (SEQ ID NO:2) compositions may have a linear relationship with their concentrations.

FIG. 5A depicts storage modulus data (performed at 1 Pa and 10 rad/s) before or after the DMEM treatment on peptide compositions. FIG. 5B shows fold increases of storage modulus after the DMEM treatment.

FIG. 6A is a picture of RADA16 (SEQ ID NO:1) and DMEM mixture (1:1 volume ratio). The mixture was runny and cloudy. FIG. 6B shows the mixture after centrifugation. RADA16 (SEQ ID NO:1) (i.e. the translucent accumulation at the bottom of the centrifuge tube) was precipitated from the mixture.

FIG. 11A is measurements of 1% RADA16 (SEQ ID NO:1) at pH 2.5 and 3.4. FIG. 11B is measurements of 2.5% RADA16 (SEQ ID NO:1) at pH 2.5 and 3.4.

FIG. 17B shows SEM images of IEIK13 (SEQ ID NO:3) before and after the DMEM treatment. IEIK13 (SEQ ID NO:3) fibers after the DMEM treatment may be thicker than the fibers before the DMEM treatment.

FIG. 22A is measurements before the DMEM treatment. FIG. 22B is measurements after the DMEM treatment.

FIG. 23A is measurements before the DMEM treatment. FIG. 23B is measurements after the DMEM treatment.

FIG. 24 includes 2.5% RADA16 (SEQ ID NO:1) data at pH 2.2, 2.6, 2.8, 3.1 and 3.4.

FIG. 25 includes 1.5% IEIK13 (SEQ ID NO:3) data at pH 2.3, 2.6, 2.9 and 3.2. Time sweep tests were performed at 1 rad/sec and at 1 Pa with 20 mm plates and 500 μm gap distance. During time sweep tests, DMEM was added into the chamber surrounding the measuring plates to soak the peptides at time=0.

FIG. 27 is measurements of 1% KLD12 (SEQ ID NO:2) with or without NaCl solution (0.2M ionic strength).

FIG. 28 is measurements of 1% IEIK13 (SEQ ID NO:3) with or without NaCl solution (0.02M ionic strength).

FIG. 29 is measurements of 1% RADA16 (SEQ ID NO:1) with or without NaCl solution (0.7 M ionic strength).

FIGS. 41A, 41B, 41C and 41D illustrate steps utilized in preparing peptide compositions with different salts and/or salt concentrations as described in Examples 4 and 7. Those of ordinary skill will appreciate that a similar strategy can be utilized, for example, to analyze peptide compositions with different pHs, peptide concentrations, etc. In FIG. 41A, the peptide powder was placed with a glass vial. In FIG. 41B, the peptide powder was dissolved first in deionized water at a selected fraction of the final volume; vortexing and/or sonication was utilized as desired to achieve or ensure complete solubilization. In FIG. 41C, a concentrated salt solution was added on top, in an amount and concentration dependent on the volume of deionized water used. In FIG. 41D, the solution was mixed, for example by vortexing.

FIGS. 42A, 42B, 42C, 42D, 42E, 42F and 42G are upright and inverted pictures of 0.5% RADA16 (SEQ ID NO:1) and 0, 0.005, 0.05, 0.125, 0.250, 0.500, and 1 M CaCl2 mixture, respectively. FIG. 42E shows an optimal and fully functional gel. FIG. 42F shows a semi-functional gel. FIG. 42G shows a non-functional gel.

FIG. 47D is a picture of RADA16 (SEQ ID NO:1) with Ringer's Solution inverted. FIG. 46E is pictures of IEIK13 SEQ ID NO:3) and IEIK13 (SEQ ID NO:3) with Indigo Carmine inverted. FIG. 47F is a picture of IEIK13 (SEQ ID NO:3) with Indigo Carmine and placed within a syringe.

DEFINITIONS

Figure 1:
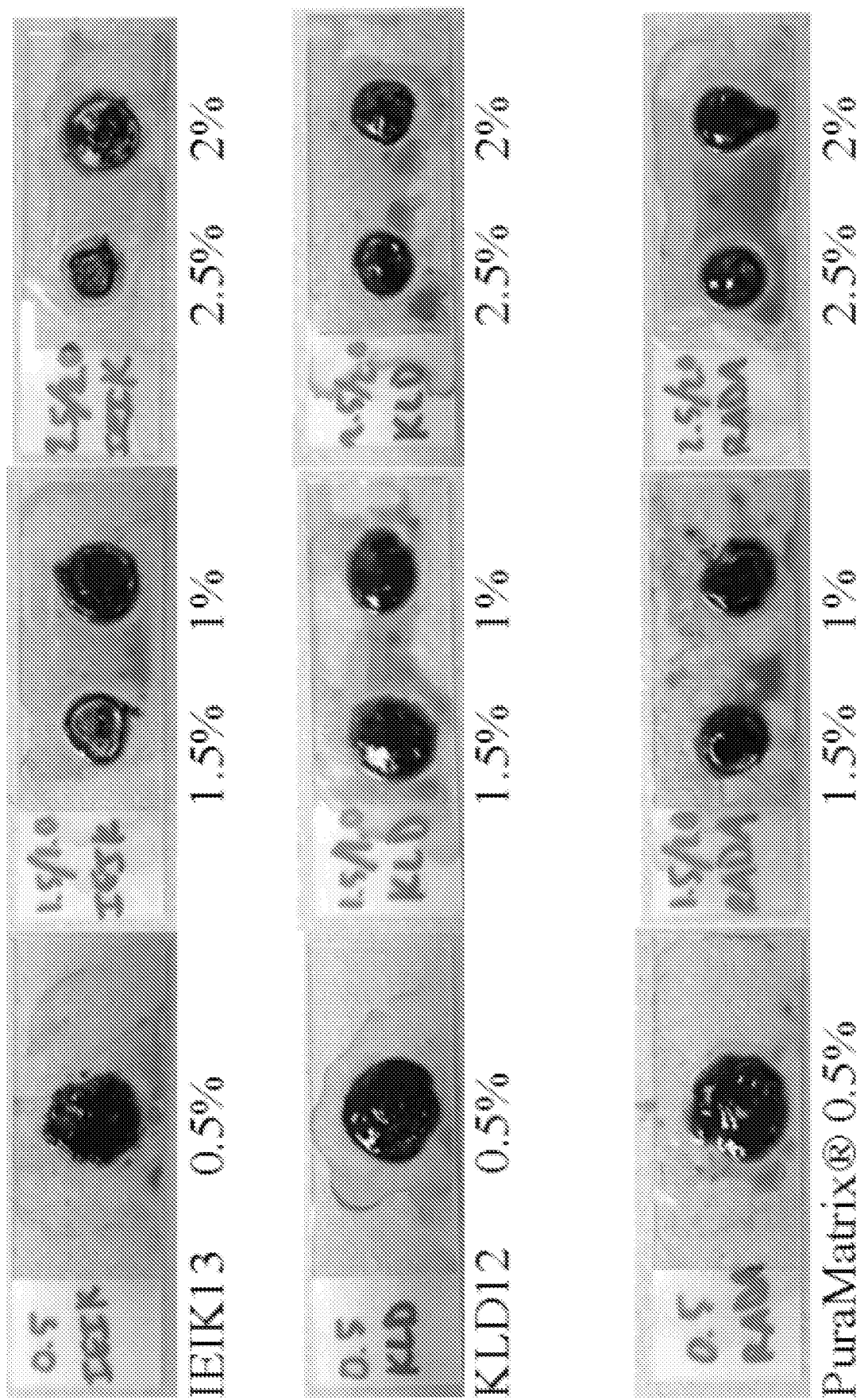
FIG. 1 shows exemplary gel formations of peptide compositions in PBS buffer solutions. RADA16 (SEQ ID NO:1), IEIK13 (SEQ ID NO:3), and KLD12 (SEQ ID NO:2) were plated at varying concentrations of 0.5%, 1.0%, 1.5%, 2.0% and 2.5%. RADA16 (SEQ ID NO:1), IEIK13 (SEQ ID NO:3), and KLD12 (SEQ ID NO:2) were gelled at all concentrations.

The term "agent" as used herein may refer to a compound or entity of any chemical class including, for example, polypeptides, nucleic acids, saccharides, lipids, small molecules, metals, or combinations thereof. In some embodiments, an agent is or comprises a natural product in that it is found in and/or is obtained from nature. In some embodiments, an agent is or comprises one or more entities that is man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents are provided as collections or libraries, for example that may be screened to identify or characterize active agents within them. Some particular embodiments of agents that may be utilized in accordance with the present invention include small molecules, antibodies, antibody fragments, aptamers, nucleic acids (e.g., siRNAs, shRNAs, DNA/RNA hybrids, antisense oligonucleotides, ribozymes), peptides, peptide mimetics, etc. In some embodiments, an agent is or comprises a polymer. In some embodiments, an agent is not a polymer and/or is substantially free of any polymer. In some embodiments, an agent contains at least one polymeric moiety. In some embodiments, an agent lacks or is substantially free of any polymeric moiety.

As used herein, the term "amino acid," in its broadest sense, refers to any compound and/or substance that can be incorporated into a polypeptide chain, e.g., through formation of one or more peptide bonds. In some embodiments, an amino acid has the general structure $H_2N-C(H)(R)-COOH$. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. In some embodiments, an amino acid, including a carboxy- and/or amino-terminal amino acid in a polypeptide, can contain a structural modification as compared with the general structure above. For example, in some embodiments, an amino acid may be modified by methylation, amidation, acetylation, and/or substitution as compared with the general structure. In some embodiments, such modification may, for example, alter the circulating half life of a polypeptide containing the modified amino acid as compared with one containing an otherwise identical unmodified amino acid. In some embodiments, such modification does not significantly alter a relevant activity of a polypeptide containing the modified amino acid, as compared with one containing an otherwise identical unmodified amino acid. As will be clear from context, in some embodiments, the term "amino acid" is used to refer to a free amino acid; in some embodiments it is used to refer to an amino acid residue of a polypeptide.

As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Two events or entities are "associated" with one another, as that term is used herein, if the presence, level and/or form of one is correlated with that of the other. For example, a particular entity (e.g., polypeptide, genetic signature, metabolite, etc.) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

The term "comparable" is used herein to describe two (or more) sets of conditions, circumstances, individuals, or populations that are sufficiently similar to one another to permit comparison of results obtained or phenomena observed. In some embodiments, comparable sets of conditions, circumstances, individuals, or populations are characterized by a plurality of substantially identical features and one or a small number of varied features. Those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied. Those skilled in the art will appreciate that relative language used herein (e.g., enhanced, activated, reduced, inhibited, etc.) will typically refer to comparisons made under comparable conditions.)

Certain methodologies described herein include a step of "determining". Those of ordinary skill in the art, reading the present specification, will appreciate that such "determining" can utilize or be accomplished through use of any of a variety of techniques available to those skilled in the art, including for example specific techniques explicitly referred to herein. In some embodiments, determining involves manipulation of a physical sample. In some embodiments, determining involves consideration and/or manipulation of data or information, for example utilizing a computer or other processing unit adapted to perform a relevant analysis. In some embodiments, determining involves receiving relevant information and/or materials from a source. In some embodiments, determining involves comparing one or more features of a sample or entity to a comparable reference.

The term "gel" as used herein refers to viscoelastic materials whose rheological properties distinguish them from solutions, solids, etc. In some embodiments, a composition is considered to be a gel if its storage modulus (G') is larger than its modulus (G"). In some embodiments, a composition is considered to be a gel if there are chemical or physical crosslinked networks in solution, which is distinguished from entangled molecules in viscous solution.

The term "in vitro" as used herein refers to events that occur in an artificial environment, e.g., in a test tube or reaction vessel, in cell culture, etc., rather than within a multi-cellular organism.

The term "in vivo" as used herein refers to events that occur within a multi-cellular organism, such as a human and a non-human animal. In the context of cell-based systems, the term may be used to refer to events that occur within a living cell (as opposed to, for example, in vitro systems).

The term "peptide" as used herein refers to a polypeptide that is typically relatively short, for example having a length of less than about 100 amino acids, less than about 50 amino acids, less than 20 amino acids, or less than 10 amino acids.

The term "polypeptide" as used herein refers to any polymeric chain of amino acids. In some embodiments, a polypeptide has an amino acid sequence that occurs in nature. In some embodiments, a polypeptide has an amino acid sequence that does not occur in nature. In some embodiments, a polypeptide has an amino acid sequence that is engineered in that it is designed and/or produced through action of the hand of man. In some embodiments, a polypeptide may comprise or consist of natural amino acids, non-natural amino acids, or both. In some embodiments, a polypeptide may comprise or consist of only natural amino acids or only non-natural amino acids. In some embodiments, a polypeptide may comprise D-amino acids, L-amino acids, or both. In some embodiments, a polypeptide may comprise only D-amino acids. In some embodiments, a polypeptide may comprise only L-amino acids. In some embodiments, a polypeptide may include one or more pendant groups or other modifications, e.g., modifying or attached to one or more amino acid side chains, at the polypeptide's N-terminus, at the polypeptide's C-terminus, or any combination thereof. In some embodiments, such pendant groups or modifications may be selected from the group consisting of acetylation, amidation, lipidation, methylation, pegylation, etc., including combinations thereof. In some embodiments, a polypeptide may be cyclic, and/or may comprise a cyclic portion. In some embodiments, a polypeptide is not cyclic and/or does not comprise any cyclic portion. In some embodiments, a polypeptide is linear. In some embodiments, a polypeptide may be or comprise a stapled polypeptide. In some embodiments, the term "polypeptide" may be appended to a name of a reference polypeptide, activity, or structure; in such instances it is used herein to refer to polypeptides that share the relevant activity or structure and thus can be considered to be members of the same class or family of polypeptides. For each such class, the present specification provides and/or those skilled in the art will be aware of exemplary polypeptides within the class whose amino acid sequences and/or functions are known; in some embodiments, such exemplary polypeptides are reference polypeptides for the polypeptide class or family. In some embodiments, a member of a polypeptide class or family shows significant sequence homology or identity with, shares a common sequence motif (e.g., a characteristic sequence element) with, and/or shares a common activity (in some embodiments at a comparable level or within a designated range) with a reference polypeptide of the class; in some embodiments with all polypeptides within the class). For example, in some embodiments, a member polypeptide shows an overall degree of sequence homology or identity with a reference polypeptide that is at least about 30-40%, and is often greater than about 50%, 60%, 70%, 80%, 90%, 91%, 92%, 93%, 94%, 95%, 96%, 97%, 98%, 99% or more and/or includes at least one region (e.g., a conserved region that may in some embodiments be or comprise a characteristic sequence element) that shows very high sequence identity, often greater than 90% or even 95%, 96%, 97%, 98%, or 99%. Such a conserved region usually encompasses at least 3-4 and often up to 20 or more amino acids; in some embodiments, a conserved region encompasses at least one stretch of at least 2, 3, 4, 5, 6, 7, 8, 9, 10, 11, 12, 13, 14, 15 or more contiguous amino acids. In some embodiments, a useful polypeptide may comprise or consist of a fragment of a parent polypeptide. In some embodiments, a useful polypeptide as may comprise or consist of a plurality of fragments, each of which is found in the same parent polypeptide in a different spatial arrangement relative to one another than is found in the polypeptide of interest (e.g., fragments that are directly linked in the parent may be spatially separated in the polypeptide of interest or vice versa, and/or fragments may be present in a different order in the polypeptide of interest than in the parent), so that the polypeptide of interest is a derivative of its parent polypeptide.

The term "reference" as used herein describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

The term "self-assembling" is used herein in reference to certain polypeptides that, under appropriate conditions, can spontaneously self-associate into structures so that, for example, solutions (e.g., aqueous solutions) containing them develop gel character. In some embodiments, interactions between and among individual self-assembling polypeptides within a composition are reversible, such that the composition may reversibly transition between a gel state and a solution state. In some embodiments, self-assembly (and/or disassembly) is responsive to one or more environmental triggers (e.g., change in one or more of pH, temperature, ionic strength, osmolarity, osmolality, applied pressure, applied shear stress, etc.). In some embodiments, compositions of self-assembling polypeptides are characterized by detectable beta-sheet structure when the polypeptides are in an assembled state.

DETAILED DESCRIPTION OF CERTAIN EMBODIMENTS

In accordance with one or more embodiments, the present invention provides preparations of certain peptides that may offer enhanced utility and improved performance as compared with other preparations of the same peptides. In some embodiments, disclosed preparations may offer different or unique properties that, for example may address previously unmet requirements associated with various research and/or clinical applications. In some embodiments, certain desirable features of provided peptide preparations are provided by elevating pH level of the preparation as compared with a standard or reference preparation of the peptide and/or by adding one or more salts to the preparation, as compared with the type and/or amount of salt in a standard or reference preparation. In some embodiments, provided preparations are characterized by more stable hydrogel formation, and/or other attributes relative to a standard or reference preparation, as described herein.

Peptides

In accordance with one or more embodiments, peptide compositions may include an amphiphilic polypeptide having about 6 to about 200 amino acid residues. In certain embodiments, the may have a length of at least about 7 amino acids. In certain embodiments, the polypeptides may have a length of between about 7 to about 17 amino acids. In certain embodiments, the polypeptides may have a length of at least 8 amino acids, at least about 12 amino acids, or at least about 16 amino acids.

In some embodiments, as is understood in the art, an amphiphilic polypeptide is one whose sequence includes both hydrophilic amino acids and hydrophobic amino acids. In some embodiments, such hydrophilic amino acids and hydrophobic amino acids may be alternately bonded, so that the peptide has an amino acid sequence of alternating hydrophilic and hydrophobic amino acids. In some embodiments, a polypeptide for use in accordance with the present disclosure has an amino acid sequence that comprises or consists of repeated units of the sequence Arg-Ala-Asp-Ala (RADA; SEQ ID NO:4). In some embodiments, a polypeptide for use in accordance with the present disclosure has an amino acid sequence that comprises or consists of repeated units of the sequence Lys-Leu-Asp-Leu (KLDL; SEQ ID NO:5). In some embodiments, a polypeptide for use in accordance with the present disclosure has an amino acid sequence that comprises or consists of repeated units of the sequence Ile-Glu-Ile-Lys (IEIK; SEQ ID NO:6).

In some embodiments, a peptide for use in accordance with the present disclosure, may generally be self-assembling, and/or may exhibit a beta-sheet structure in aqueous solution under certain conditions.

In some embodiments, a peptide for use in accordance with the present disclosure has an amino acid sequence: Arg-Ala-Asp-Ala-Arg-Ala-Asp-Ala-Arg-Ala-Asp-Ala-Arg-Ala-Asp-Ala (i.e., RADA16, aka [RADA]4; SEQ ID NO:1). In some embodiments, a peptide for use in accordance with the present disclosure has an amino acid sequence: Lys-Leu-Asp-Leu-Lys-Leu-Asp-Leu-Lys-Leu-Asp-Leu (i.e., KLDL12, aka [KLDL])3 aka KLD12; SEQ ID NO: 2). a peptide for use in accordance with the present disclosure has an amino acid sequence: Ile-Glu-Ile-Lys-Ile-Glu-Ile-Lys-Ile-Glu-Ile-Lys-Ile (i.e., IEIK13, aka (IEIK)3I; SEQ ID NO:3)

Those skilled in the art, reading the present specification, will appreciate that any of a variety of other peptides may alternatively be employed in the practice of the present invention. In some embodiments, for example, one or more peptides as described in Published US Patent Application US2009/0111734 A1, Published US Patent Application US2008/0032934 A1, Published US Patent Application US2014/0038909 A1, Issued U.S. Pat. No. 7,846,891 B2, Issued U.S. Pat. No. 7,713,923 B2, Issued U.S. Pat. No. 5,670,483 B2, the relevant contents of which are incorporated herein by reference.

In some embodiments, a peptide for use in accordance with the present invention have an amino acid sequence that comprises or consists of a sequence represented by one of the following formulae:

$((XY)_l\text{-}(ZY)_m)_n$                                                     Formula (a)

$((YX)_l\text{-}(YZ)_m)_n$                                                   Formula (b)

$((ZY)_l\text{-}(XY)_m)_n$                                                   Formula (c)

$((YZ)_l\text{-}(YX)_m)_n$                                                   Formula (d), wherein X represents an acidic amino acid, Y represents a hydrophobic amino acid and Z represents a basic amino acid, and l, m and n are all integers (n(l+m)<200), (1≤n≤100))

Compositions

In some embodiments, peptide compositions in accordance with the present disclosure may be characterized by particular rheological and/or optical properties. In some embodiments, such rheological properties may include one or more of gelation kinetics, reversible assembly characteristics, storage modulus, viscosity, etc. In some embodiments, one or more rheological properties may be tested and/or determined (e.g., measured); in some embodiments, one or more rheological properties may be assessed by visual observation.

In some embodiments, relevant optical properties may include one or more of degree of transparency, optical clarity, etc. In some embodiments, one or more optical properties may be tested and/or determined (e.g., measured); in some embodiments, one or more optical properties may be assessed by visual observation. In some embodiments, optical clarity of particular compositions may be described as clear, slightly cloudy, or cloudy. In some embodiments, provided compositions are clear In some embodiments, provided compositions are characterized by a particular level of stiffness. In some embodiments, stiffness is assessed by determination of storage modulus. As will be understood by those skilled in the art, in general, storage modulus and stiffness have a positive correlation; that is, higher storage modulus is related to higher stiffness.

In some embodiments, provided compositions are characterized by particular gelation properties (e.g., a particular degree of gelation within a particular period of time). In some embodiments, provided compositions are characterized by substantially complete gelation within a time period with the range of about 10 second to about 48 hours.

In some embodiments, provided compositions are characterized by a particular degree of restoration of gelation and/or other material and/or rheological properties. For example, in some embodiments, when provided compositions that have gelled are subjected to disruption, they display an ability to re-gel within a particular period of time (e.g., within a range of about 10 second to about 48 hours), and into a gel whose mechanical and/or rheological properties are reasonably comparable to those of the original gel.

In some embodiments, provided compositions are characterized by an ability to support cell growth and/or viability.

In some embodiments, one or more material (e.g., rheological) properties of a peptide composition described and/or utilized herein may be determined by, for example, by peptide identity (e.g., amino acid sequence, degree of hydrophobicity, etc.), peptide concentration, pH, ionic strength (e.g., salt concentration), ionic identity, etc., and combinations thereof.

Peptide Concentration

In accordance with one or more embodiments, rheological properties of peptide composition as described herein may be controlled by selection of peptide concentration. The present disclosure defines parameters that permit selection and/or production of peptide compositions with particular desired characteristics, for example as may be specifically preferred for a particular application or use of the compositions, through selection and/or adjustment of peptide concentration.

For example, the present disclosure demonstrates, among other things, that for many peptides, composition stiffness increases substantially linearly with peptide concentration. Furthermore, as described herein, certain peptide compositions demonstrated a shear thinning property over a critical stress level. Moreover, the present disclosure demonstrates that rheological properties achieved at a particular peptide concentration may vary depending on the identity of the peptide. For example, storage modulus of 1.5% KLD12 (SEQ ID NO:2) was found to be similar to that of 2.5% RADA16 (SEQ ID NO:1). The storage modulus of 1% IEIK13 (SEQ ID NO:3) was found to be similar to that of 2.5% KLD12 (SEQ ID NO:2) and higher than that of 2.5% RADA16 (SEQ ID NO:1). Overall, the order of rheological strength among the compositions tested in the present Examples was IEIK13 (SEQ ID NO:3)>KLD12 (SEQ ID NO:2)>RADA16 (SEQ ID NO:1), so a composition of IEIK13 (SEQ ID NO:3) showed greater rheological strength than did a composition of KLD12 (SEQ ID NO:2), which in turn showed greater rheological strength than did a composition of RADA16 (SEQ ID NO:1) when peptide concentration was the same in each case.

In some embodiments, peptide concentration in a peptide composition for use in accordance with the present is at least 0.05%, at least 0.25%, at least 0.5%, at least 0.75%, at least 1.0% or more. In some embodiments, peptide concentration in a peptide composition for use in accordance with the present is less than 5%, less than 4.5%, less than 4%, less than 3.5%, less than 3%, or less. In some embodiments, peptide concentration in a peptide composition for use in accordance with the present invention is within a range between about 0.5% and about 3%. In some embodiments, peptide concentration in a peptide composition for use in accordance with the present invention is within a range between about 0.5% and about 2.5%. In some embodiments, peptide concentration in a peptide composition for use in accordance with the present invention is within a range between about 1% and about 3%. In some embodiments, peptide concentration in a peptide composition for use in accordance with the present invention is within a range between about 1% and about 2.5%. In some embodiments, peptide concentration in a peptide composition for use in accordance with the present invention is about 0.5%, about 1%, about 1.5%, about 2%, about 2.5%, about 3%, or more. In some particular embodiments, where the peptide is RADA16 (SEQ ID NO:1), peptide concentration in peptide compositions of the present invention is within a range of about 0.05% to about 10%.

In some particular embodiments, where the peptide is KLD12 (SEQ ID NO:2), peptide concentration in peptide compositions of the present invention is within a range of about 0.05% to about 10%.

In some particular embodiments, where the peptide is IEIK13 (SEQ ID NO:3), peptide concentration in peptide compositions of the present invention is within a range of about 0.05% to about 10%.

pH

The present disclosure demonstrates, among other things, that pH may impact properties of peptide compositions. As described herein, optimizing pH of peptide compositions may improve mechanical strengths, so that peptide compositions can be used for various clinical applications. Example 3 in this disclosure illustrates details of certain specific embodiments.

In accordance with one or more embodiments, provided peptide compositions may have a pH above (e.g., significantly above) the pI of the relevant peptide and/or of that obtained when the peptide is solubilized in water. In some embodiments, properties of peptide compositions may be controlled with pH. For example, in some embodiments, at pH within the range of about 2.5 to about 4.0, stiffness and/or viscosity of peptide compositions may be increased relative to that of an appropriate reference composition (e.g., of the same peptide at the same concentration in water).

In some embodiments, peptide compositions may comprise peptide and a solvent, typically an aqueous solvent, and pH may be adjusted via a pH-adjusting agent such as a base or acid. In some embodiments, peptide compositions comprise peptide and a buffer.

In some embodiments, a pH-adjusted peptide composition may comprise one or more of sodium hydroxide, potassium hydroxide, calcium hydroxide, sodium carbonate, sodium acetate, sodium sulfide, DMEM and/or PBS.

In some embodiments, an automated titration device may be implemented for pH adjustment.

In some embodiments, provided compositions have and/or are maintained at a pH above (e.g., materially above) the pI for the relevant peptide. In some embodiments, provided compositions have and/or are maintained at a pH above (e.g., materially above) that of a water solution of the same peptide at the same concentration. In some embodiments, provided compositions have and/or are maintained at a pH below that at which the composition is or becomes cloudy.

In some embodiments, provided compositions are characterized by a pH at or above about 2.5-4.0; in some embodiments, provided compositions are characterized by a pH closer to physiological pH. In some embodiments, provided compositions have a pH within the range of about 3.0-4.0. In some embodiments, provided compositions have a pH at or above about 2.5, 2.6, 2.7, 2.8, 2.9, 3.0, about 3.1, about 3.2, about 3.3, about 3.4, about 3.5 or higher. In some embodiments, provided compositions have a pH at or below about 4.3, about 4.2, about 4.1, about 4.0, about 39, about 3.7, about 3.6, about 3.5, about 3.4, or lower.

In some embodiments, elevated-pH compositions (i.e., compositions with a pH at or above about 2.5) as described herein are characterized by greater rheological stiffness and/or improved gelation properties as compared with an appropriate reference composition (e.g. a comparable composition of the same peptide at the same concentration and optionally with the same salts but at a different pH). In some embodiments, elevated pH compositions are useful in a wider range of applications than are corresponding reference compositions of lower pH.

The present disclosure specifically demonstrates that, in some embodiments, at elevated pH 3.5 or less, stiffness of IEIK13 (SEQ ID NO:3) compositions may be increased significantly, while those of RADA16 (SEQ ID NO:1) and KLD12 (SEQ ID NO:2) compositions may not. Without wishing to be bound by any particular theory, the present disclosure proposes that different behaviors of the peptide compositions at pH 3.5 or less are likely related to the pKa of aspartic acid (D) (pKa=3.71) in RADA16 (SEQ ID NO:1) and KLD12 (SEQ ID NO:2) and glutamic acid (E) (pKa=4.15) in IEIK13 (SEQ ID NO:3).

When pH is higher than pKa of aspartic acid (D) and glutamic acid (E), acidic groups in peptide chains are mostly negatively-charged. Negatively charged groups induce intra- or inter-molecular attractive charge-charge interactions with positively-charged groups in the peptide chains (i.e. arginine (R) in RADA16 (SEQ ID NO:1) and lysine (K) in IEIK13 (SEQ ID NO:3) and KLD12 (SEQ ID NO:2)) to form larger aggregates, which are a translucent or opaque (i.e. it is above its cloud point) and provide possible phase separation, rather than form nano-fibers (i.e. clear viscous compositions).

When pH is lower than pKa of aspartic acid (D) and glutamic acid (E) but close to the pKa, the more populated negatively-charged groups may induce stronger attractive charge-charge interactions with positive groups. The compositions may maintain the nano-fiber formation, so that the stiffness increases.

Certain particular exemplary peptide compositions having a pH of about 3.5 are presented in Table 2. Such compositions, which are considered "elevated pH compositions" herein, may provide improved performance (e.g., relative to otherwise comparable compositions of lower pH, such as relevant reference compositions as described herein, including in the Examples) in various applications. Mechanical strength and versatility of peptide compositions may be enhanced with elevated pH.

TABLE 2

Representative formulations for selected peptide compositions at around pH 3.5

| Peptides | Target-ed conc. (%) | Peptide powder (g) | Water (mL) | 0.1N NaOH (mL) | 1N NaOH (mL) |
|---|---|---|---|---|---|
| RADA16 | 1 | 1 | 91/99.1 | 9 | 0.9 |
| (SEQ ID NO: 1) | 2.5 | 2.5 | 77/97.7 | 23 | 2.3 |
| IEIK13 | 1 | 1 | 90/99 | 10 | 1 |
| (SEQ ID NO: 3) | 1.5 | 1.5 | 85/98.5 | 15 | 1.5 |
|  | 2 | 2 | 80/98 | 20 | 2.0 |
|  | 2.5 | 2.5 | 75/97.5 | 25 | 2.5 |
| KLD12 | 1 | 1 | 92/99.2 | 8 | 0.8 |
| (SEQ ID NO: 2) | 2.5 | 1.5 | 80/98 | 20 | 2.0 |

In accordance with one or more embodiments, pH may impact gelation kinetics (e.g., response time to begin gelation). Effects of pH on the gelation kinetics may be evaluated to identify optimized pH for peptide compositions as described herein.

Figure 24:
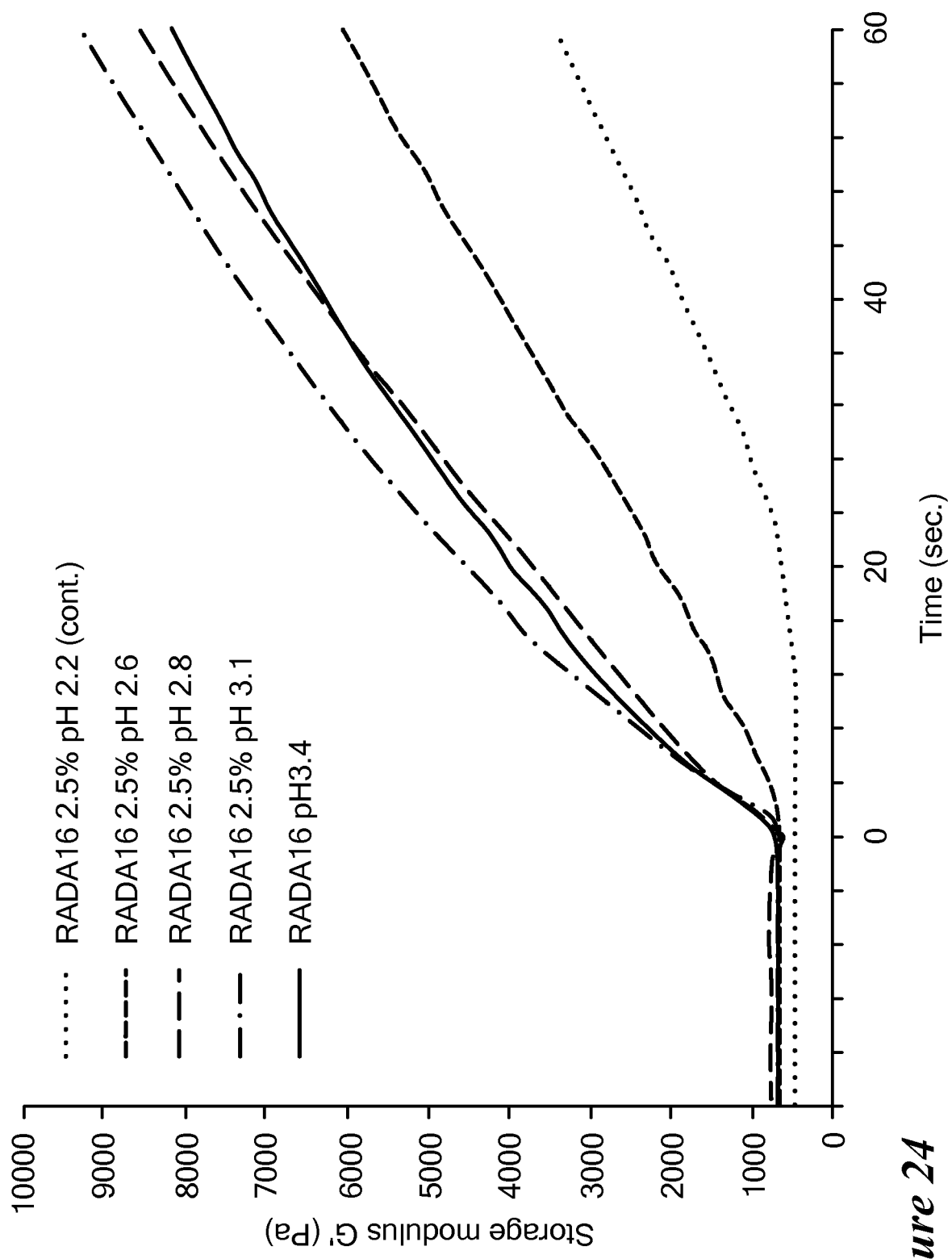
FIGS. 24 and 25 show storage modulus measurement as a function of time.
Figure 25:
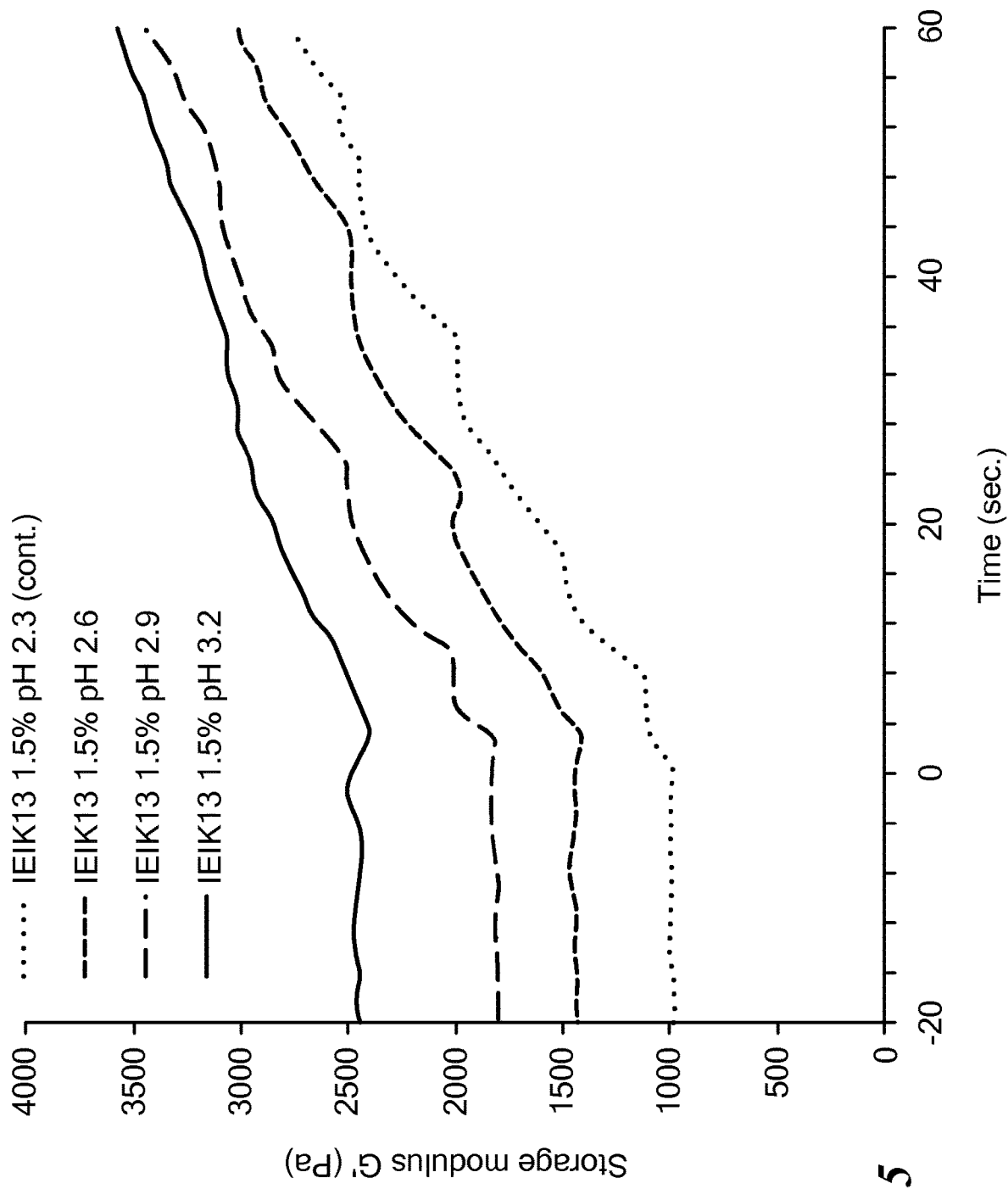
Figure 26:
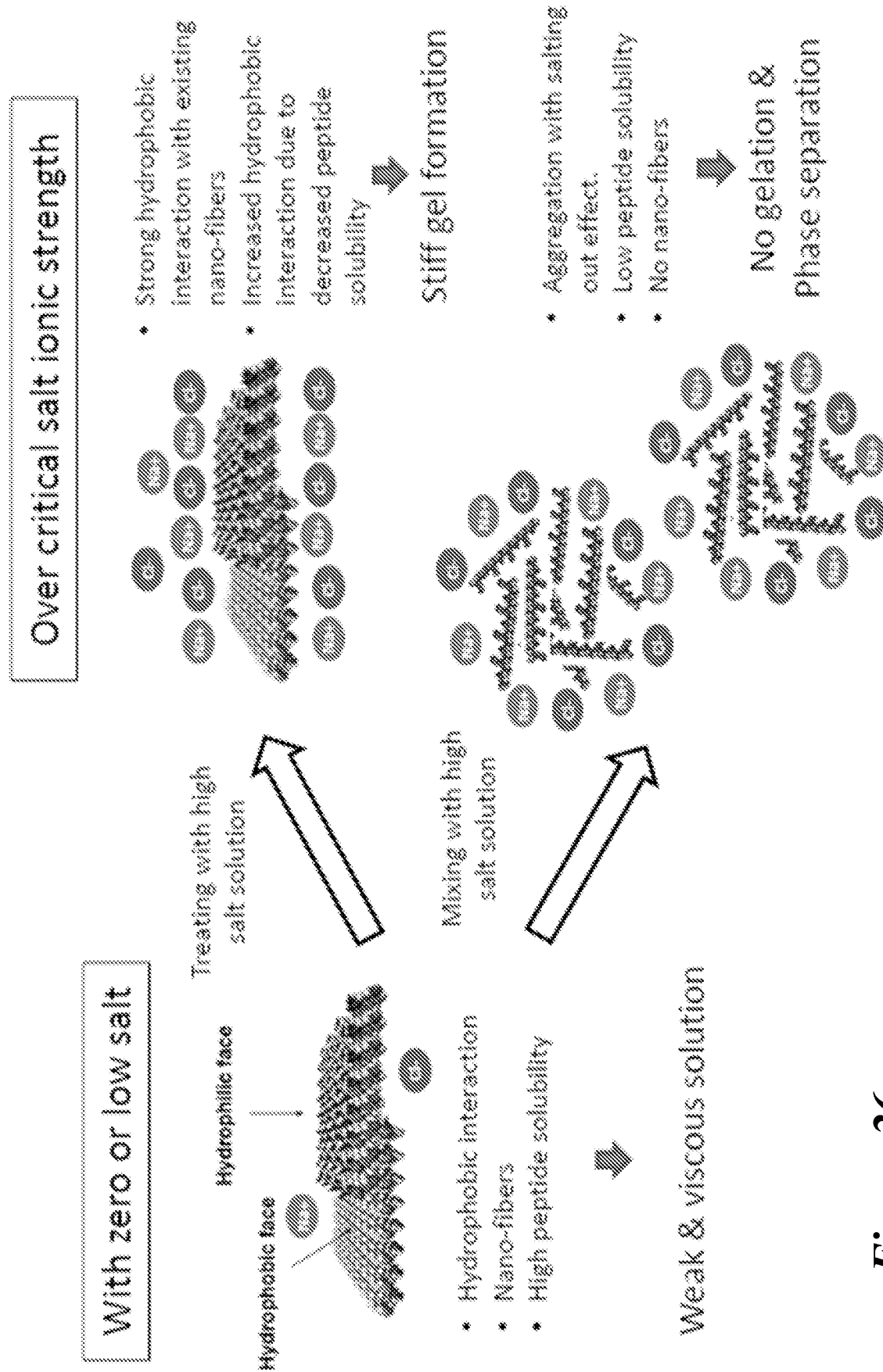
FIG. 26 illustrates nanostructures and/or reassembly of peptides at low salt conditions or high salt conditions (i.e. over critical ionic strength). The application methods of salt solutions (treatment or mixing) may change the nanostructures. While treating peptides with a salt solution may form stiff gel, mixing a salt solution to peptides may cause phase separation.

In some embodiment, peptide compositions may gel faster at higher pH. For example, as described herein IEIK13 (SEQ ID NO:3) compositions without pH adjustment show immediate storage modulus increase, while RADA16 (SEQ ID NO:1) compositions without pH adjustment (pH 2.2) do not show storage modulus increase for first 13 seconds. With pH adjustment, both IEIK13 (SEQ ID NO:3) and RADA16 (SEQ ID NO:1) show immediate storage modulus increase due to fast gelation, as shown in FIGS. 24 and 25.

Ionic Strength

The present disclosure demonstrates that ionic strength may change rheological properties of peptide compositions. Increasing the ionic strength of peptide compositions may generally improve mechanical properties for various clinical applications. Effects of ionic strength on the properties of peptide compositions may be evaluated, e.g., as described herein, to identify optimized ionic strengths for peptide compositions as described herein.

In some embodiments, at ionic strength within the range of about 0.0001 M to about 1.5 M, stiffness, viscosity, and/or gelation kinetics of peptide compositions may be increased. In some embodiments, peptide compositions may be controlled with ionic strength.

In accordance with one or more embodiments, ionic strengths of peptide compositions may be adjusted with one or more common salts including but not limited to NaCl, KCl, $MgCl_2$, $CaCl_2$ and $CaSO_4$. Common salts are composed of cations and anions. In some embodiments, cations may be selected from the group comprising of ammonium, calcium, iron, magnesium, potassium, pyridinium, quaternary ammonium, and sodium. In some embodiments, anions may be selected from the group comprising of acetate, carbonate, chloride, citrate, cyanide, fluoride, nitrate, and phosphate.

In accordance with one or more embodiments, when ionic strength approaches an optimal level (e.g., highest stiffness), addition of one or more salt or salt solutions may be carefully regulated. In some embodiments, pure water may be added if ionic strength is higher than desired. Addition of one or more salt or salt solutions may be regulated to adjust its osmolality to be hypotonic, isotonic or hypertonic depending on its applications.

In some embodiments, to adjust ionic strengths of certain peptide compositions by way of example, certain salt buffer solutions, for example, NaCl, KCl, $MgCl_2$, $CaCl_2$ and DPBS (Dulbecco's Phosphate-Buffered Saline, 10×) may be added.

In some embodiments, provided compositions include one or more salts, the identity and/or concentration of which maintain the composition at a critical ionic strength below that at which material precipitation of the peptide is observed. In some embodiments, material precipitation is considered to have occurred when a liquid composition is cloudy (e.g., as assessed by visual inspection). Thus, in some embodiments, provided compositions are not cloudy, and have lower ionic strengths than otherwise comparable compositions (e.g., of the same peptide at the same concentration) that are cloudy.

In some embodiments, provided compositions are characterized by an elevated ionic strength relative to that of an appropriate reference composition (e.g., a composition of the same peptide at the same concentration and pH but with different salt or different concentration of the same salt). In some embodiments, provided compositions are character-ized by ionic strength close to or at physiological strength. In some embodiments, compositions as described herein are characterized by greater rheological stiffness and/or improved gelation properties as compared with an appropriate reference composition of different ionic strength. In some embodiments, provided compositions are suitable for use in a broader range of applications that are corresponding reference compositions of different (e.g., lower) ionic strength.

In accordance with certain particular embodiments, peptide compositions comprising IEIK13 (SEQ ID NO:3), KLD12 (SEQ ID NO:2), or RADA16 (SEQ ID NO:1) in a salt solution are provided, which compositions have an ionic strength different from that a reference composition of the relevant peptide dissolved in water and show one or more improved material (e.g., rheological) properties relative to that reference composition. In some embodiments, the provided compositions are stiffer than the relevant reference compositions. In some embodiments, the provided compositions have elevated ionic strengths relative to the reference compositions, but still have an ionic strength below their critical salt points.

TABLE 10

Visual observation of solubility of certain self-assembling peptide compositions with selected salts

| | RADA16 (SEQ ID NO: 1) | | KLD12 (SEQ ID NO: 2) | | IEIK13 (SEQ ID NO: 3) | |
|---|---|---|---|---|---|---|
| Salts | Conc. at cloud point (M) | Ionic strength at cloud point (M) | Conc. at cloud point (M) | Ionic strength at cloud point (M) | Conc. at cloud point (M) | Ionic strength at cloud point (M) |
| NaCl | 0.85~0.9 | 0.85~0.9 | 0.25~0.3 | 0.25~0.3 | 0.025~0.03 | 0.025~0.03 |
| KCl | 1.0~1.05 | 1.0~1.05 | 0.25~0.3 | 0.25~0.3 | 0.03~0.035 | 0.03~0.035 |
| $MgCl_2$ | 0.383~0.4 | 1.15~1.2 | 0.117~0.133 | 0.35~0.4 | 0.0133~0.015 | 0.04~0.045 |
| $CaCl_2$ | 0.383~0.4 | 1.15~1.2 | 0.117~0.133 | 0.35~0.4 | 0.0133~0.015 | 0.04~0.045 |
| DPBS (pH 3.2) | 0.9~0.95 | 0.9~0.95 | — | — | — | — |

Without wishing to be bound by any particular theory, the present disclosure proposes that properties of peptide compositions with increased ionic strength may be related to solubility of peptides. Solubility of self-assembling peptides at pH level about 2 to 4 is mostly high enough to make clear and homogeneous peptide compositions. Increased ionic strength around peptide chains decreases solubility of peptides. When solubility of peptides is low so that compositions become cloudy, this status may be called as a critical point. When increased ionic strength is lower than its critical point but close to it, peptides may induce stronger hydrophobic interactions increasing stiffness. When peptide solubility is decreased below its critical point (i.e. high ionic strength), peptide compositions may be translucent or opaque (i.e. it is above its cloud point), and may be precipitated (i.e. phase separation). Peptides may not form nano-fibers that make clear and viscous solutions. Random hydrophobic interactions may be dominant over hydrophobic interactions that create self-assembled nano fibers at high ionic strength due to salting out effect. Random intra- and/or inter-molecular aggregates may cause phase separations.

In accordance with one or more embodiments, critical ionic strengths may vary depending on salt and peptide identities. The relationship between solubility and salt concentration can be expressed by following Cohen equation:

$$\log S = B - KI$$

where S is a solubility of a peptide, B is a peptide-specific constant, K is a salt-specific constant, and I is an ionic strength of salts. B is related to pH, and temperature. K is related to pH.

In some embodiments, solubility of peptides may be governed by salting out constant K and ionic strength I, when temperature and pH are constant (i.e. B is constant). The higher K and I result in the lower peptide solubility. At constant pH and temperature, K is decided by ion identities in salts. Overall, the order of constant K among the four salts is $NaCl>KCl>MgCl_2=CaCl_2$.

In accordance with one or more embodiments, solubility of peptides may be determined by amino acid sequence (e.g., by compositions of hydrophilic and hydrophobic amino acid residues in the peptide). Peptides with relatively high hydrophobic amino acid contents (e.g. IEIK13 (SEQ ID NO:3)) typically have low solubility in aqueous solvents. Such peptides often are characterized by strong hydrophobic interactions between self-assembled peptide chains, resulting in high stiffness. As demonstrated herein, compositions of such peptides may show dramatic stiffness increases with addition of a small amount of salt. By contrast, peptides with relatively low hydrophobic amino acid contents (e.g. RADA16 (SEQ ID NO:1)) have high solubility in aqueous solvents. These peptides typically have weak hydrophobic interactions between self-assembled peptides, resulting in low stiffness. Stiffness of compositions of such peptides does not increase significantly even with addition of a large amount of salt. Consistent with this model, the present disclosure demonstrates an order of critical ionic strength (e.g. when the composition becomes cloudy) among three particular exemplified peptides that parallels relative hydrophobicity: RADA16 (SEQ ID NO:1) (0.9~1.2 M)>KLD12 (SEQ ID NO:2) (0.3~0.4 M)>IEIK13 (SEQ ID NO:3) (0.03~0.04 M).

In accordance with one or more embodiments, ionic strength of a peptide composition may impact its gelation kinetics. In some embodiment, elevated ionic strengths may accelerate gelation of peptide compositions. The required ionic strengths for gelation may depend on salt and/or peptide identities. For example, when RADA16 (SEQ ID NO:1), KLD12 (SEQ ID NO:2), and IEIK13 (SEQ ID NO:3) peptides were exposed to saline buffer (i.e. 0.15 M NaCl, comparable to the isotonic body fluid), only gelation of IEIK13 (SEQ ID NO:3) was initiated. RADA16 (SEQ ID NO:1) and KLD12 (SEQ ID NO:2) showed no or negligible gelation. These findings may reflect decreased solubility of peptides with elevated ionic strength. IEIK13 (SEQ ID NO:3) is more sensitive to ionic strength than RADA16 (SEQ ID NO:1) and KLD12 (SEQ ID NO:2) as described above.

In some embodiments, ionic strength of a peptide composition may impact its recovery characteristics, for example after mixing and/or agitation processes break down initially-formed assemblies (e.g., nano fibers) that result from (typically hydrophobic) peptide-peptide interactions.

Combined pH and Salt Effects

The present disclosure demonstrates that simultaneous adjustment of pH and ionic strength (e.g., via exposure to physiological conditions) can alter rheological properties of peptide compositions. For example, as described herein, increased pH level and ionic strength due to inclusion of cell culture medium in provided peptide compositions can impact various properties (e.g., rheological properties) of such compositions.

In some embodiments, stiffness, viscosity and/or gelation kinetics of peptide compositions may be increased under physiological conditions. In some embodiments, properties of peptide compositions may be controlled with the combination of pH and ionic strength.

Without wishing to be bound by any particular theory, the present disclosure proposes that there are two main intermolecular interactions that relate to stiffness of peptide compositions: hydrophobic interactions and charge-charge interactions.

First, hydrophobic interactions and repulsive electrostatic interactions are the main driving force for forming viscous solutions through β-sheet nanofiber formation at low pH. These interactions are predicted to be significant at low pH, where a majority of aspartic acid and glutamic acids are protonated without negative charges and a majority of arginine and lysine are positively charged. The peptide molecules are self-assembled to form nano-fibers due to hydrophobic interactions, while the surfaces of the nano-fibers are hydrated due to repulsive electrostatic interactions between the peptide molecules.

In some embodiments, stiffness of peptide compositions around pH levels of about 2 to about 3 should be mainly related to their hydrophobicity. IEIK13 (SEQ ID NO:3) has seven isoleucine groups (strong hydrophobic group), KLD12 (SEQ ID NO:2) has six leucine groups (strong hydrophobic group), and RADA16 (SEQ ID NO:1) has eight alanine groups (weak hydrophobic group). IEIK13 (SEQ ID NO:3) has higher storage modulus than KLD12 (SEQ ID NO:2) and RADA16 (SEQ ID NO:1) at the same pH and concentration.

Figure 17A:
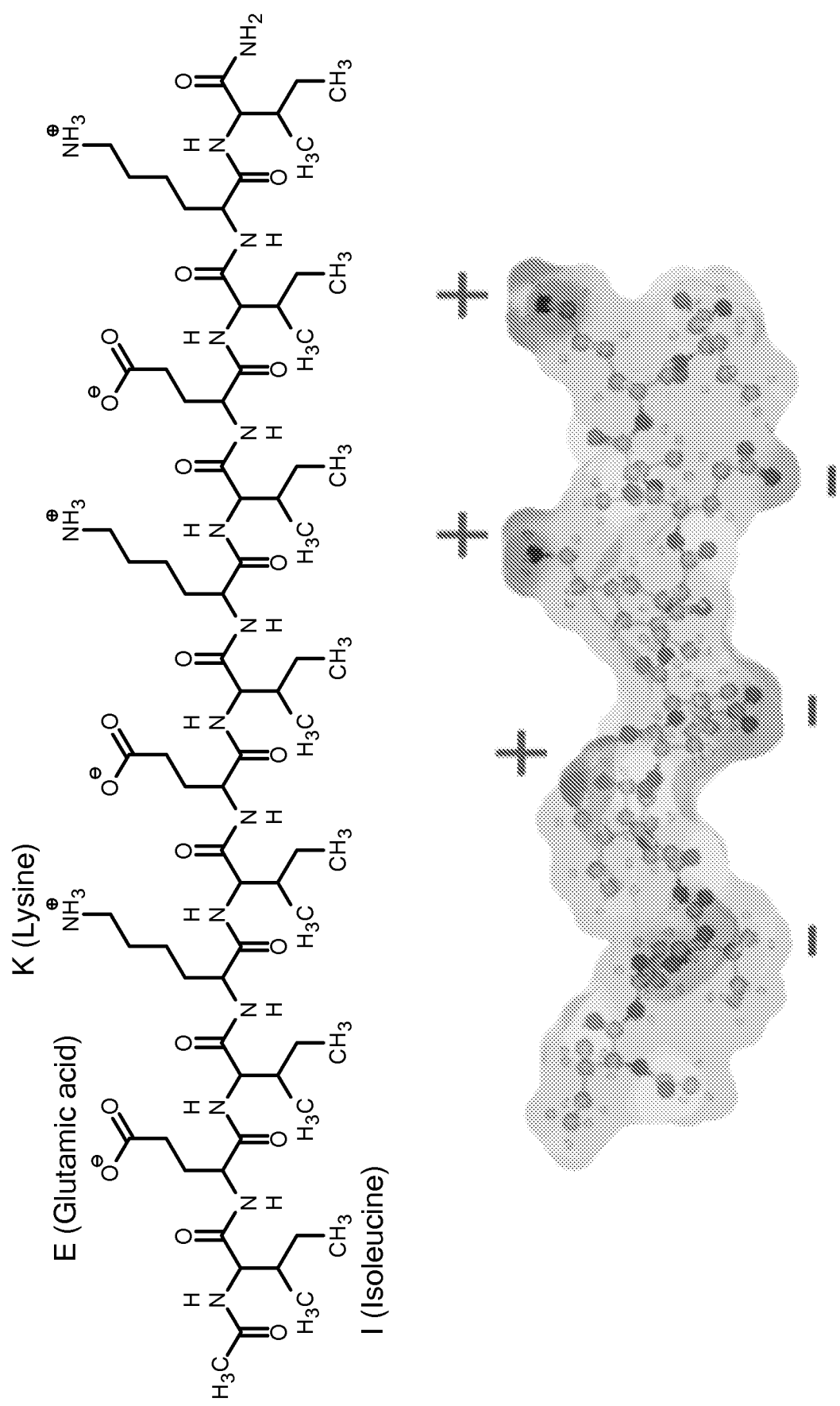
FIG. 17A illustrates a structure of IEIK13 (SEQ ID NO:3).

As shown in FIG. 17B, when IEIK13 (SEQ ID NO:3) molecules in an aqueous solution were treated with simulated body fluid, for example, DMEM, their fibrous structure became thicker. The thicker fibrous structure may occur due to increased hydrophobic interactions at physiological pH and osmolality between neighboring nano fibers.

Hydrophobic interactions may induce nanofiber formation in an aqueous environment, creating a viscous composition. After application of high shear stress (i.e. reduced viscosity and stiffness), peptides may also reform nanofibers to recover their properties. Thus, the peptides show thixotropic property at pH 2-3. Peptide compositions slowly recover their original properties once the applied shear stress is removed.

Second, attractive charge-charge interactions may occur simultaneously with existing hydrophobic interactions at physiological conditions. When the pH around peptide molecules changes from acidic to neutral, existing hydrophobic interactions may not break down. Negatively-charged groups and positively-charged groups induce additional attractive charge-charge intermolecular interactions, so that peptide compositions may be stiffer as demonstrated in FIG. 7.

Figure 7:
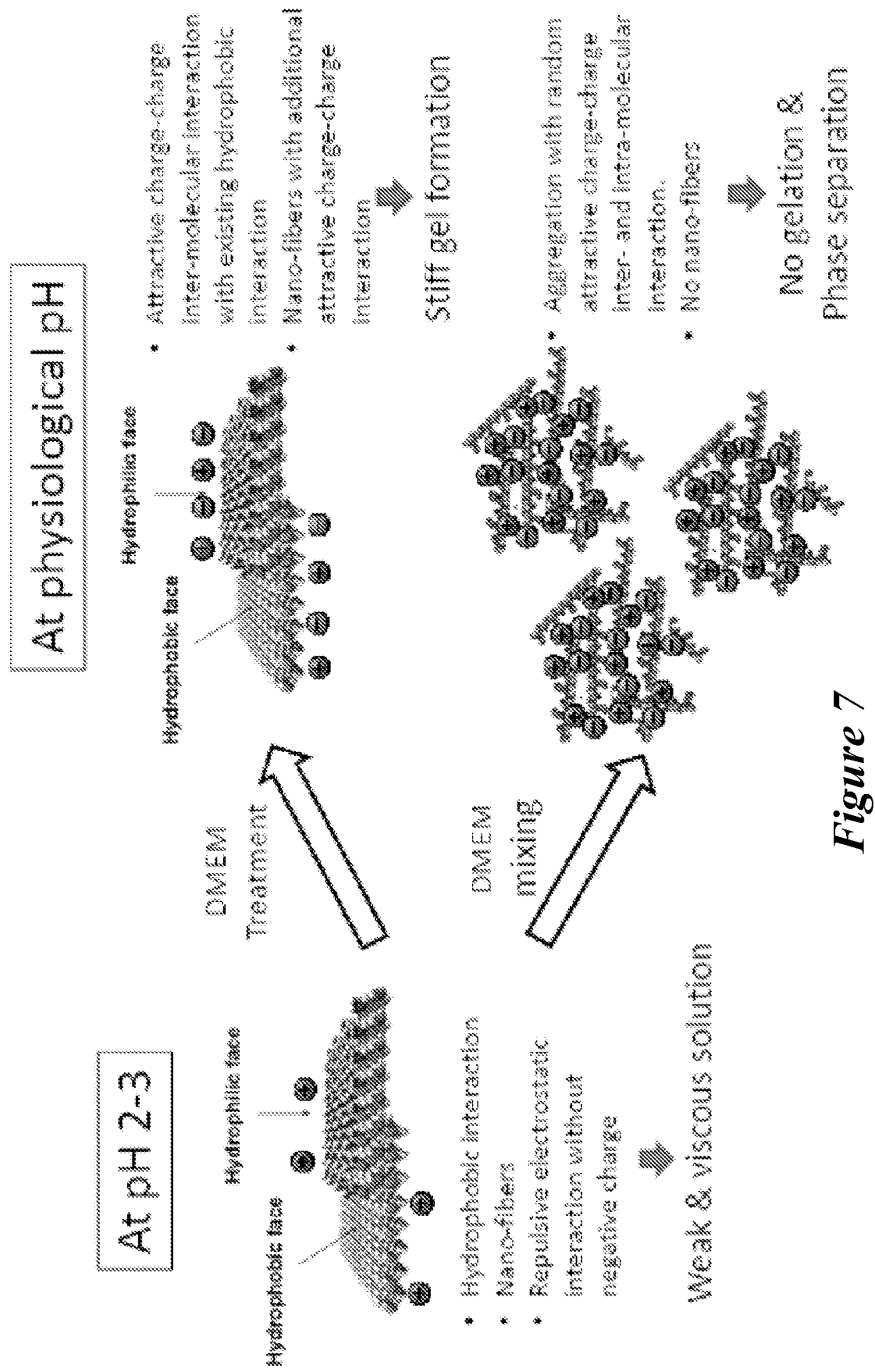
FIG. 7 illustrates nanostructures of RADA16 (SEQ ID NO:1), KLD12 (SEQ ID NO:2), and IEIK13 (SEQ ID NO:3) compositions at pH 2-3, and at physiological pH (DMEM). While the DMEM treatment may form stiff compositions, mixing DMEM may precipitate peptides.
Figure 8:
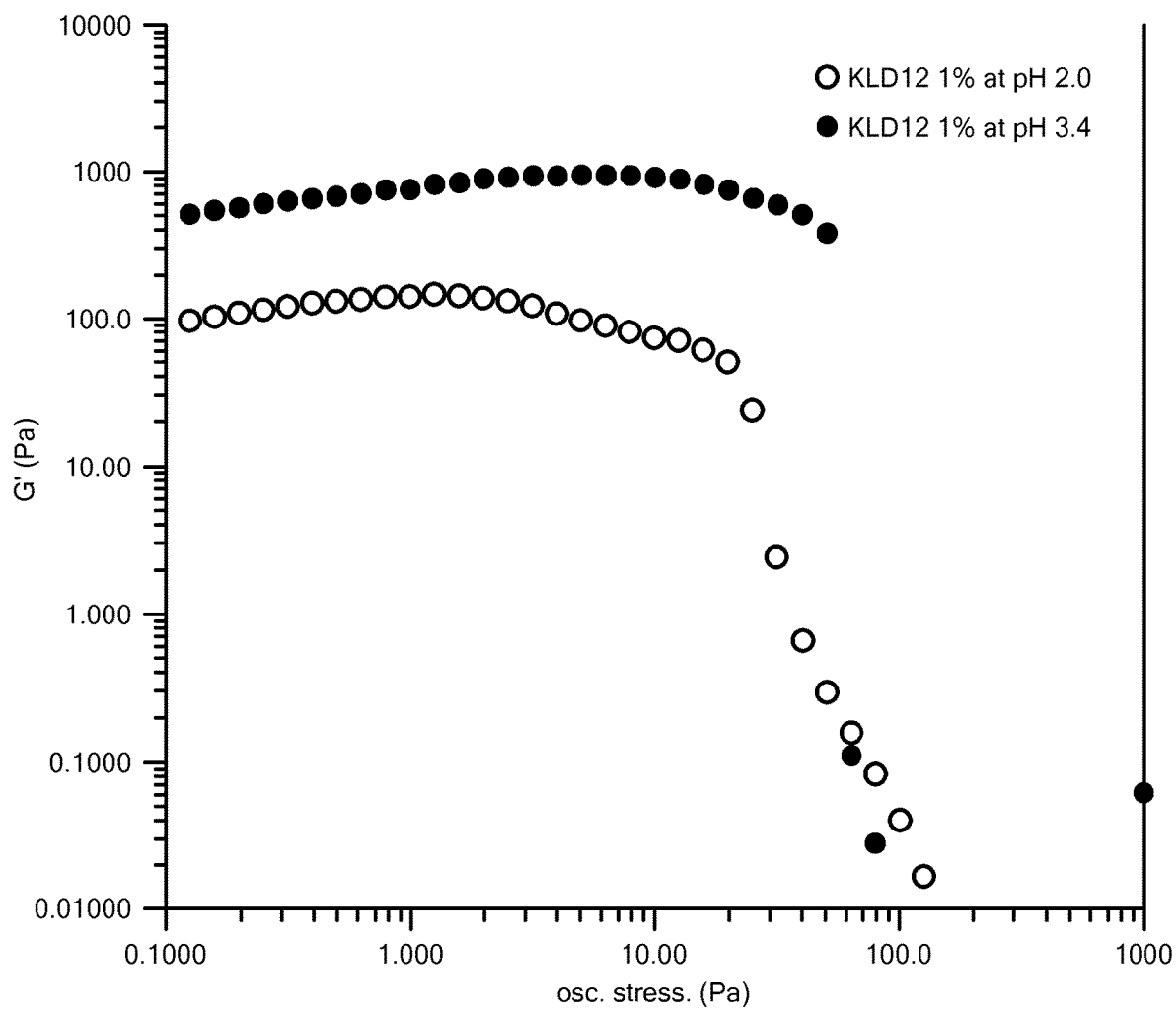
FIG. 8 shows exemplary stress sweep tests at 10 rad/s of 1% KLD12 (SEQ ID NO:2) compositions at pH=2.0 and 3.4.
Figure 9:
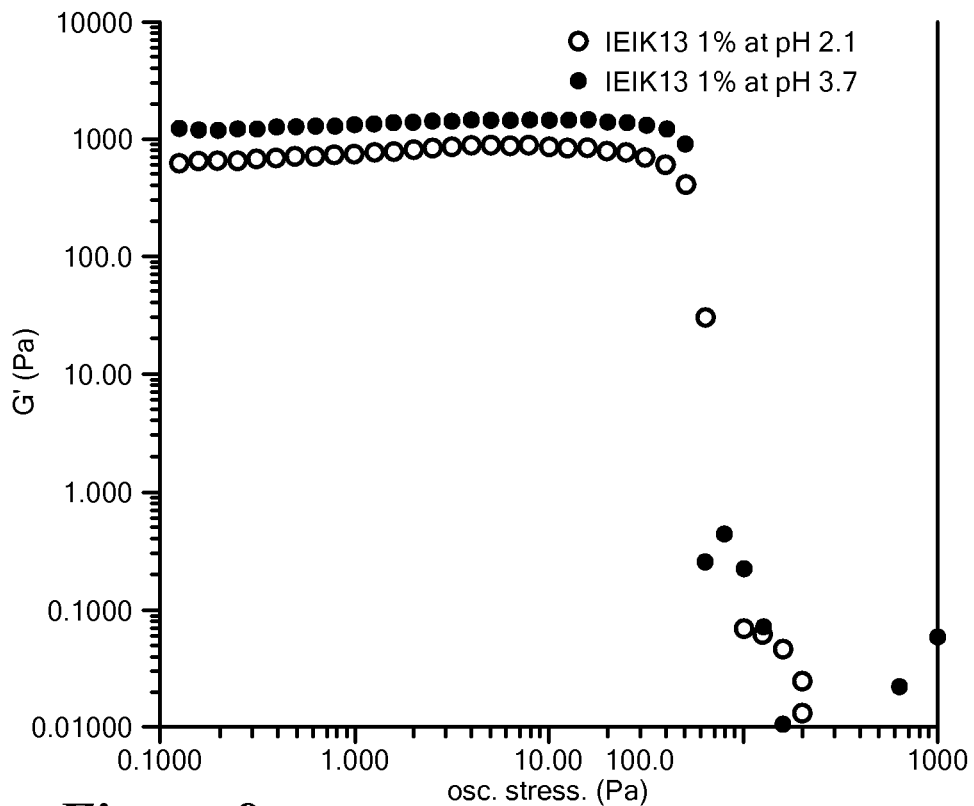
FIG. 9 shows exemplary stress sweep tests at 10 rad/s of 1% IEIK13 (SEQ ID NO:3) compositions at pH=2.1 and 3.7.
Figure 10:
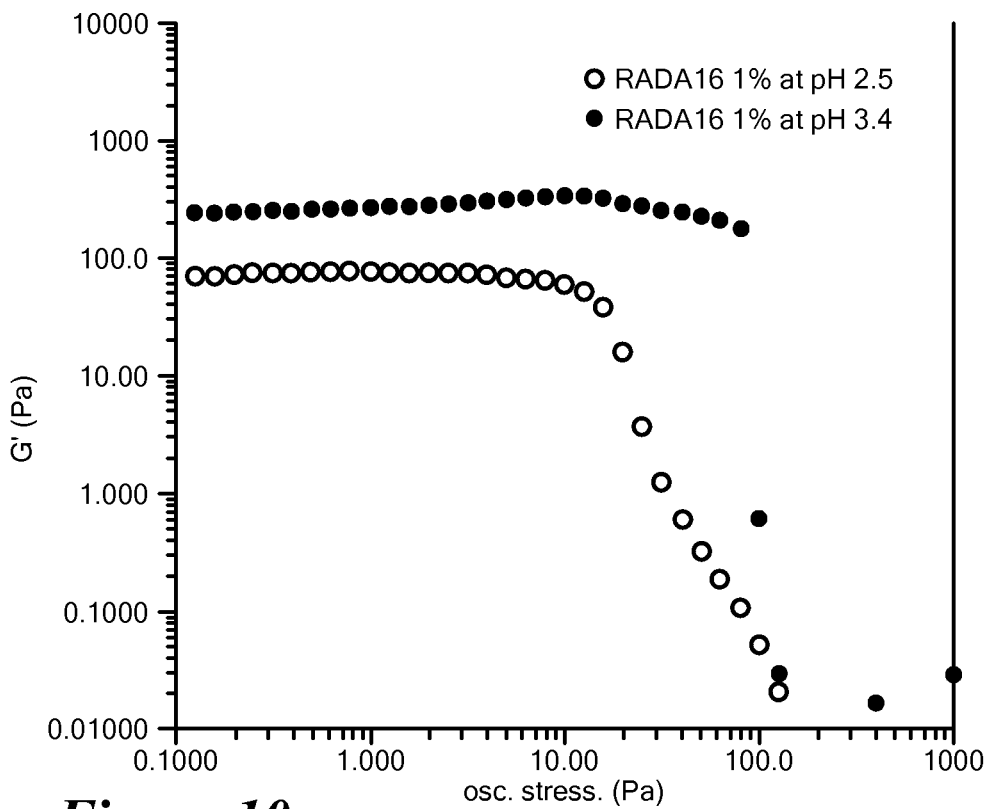
FIG. 10 shows exemplary stress sweep tests at 10 rad/s of 1% RADA16 (SEQ ID NO:1) compositions at pH=2.5 and 3.4. Storage moduli of peptide compositions were increased with pH increase.
Figure 11A:
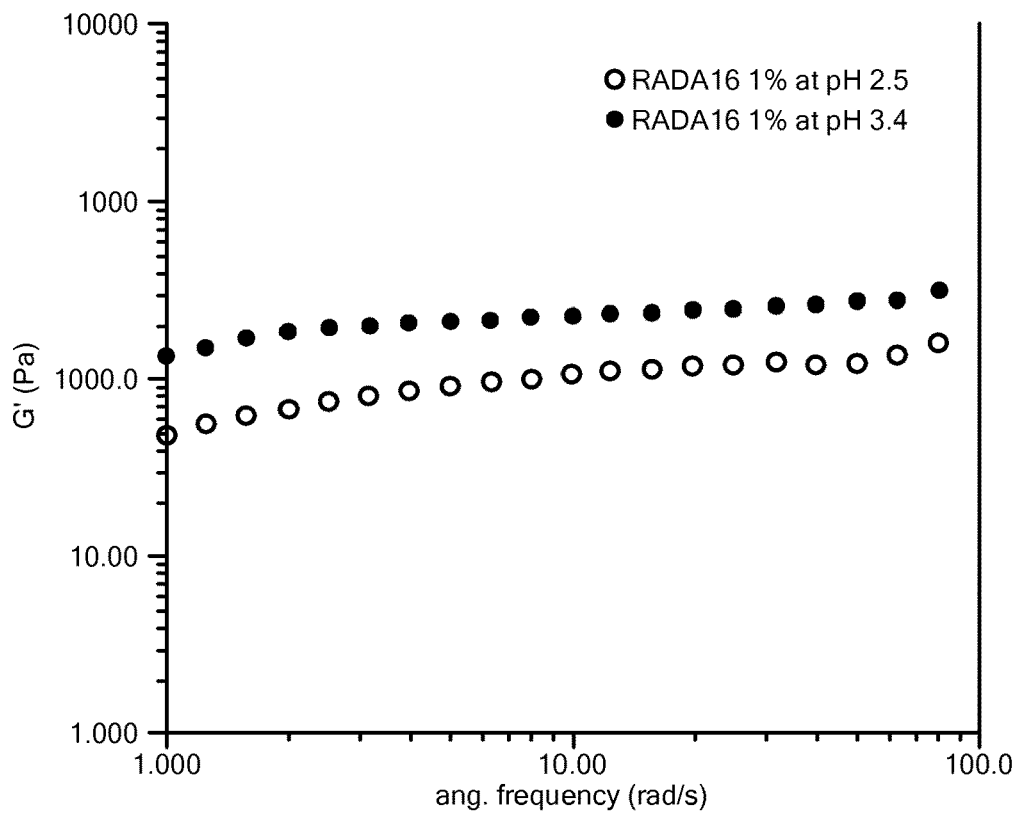
FIGS. 11A and 11B show exemplary frequency sweep tests of RADA16 (SEQ ID NO:1) at 1 Pa.
Figure 11B:
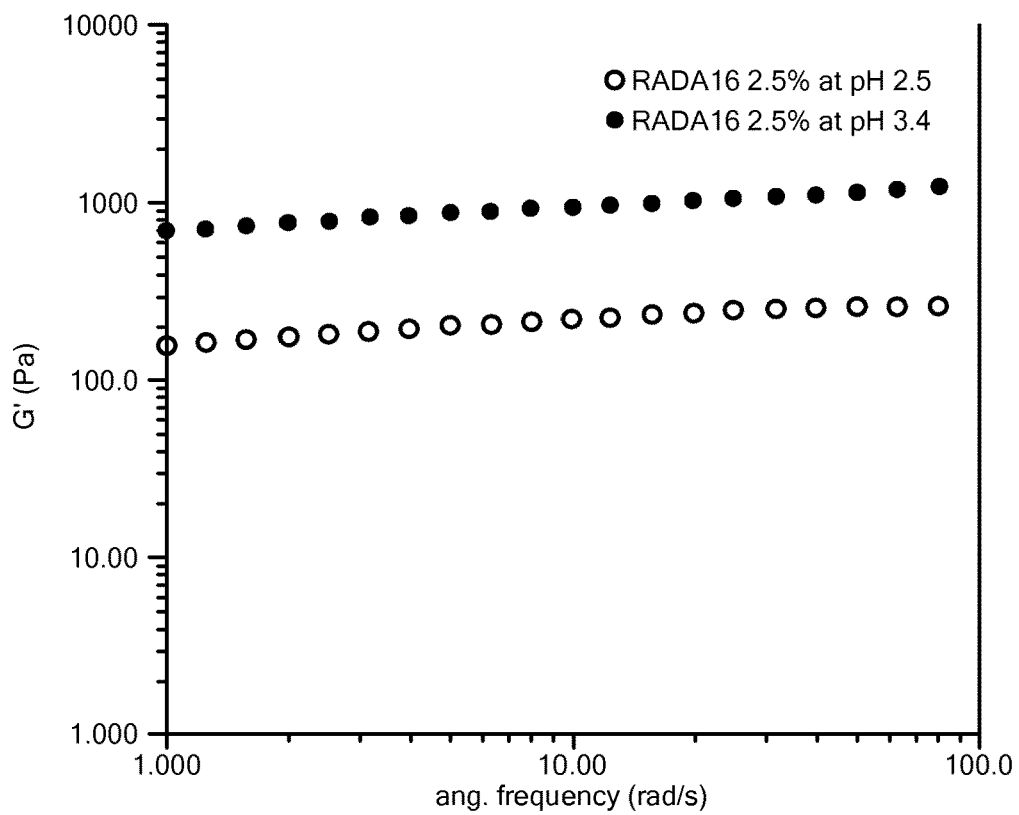
Figure 12:
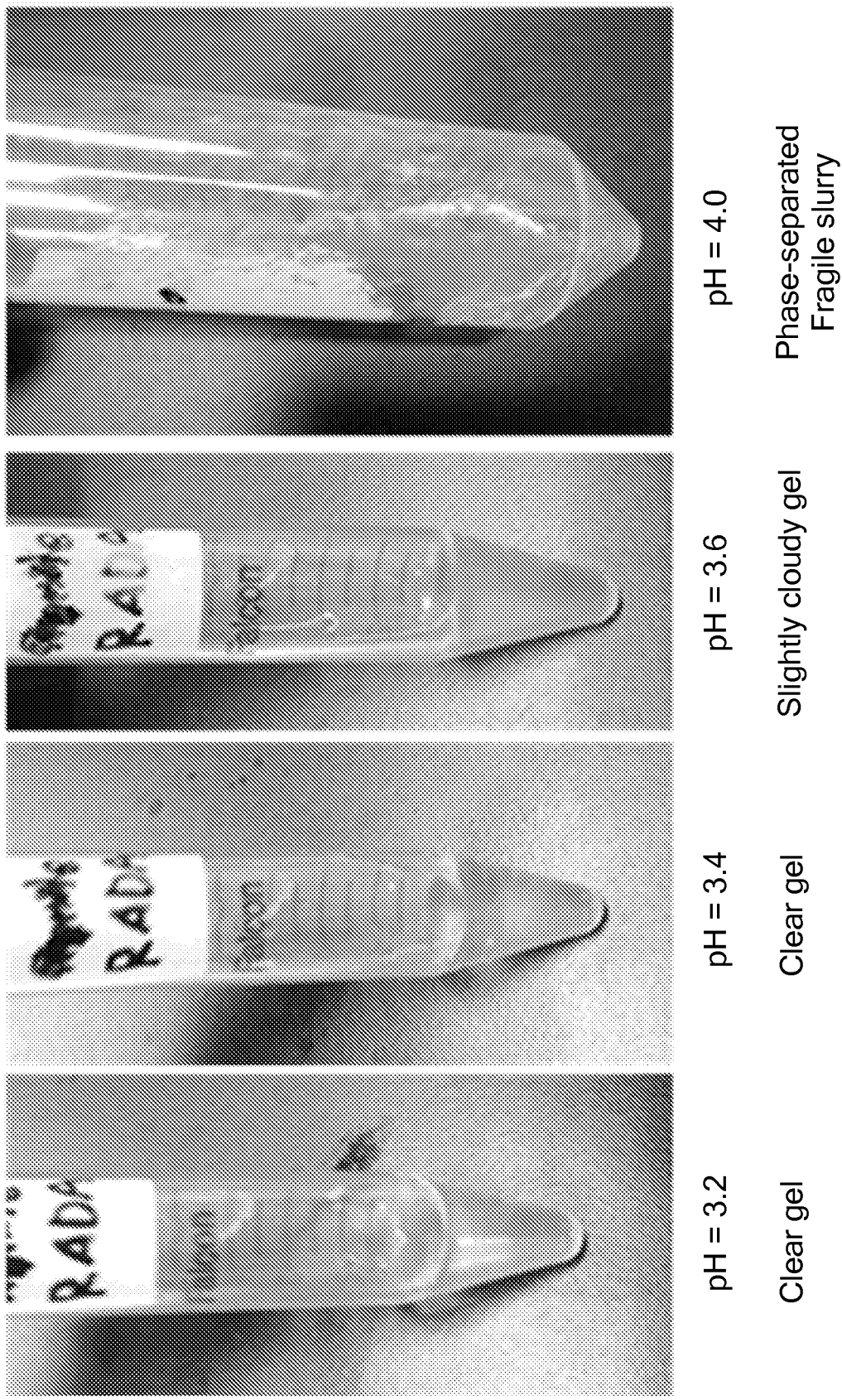
FIG. 12 is pictures of 2.5% RADA16 (SEQ ID NO:1) at pH 3.2, 3.4, 3.6 and 4.0. The composition was clear when pH level was about 3.5, and slightly cloudy at pH=3.6. The composition was precipitated at pH=4.0.
Figure 13:
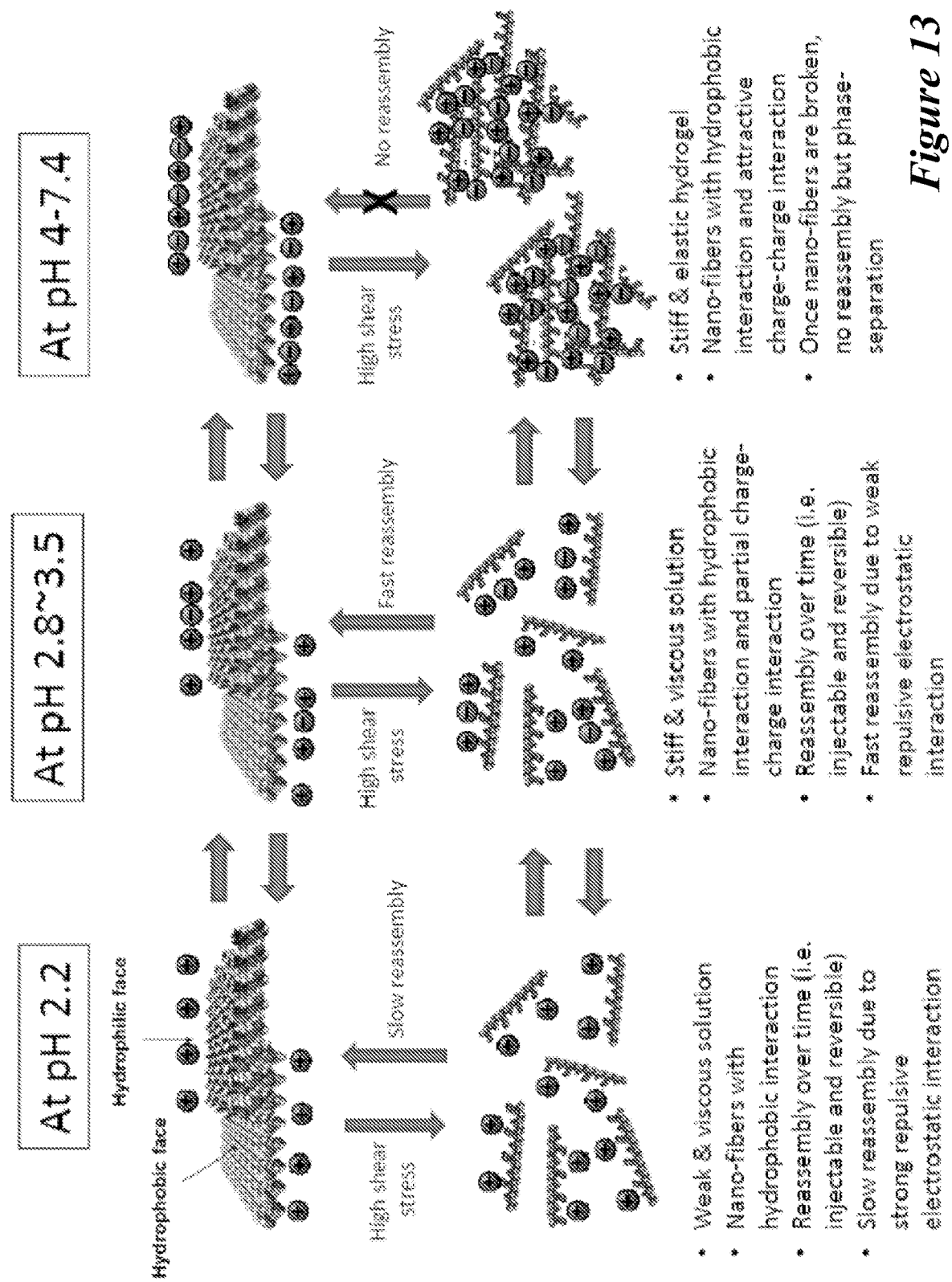
FIG. 13 illustrates nanostructures and/or reassembly of RADA16 (SEQ ID NO:1), KLD12 (SEQ ID NO:2), and IEIK13 (SEQ ID NO:3) at different pH levels, with or without shear stress. Dominant interactions may be determined by pH and shear stress.

However, when peptide assemblies at a physiological condition are exposed to high shear stress, the peptide assemblies break down to peptide aggregates. This is an irreversible process, as illustrated in FIG. 7.

For example, when 0.5 mL of DMEM was mixed with 0.5 mL of 2% RADA16 (SEQ ID NO:1) by pipetting several times, RADA16 (SEQ ID NO:1) did not form clear and viscous peptide assemblies (i.e. cloudy and runny emulsions). When the mixture was centrifuged at 2500 rpm for 5 min, phase separation of cloudy RADA16 (SEQ ID NO:1) precipitated from the mixture. In this case, the peptide assemblies (i.e. initially were formed via hydrophobic interactions) were likely broken down during the mixing process. Attractive charge-charge interactions were dominant over hydrophobic interactions, which induce formation of random intra- and inter-molecular aggregates. The phase separation is illustrated in FIG. 7.

In accordance with one or more embodiments, IEIK13 (SEQ ID NO:3), KLD12 (SEQ ID NO:2), or RADA16 (SEQ ID NO:1) may be dissolved in salt buffer (e.g. NaCl), and their pH may be elevated with alkali salt buffer (e.g. NaOH). Their salt ionic strengths may be under their critical salt points. Their pH may be about 2.5 to about 4.0. The compositions may have increased stiffness and viscosity relative to an appropriate reference composition of the same peptide at the same concentration.

In some embodiments, physiological conditions (e.g., elevated pH and salt ionic strength) may accelerate gelation of peptide compositions. Accelerated gelation of IEIK13 (SEQ ID NO:3) under a physiological condition may be related to two driving forces i.e. increased pH and ionic strength. Accelerate gelation of RADA16 (SEQ ID NO:1) under a physiological condition may have only one driving force i.e. increased pH. In some embodiments, accelerated gelation of peptide compositions with body fluid may generally improve its function and responding time for various clinical applications.

Cell Compatibility

In accordance with one or more embodiments, provided peptide compositions are generally associated with high cell viability.

In some embodiments, KLD12 (SEQ ID NO:2) and IEIK13 (SEQ ID NO:3) may have similar or higher cell viabilities compared to RADA16 (SEQ ID NO:1). The order of overall cell viability among these peptide compositions was KLD12 (SEQ ID NO:2)>IEIK13 (SEQ ID NO:3) >RADA16 (SEQ ID NO:1). In some embodiments, peptide compositions may have cell viabilities higher than 80% when their concentrations are about or less than 0.75%. In some embodiments, cell viabilities may be decreased when peptide concentrations are higher than 0.75%.

Form

In some embodiments, peptide compositions in accordance with the present invention are in the form of a dry powder, a solution, a gel (e.g., a hydrogel), or any combination thereof.

In some embodiments, a dry powder composition comprises peptide in an appropriate amount to result in a solution of desired concentration upon addition of a selected volume of solvent (e.g., aqueous solvent, optionally including one or more salts and/or one or more pH-adjusting agents). In some embodiments, a dry powder composition comprise peptide and salt of appropriate types and relative amounts to result in a solution of desired peptide concentration and ionic strength as described herein upon addition of a selected volume of solvent (e.g., aqueous solvent, optionally including one or more additional salts and/or one or more pH-adjusting agents). In some embodiments, a dry powder composition comprise peptide and pH adjusting agent of appropriate types and relative amounts to result in a solution of desired peptide concentration and pH as described herein upon addition of a selected volume of solvent (e.g., aqueous solvent, optionally including one or more salts and/or one or more additional pH-adjusting agents). In some embodiments, a dry powder composition comprises peptide, salt, and pH adjusting agent of appropriate types and relative amounts to result in a solution of desired peptide concentration, pH, and/or ionic strength as described herein upon addition of a selected volume of solvent (e.g., aqueous solvent, optionally including one or more additional salts and/or one or more additional pH-adjusting agents).

In some embodiments, a provided composition is housed in a container (e.g., a syringe, vial, well, etc.). In some embodiments, the container is a graduated container in that it includes volume indications. In some embodiments, the container is adapted for connection to a delivery device such as a cannula or syringe. In some embodiments, the container is sealed in a manner (e.g., a penetrable covering) that permits addition and/or removal of flowable (e.g., liquid) material without removal of the seal.

Applications

In some embodiments, the present disclosure provides a system for selecting peptide compositions for use in particular applications. Effects of peptide identity, peptide concentration, pH, salt identity and/or salt concentration, as described herein, can impact characteristics, and therefore utility of particular peptide compositions for certain applications.

To give but a few examples, in general, peptide compositions with higher stiffness are more suited to applications characterized by hemostasis, tissue plugs, anti-adhesion, or certain tissue regeneration. Peptide compositions with more rapid gelation times may be particularly suited to certain tissue plug applications such as, for example, hemostasis, tissue plug, anti-adhesion, or drug delivery, vascular plug, for which gelation times below about 1 minute to about 1 hour are typically required or preferred. Peptide compositions with more rapid recovery times may be particularly suited to hemostasis, tissue plug, or vascular plug.

As noted herein, self-assembling peptide compositions have provide to be extremely useful in a variety of in vivo and in vitro contexts, including for example as cell scaffolds, barriers to liquid movement, hemostats, void fillers, and more. Different such compositions, as described herein, may be more useful in different contexts.

For example, contexts that involve administration of a peptide composition during surgery (e.g., as a hemostat) may benefit from gelation kinetics that permit the composition to remain substantially liquid for a period of time appropriate for administration to the surgical site, followed by rapid gelation to form a stable, preferably clear and relatively stiff gel through which surgical manipulations can readily proceed.

To give specific examples, as described herein, in some embodiments, IEIK13 (SEQ ID NO:3) compositions may be particularly useful in a variety of biomedical applications, for example that require certain stiffness and fast gelation. The present disclosure demonstrates that certain IEIK13 (SEQ ID NO:3) compositions are characterized by relatively high stiffness and/or rapid recovery rates after application of high shear stress (e.g. the fastest self-assembly). Also, the present disclosure demonstrates that certain IEIK13 (SEQ ID NO:3) compositions may show particularly useful (e.g., high) stiffness when contacted with a physiological medium.

The present disclosure also demonstrates that certain KLD12 (SEQ ID NO:2) compositions may be particularly useful, for example, when easy injection is required together with high final stiffness. In some embodiments, self-assembled nano fibers of KLD12 (SEQ ID NO:2) may be disassembled with high shear stress, and then slowly assemble back.

The present disclosure also demonstrates that certain KLD12 (SEQ ID NO:2) compositions may be particularly useful when high cell viability is required. In some embodiments, concentrations of KLD12 (SEQ ID NO:2) may be increased to have a required stiffness for a certain application.

EXEMPLIFICATION

Example 1: Optical Clarity of Certain Reference Peptide Compositions

The present Example illustrates optical clarity and phase stability (i.e., absence of phase separation) of certain reference peptide compositions in which the indicated peptide was dissolved in water. In some embodiments, optical clarity (and/or phase stability) of provided peptide compositions is assessed relative to that of such reference compositions. In some embodiments, provided compositions of a particular peptide at a particular concentration show optical clarity and/or phase stability at least as good as that of a reference composition of the same peptide at the same composition dissolved in water.

As can be seen with reference to Table 1, various reference peptide compositions were prepared that showed optical clarity (and also phase stability) across a range of peptide concentrations. In particular, peptide compositions at concentrations of 0.05%, 0.1%, 0.5%, 1%, 1.5%, 2%, 2.5% or more showed a clear optical character and absence of phase separation.

TABLE 1

Appearance of peptides

| Peptide identity | Peptide concentration | Appearance |
|---|---|---|
| IEIK13 (SEQ ID NO: 3) | Up to 2.5% | Clear |
| | Above about 2.5%, solutions may become too viscous to be useful | No phase separation |
| KLD12 (SEQ ID NO: 2) | Up to at least 2.5% | Clear |
| | Higher concentrations likely possible | No phase separation |

Example 2: Rheological Properties of Peptide Compositions as a Function of Concentration The present Example describes effects of peptide concentration on rheological properties of certain peptide compositions. In some embodiments, rheological properties may have a linear relationship with peptide concentration.

In some embodiments, peptide compositions with a specific desired stiffness may be formulated to have a particular peptide concentration determined using a mathematical model (i.e., the modulus trend-line equation). A formulation chart of peptide compositions may relate their concentrations in deionized water to their specific storage moduli, for example as is presented below in Table 3A. From such a chart, one skilled in the art may formulate a peptide composition with desired rheological properties by selecting a particular peptide and an appropriate peptide concentration so that the formulated composition has a desired stiffness.

For example, as described herein, in general, the order of rheological strength of peptide compositions containing RADA16 (SEQ ID NO:1), KLD12 (SEQ ID NO:2), or IEIK13 (SEQ ID NO:3) peptides is demonstrated to be IEIK13 (SEQ ID NO:3)>KLD12 (SEQ ID NO:2)>RADA16 (SEQ ID NO:1).

TABLE 3A

Formulation chart of peptide compositions by varying their concentration with deionized water to obtain specifically esired storage moduli, calculated with the linear trendline equations presented above.

| Storage modulus (Pa) | RADA16 (SEQ ID NO: 1) | KLD12 (SEQ ID NO: 2) | IEIK13 (SEQ ID NO: 3) |
|---|---|---|---|
| 25 | 0.8 | | |
| 50 | 0.9 | | |
| 75 | 1.0 | 0.9 | |
| 100 | 1.2 | | |
| 125 | 1.3 | 1.0 | |
| 150 | 1.5 | 1.1 | 0.5 |
| 175 | 1.6 | | |
| 200 | 1.7 | 1.2 | |
| 225 | 1.9 | | |
| 250 | 2.0 | 1.3 | 0.6 |
| 275 | 2.2 | | |
| 300 | 2.3 | 1.4 | |
| 325 | 2.4 | | |
| 350 | 2.6 | 1.5 | 0.7 |
| 375 | 2.7 | | |
| 400 | 2.9 | 1.6 | |
| 425 | 3.0 | 1.7 | |
| 500 | 3.4 | 1.8 | 0.8 |
| 600 | 4.0 | 2.0 | 0.9 |
| 700 | 4.5 | 2.2 | 1.0 |
| 800 | 5.1 | 2.5 | 1.1 |
| 900 | | 2.7 | 1.2 |
| 1000 | | 2.9 | 1.3 |
| 1050 | | 3.0 | 1.4 |
| 1200 | | 3.3 | 1.5 |
| 1400 | | 3.7 | 1.7 |
| 1600 | | 4.1 | 1.9 |
| 1800 | | 4.5 | 2.1 |
| 2000 | | 5.0 | 2.3 |
| 2200 | | | 2.5 |

The present Example further describes measurement of various rheological properties of certain peptide compositions at selected concentrations using a rheometer (AR500, TA Instruments) with 40 mm plates. A peptide composition (700 µL) was placed on the rheometer plate and excess composition was gently removed by Kimwipes. Measurements were performed after 2 minutes of relaxation time at 37° C. Storage modulus, loss modulus, and viscosity (η') were measured at 37° C. with the plates placed at a measuring geometry gap of 300 µm, and stress sweep tests were performed at 0.1 Pa~1000 Pa of oscillation stress with angular frequency at 10 rad/s.

Figure 2A:
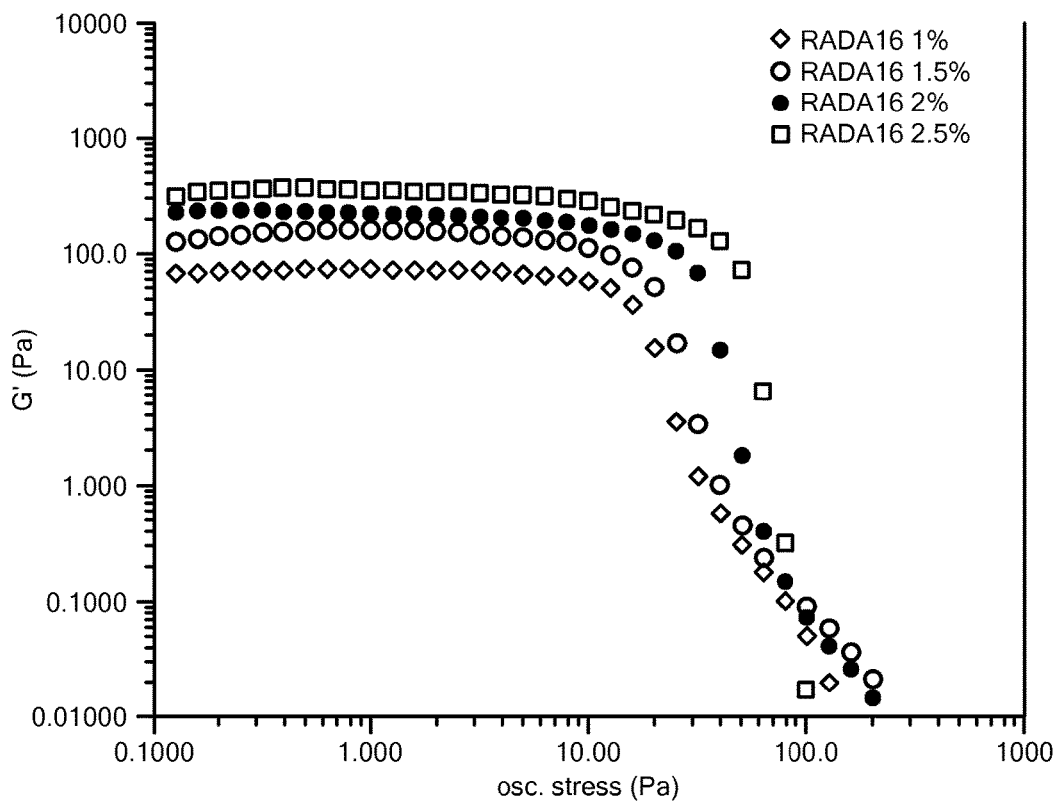
FIGS. 2A and 2B show exemplary rheological properties of RADA16 (SEQ ID NO:1).
Figure 2B:
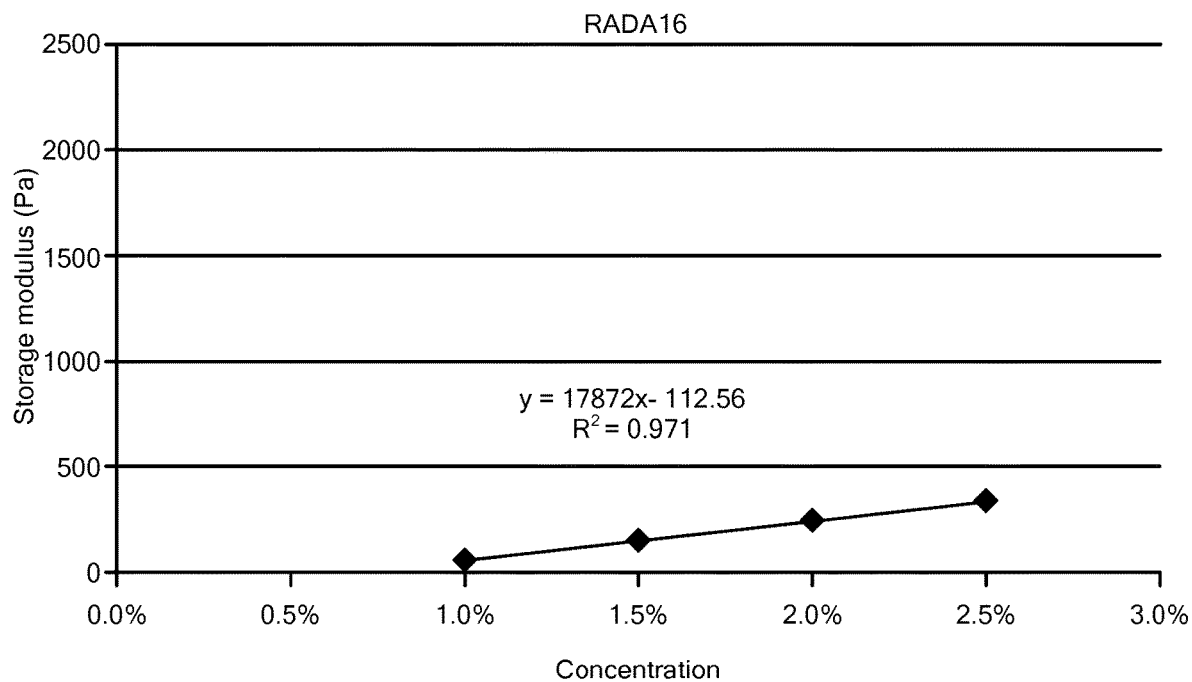
Figure 3A:
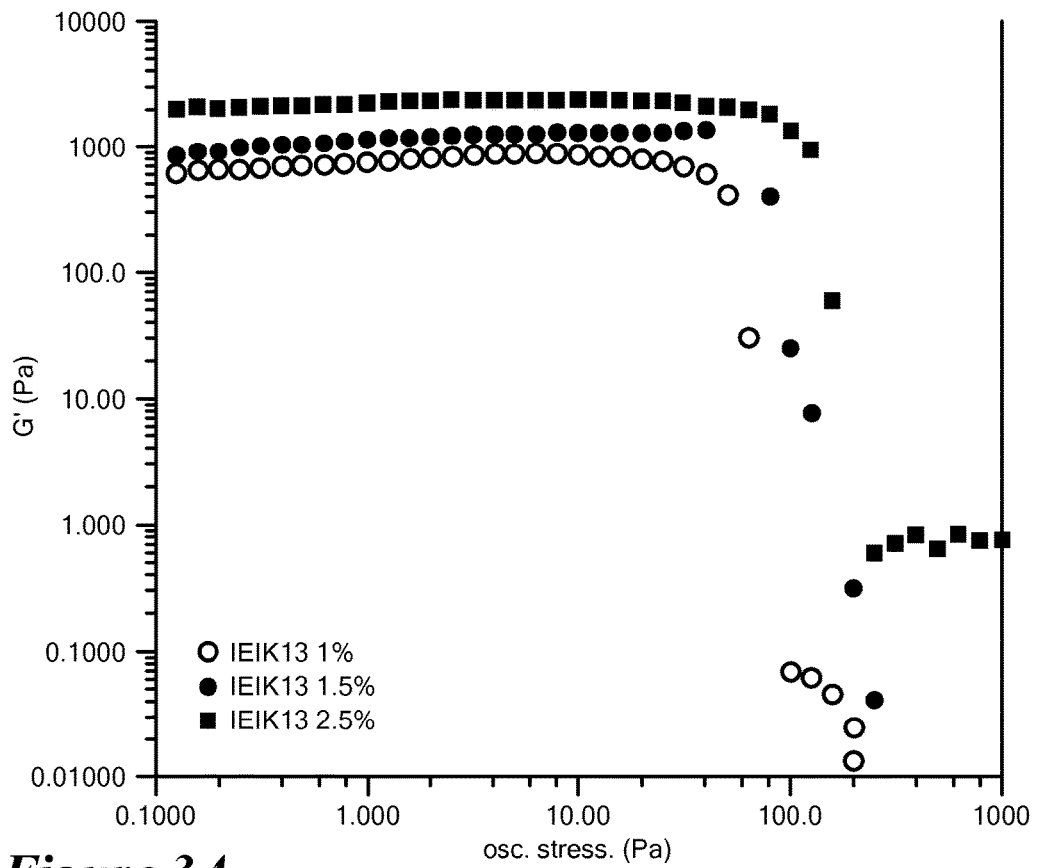
FIGS. 3A and 3B show exemplary rheological properties of IEIK13 (SEQ ID NO:3).
Figure 3B:
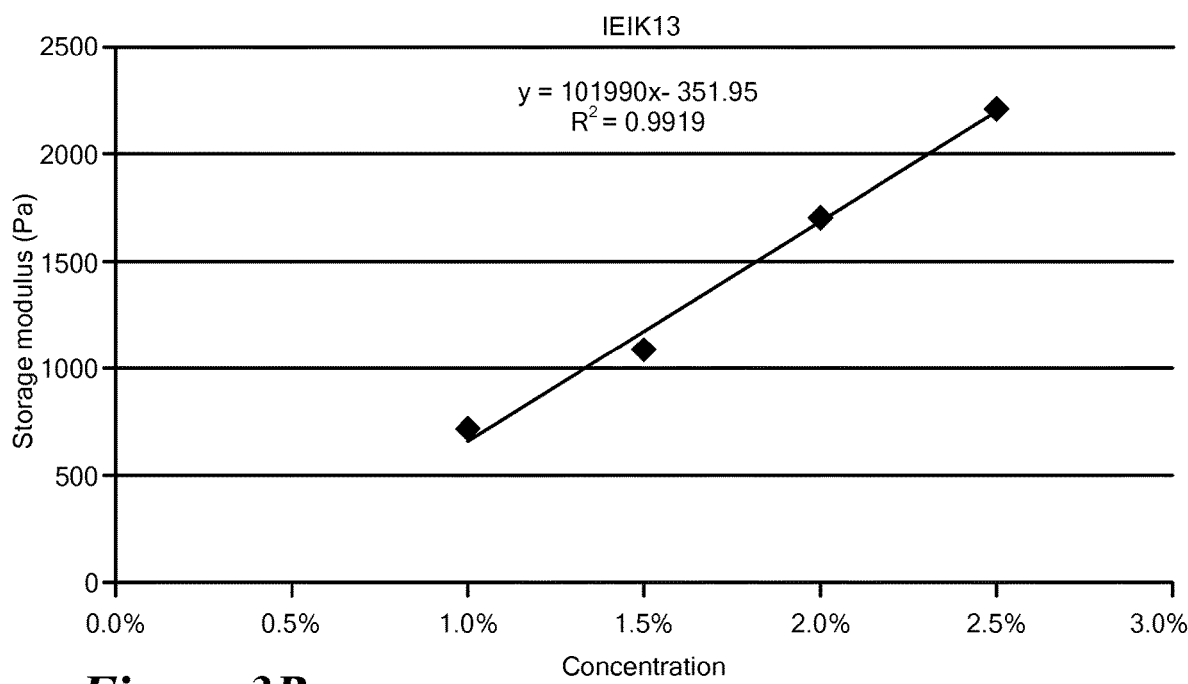
Figure 4A:
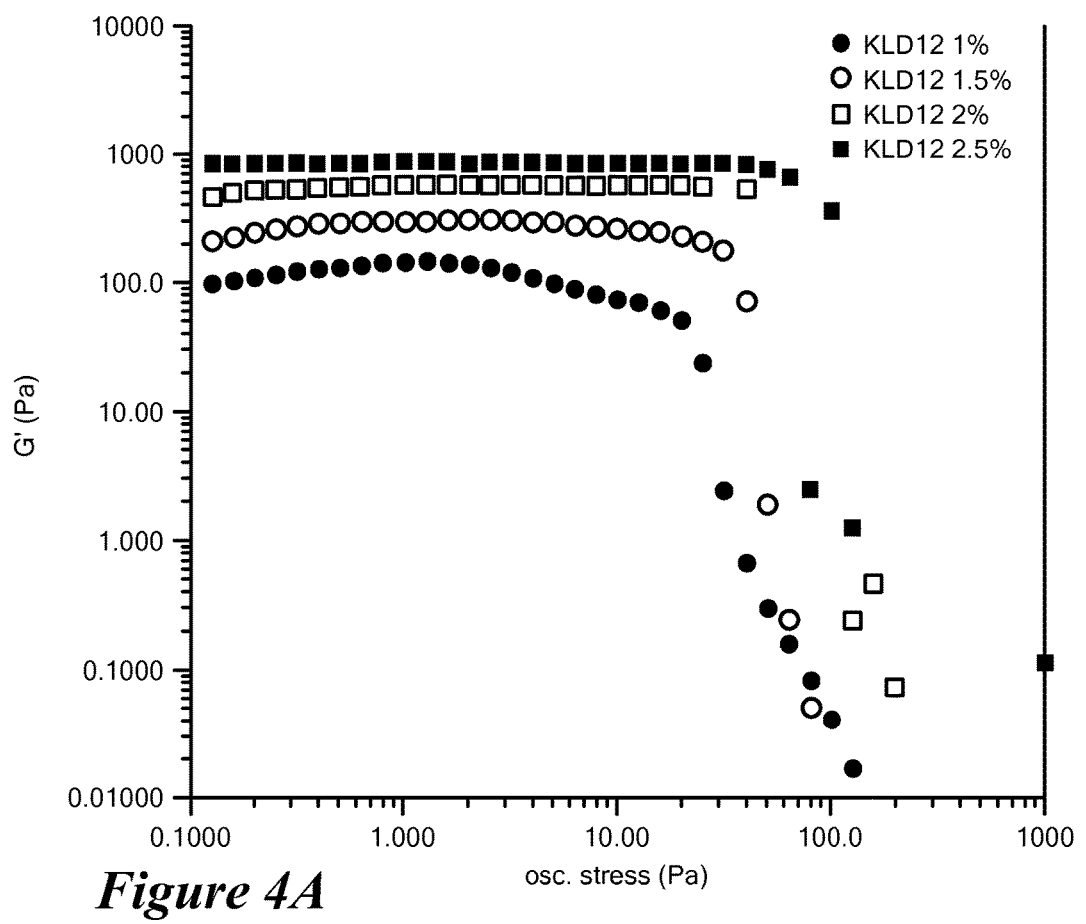
FIGS. 4A and 4B show exemplary rheological properties of KLD12 (SEQ ID NO:2).
Figure 4B:
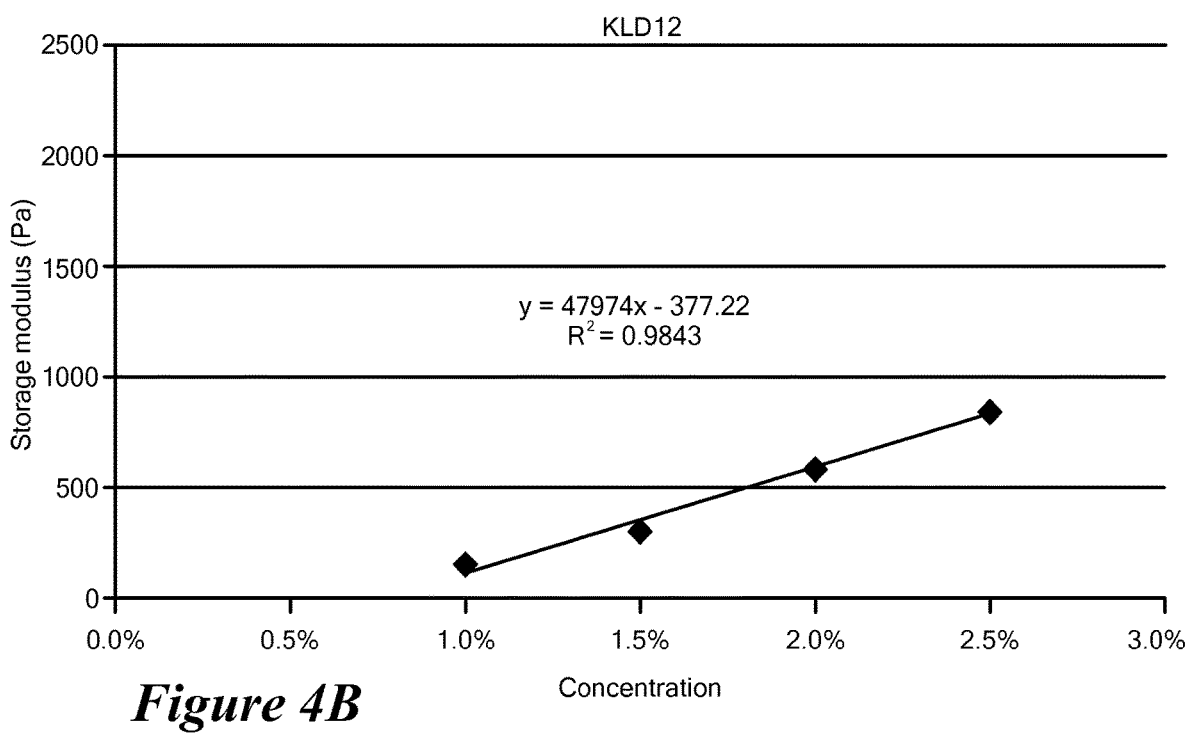

Results are shown in FIGS. 2-4 for RADA16 (SEQ ID NO:1), IEIK13 (SEQ ID NO:3), and KLD12 (SEQ ID NO:2). As shown in FIGS. 2-4, peptide compositions showed near plateau moduli when oscillation stress was less than about 10 to 200 Pa. They all had a dramatic modulus decrease at a certain yield oscillation stress. At least within the tested concentration range of about 1% to about 2.5%, peptide compositions showed a linear increase of storage modulus with increased concentration (R2 of linear trend-lines are between 0.971~0.992). Certain peptide compositions demonstrated a shear thinning property over a critical stress level.

The determined rheological results for various peptide compositions tested in the present Example are listed in Table 3. As can be seen, the storage modulus of 1.5% KLD12 (SEQ ID NO:2) was found to be similar to that of 2.5% RADA16 (SEQ ID NO:1). The storage modulus of 1% IEIK13 (SEQ ID NO:3) was found to be similar to that of 2.5% KLD12 (SEQ ID NO:2) and higher than that of 2.5% RADA16 (SEQ ID NO:1). Overall, the order of rheological strength among the compositions tested here was IEIK13 (SEQ ID NO:3)>KLD12 (SEQ ID NO:2)>RADA16 (SEQ ID NO:1).

TABLE 3

Rheological properties of peptide compositions at selected concentrations

| Peptides | Conc. (%) | Storage Modulus (G')* (Pa) | Loss Modulus (G")* (Pa) | Yield Stress (Pa)*,# | Max. Viscosity (max η') (Pa · s)*,# |
|---|---|---|---|---|---|
| RADA16 | 1 | 74 | 12 | 15.9 | 2.3 |
| (SEQ ID | 1.5 | 158 | 30 | 20.0 | 3.4 |
| NO: 1) | 2 | 217 | 39 | 31.6 | 4.0 |
|  | 2.5 | 352 | 53 | 50.1 | 5.6 |
| IEIK13 | 1 | 719 | 77 | 39.8 | 12.9 |
| (SEQ ID | 1.5 | 1092 | 94 | 50.1 | 18.0 |
| NO: 3) | 2 | 1708 | 138 | — | — |
|  | 2.5 | 2213 | 174 | 100 | 40.2 |
| KLD12 | 1 | 140 | 25 | 25.1 | 2.0 |
| (SEQ ID | 1.5 | 292 | 46 | 39.8 | 7.1 |
| NO: 2) | 2 | 573 | 63 | 79.4 | 11.0 |
|  | 2.5 | 846 | 93 | 100 | 19.0 |

*at 1 Pa of oscillation stress
Maximum viscosity data was adapted in viscosity plots at the range of measured stress.

Example 3: Rheological Properties of Peptide Compositions as a Function of pH

The present Example describes effects of pH on rheological properties of certain peptide compositions. In some embodiments, pH may be a control parameter that impacts stiffness, viscosity, and/or recovery time of peptide compositions.

Table 2, below, presents pH concentrations observed for reference compositions in which the indicated peptide is solubilized in water at the indicated concentration.

TABLE 2 pH values of reference peptide compositions (in water) at selected concentrations.

| Peptide | Concentration | pH |
|---|---|---|
| RADA16 | 2.5% | 2.5 |
| (SEQ ID NO: 1) | 2.0% | 2.5 |
|  | 1.5% | 2.5 |
|  | 1.0% | 2.5 |
|  | 0.5% | 2.7 |
| IEIK13 | 2.5% | 1.8 |
| (SEQ ID NO: 3) | 2.0% | 1.9 |
|  | 1.5% | 2.1 |
|  | 1.0% | 2.1 |
|  | 0.5% | 2.3 |
| KLD12 | 2.5% | 1.8 |
| (SEQ ID NO: 2) | 2.0% | 1.9 |
|  | 1.5% | 2.0 |
|  | 1.0% | 2.0 |
|  | 0.5% | 2.2 |

In this Example, pH levels of peptide compositions was adjusted, for example, by addition of 0.1 N NaOH to 2 mL of a 2.5% peptide composition. pH and appearance of the adjusted compositions were observed. An acidic salt was added if the pH level was higher than the desired level.

Results are shown in Table 5. Notably, a pH increase (i.e., up to about 3.5 or less) did not change the clear color of RADA16 (SEQ ID NO:1), IEIK13 (SEQ ID NO:3), and KLD12 (SEQ ID NO:2) compositions, while their apparent stiffness was increased. With certain compositions, when pH levels of peptide compositions were higher than 3.5 (RADA16 (SEQ ID NO:1) and KLD12 (SEQ ID NO:2)) or 3.7 (IEIK13 (SEQ ID NO:3)), the peptide compositions began phase separation (i.e. becoming cloudy). In some embodiments, provided peptide compositions have a pH within the range of about 3.0 to about 3.7 (particularly for IEIK13 (SEQ ID NO:3)), or about 3.0 to about 3.5 (particularly for RADA16 (SEQ ID NO:1) and/or KLD12 (SEQ ID NO:2)).

TABLE 5

Visual observation of certain peptide compositions at selected pH levels

| Peptides | 0.1N NaOH added in 2.5% composition (μL/mL) | Conc. (%) | Peptide composition pH | Observation |
|---|---|---|---|---|
| RADA16 | 0 | 2.5 | 2.2 | Clear, thick gel |
| (SEQ ID | 50 | 2.38 | 2.3 | Clear, thick gel |
| NO: 1) | 100 | 2.27 | 2.4 | Clear, thick gel |
|  | 150 | 2.17 | 2.7 | Clear, thick, stiffer gel |
|  | 200 | 2.08 | 2.9 | Clear, thick, stiffer gel |
|  | 250 | 2.0 | 3.2 | Clear, thick, stiffer gel |
|  | 275 | 1.96 | 3.4 | Clear, thick, stiffer gel |
|  | 300 | 1.92 | 3.6 | Slightly cloudy, brittle gel |
|  | 350 | 1.85 | 4.5 | Cloudy, phase-separated |
|  |  |  | 7.0 | Cloudy, phase-separated |
| IEIK13 | 0 | 2.5 | 1.8 | Clear, thick gel |
| (SEQ ID | 50 | 2.38 | 2.1 | Clear, thick gel |
| NO: 3) | 100 | 2.27 | 2.2 | Clear, thick gel |
|  | 150 | 2.17 | 2.7 | Clear, thick gel, stiffer gel |
|  | 200 | 2.08 | 3.0 | Clear, thick gel, stiffer gel |
|  | 250 | 2.0 | 3.3 | Clear, thick gel, stiffer gel |
|  | 275 | 1.96 | 3.7 | Clear, thick, stiffer gel |
|  | 300 | 1.92 | 4.0 | Slightly cloudy, brittle gel |
|  | 350 | 1.85 | 4.5 | Cloudy, brittle gel |
|  | 400 | 1.79 | 5.4 | Cloudy, phase-separated |
|  |  |  | 7.0 | Cloudy, phase-separated |
| KLD12 | 0 | 2.5 | 2.1 | Clear, thick gel |
| (SEQ ID | 50 | 2.38 | 2.4 | Clear, thick gel |
| NO: 3) | 100 | 2.27 | 2.6 | Clear, thick gel |
|  | 150 | 2.17 | 2.9 | Clear, thick and stiffer gel |
|  | 200 | 2.08 | 3.3 | Clear, thick and stiffer gel |
|  | 225 | 2.04 | 3.6 | Clear, thick and stiffer gel |
|  | 250 | 2.0 | 4.0 | Slightly cloudy, brittle gel |
|  | 300 | 1.92 | 4.7 | Cloudy, brittle gel |
|  | 350 | 1.85 | 5.2 | Cloudy, phase-separated |
|  |  |  | 7.0 | Cloudy, phase-separated |

Rheological properties of certain peptide compositions were observed before and after adjusting their pH levels to 3.4 (RADA16 (SEQ ID NO:1) and KLD12 (SEQ ID NO:2)) or 3.7 (IEIK13 (SEQ ID NO:3)). Rheological properties of peptides were evaluated using a rheometer (AR500, TA Instruments) with 40 mm plates. Specifically, a peptide composition (700 μL) was placed on the rheometer plate and excess composition was gently removed by Kimwipes. Measurements were performed after 2 minutes of relaxation time at 37° C. Stress sweep test results are shown in FIG. 8-11. RADA16 (SEQ ID NO:1), KLD12 (SEQ ID NO:2) and IEIK13 (SEQ ID NO:3) compositions at elevated pH were stiffer than those at 2.5 (RADA16 (SEQ ID NO:1)), 2.0 (KLD12 (SEQ ID NO:2)), and 2.1 (IEIK13 (SEQ ID NO:3)).

Figure 18:
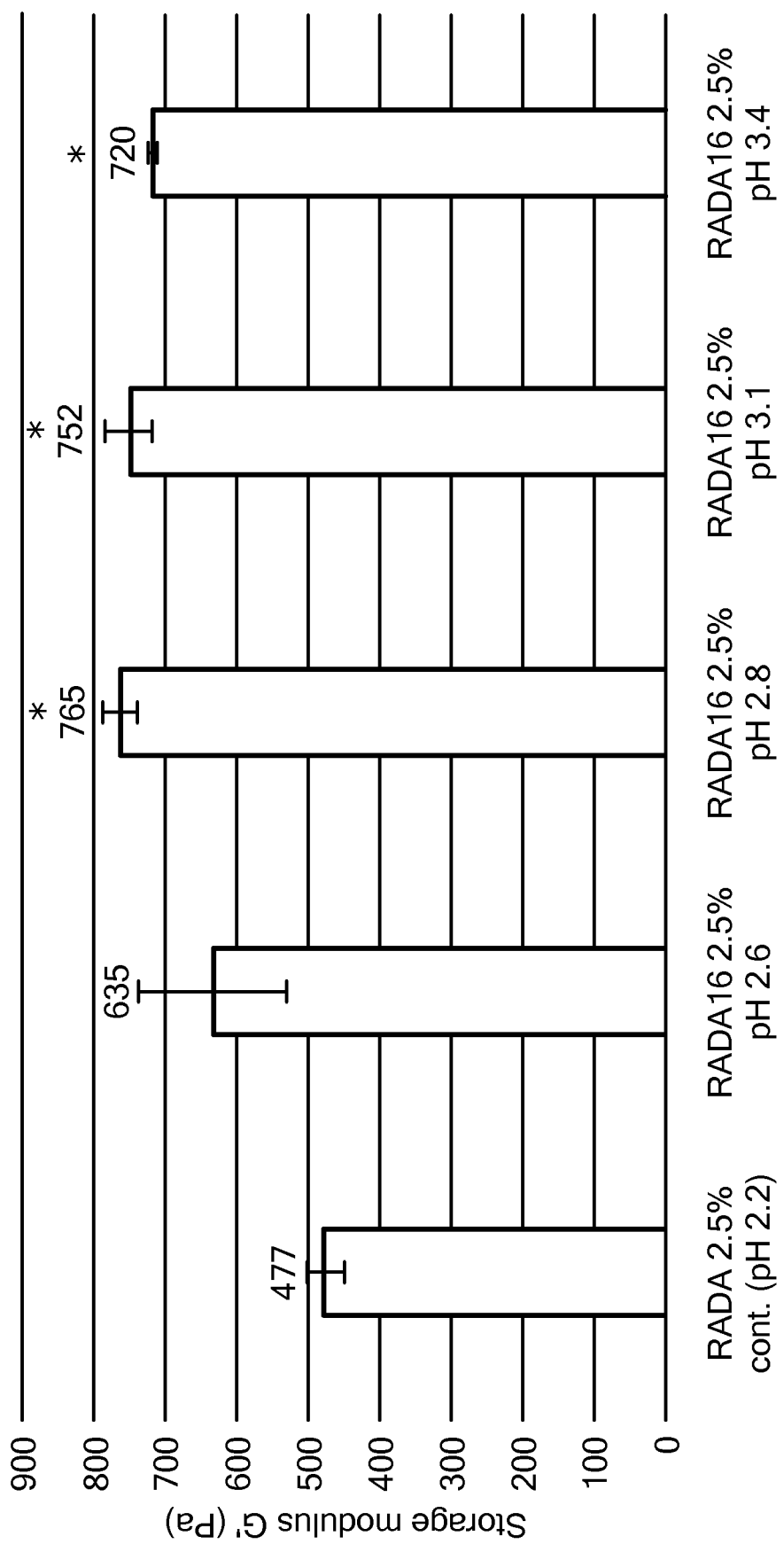
FIG. 18 is a bar graph of storage modulus, showing the effect of pH on the rheological properties of 2.5% RADA16 (SEQ ID NO:1). The storage moduli were measured at 1 rad/s.
Figure 19:
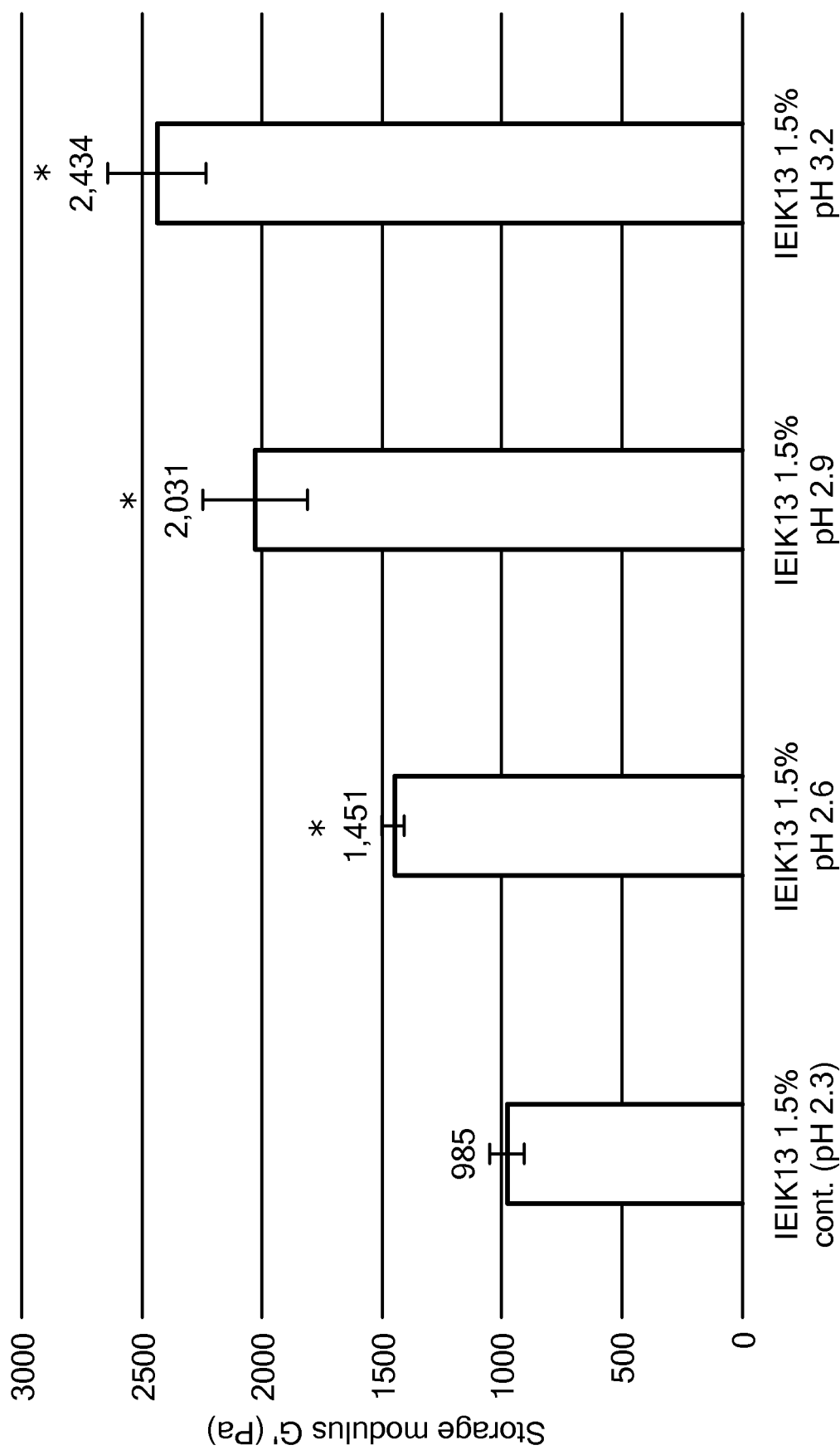
FIG. 19 is a bar graph of storage modulus, showing the effect of pH on the rheological properties of 1.5% IEIK13 (SEQ ID NO:3). The storage moduli were measured at 1 rad/s.

Storage modulus of certain peptide compositions at selected pH levels were evaluated using a rheometer (DHR-1, TA Instruments) with 20 mm plates. Storage modulus of RADA16 (SEQ ID NO:1) and IEIK13 (SEQ ID NO:3) compositions were increased with pH increase up to 3.4. Determined storage moduli for tested peptide compositions are shown in FIG. 18 for RADA16 (SEQ ID NO:1) and FIG. 19 for IEIK13 (SEQ ID NO:3), respectively.

Figure 20A:
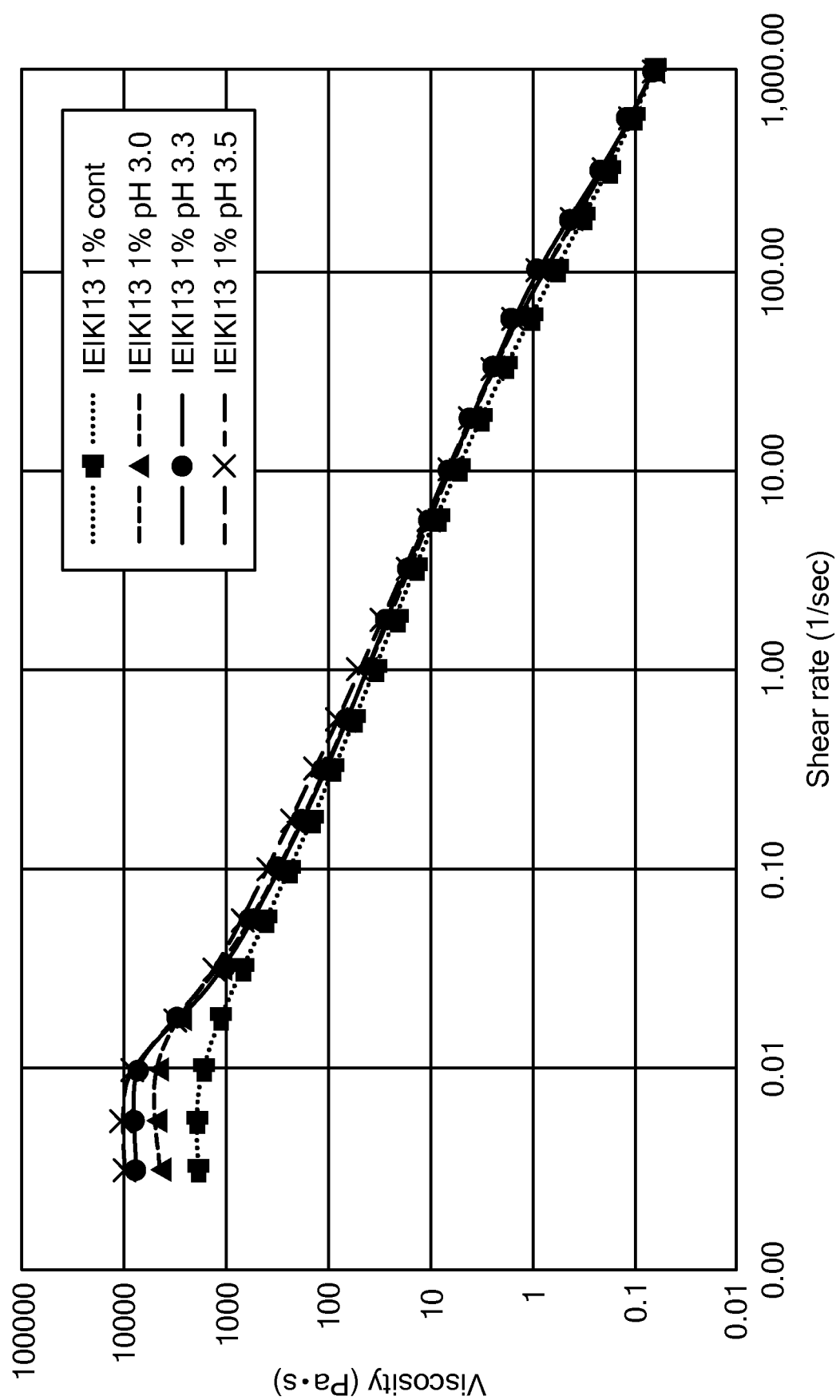
FIG. 20A shows exemplary flow viscosity tests of 1% IEIK13 (SEQ ID NO:3) at pH=2.1, 3.0, 3.3 and 3.5.
Figure 20B:
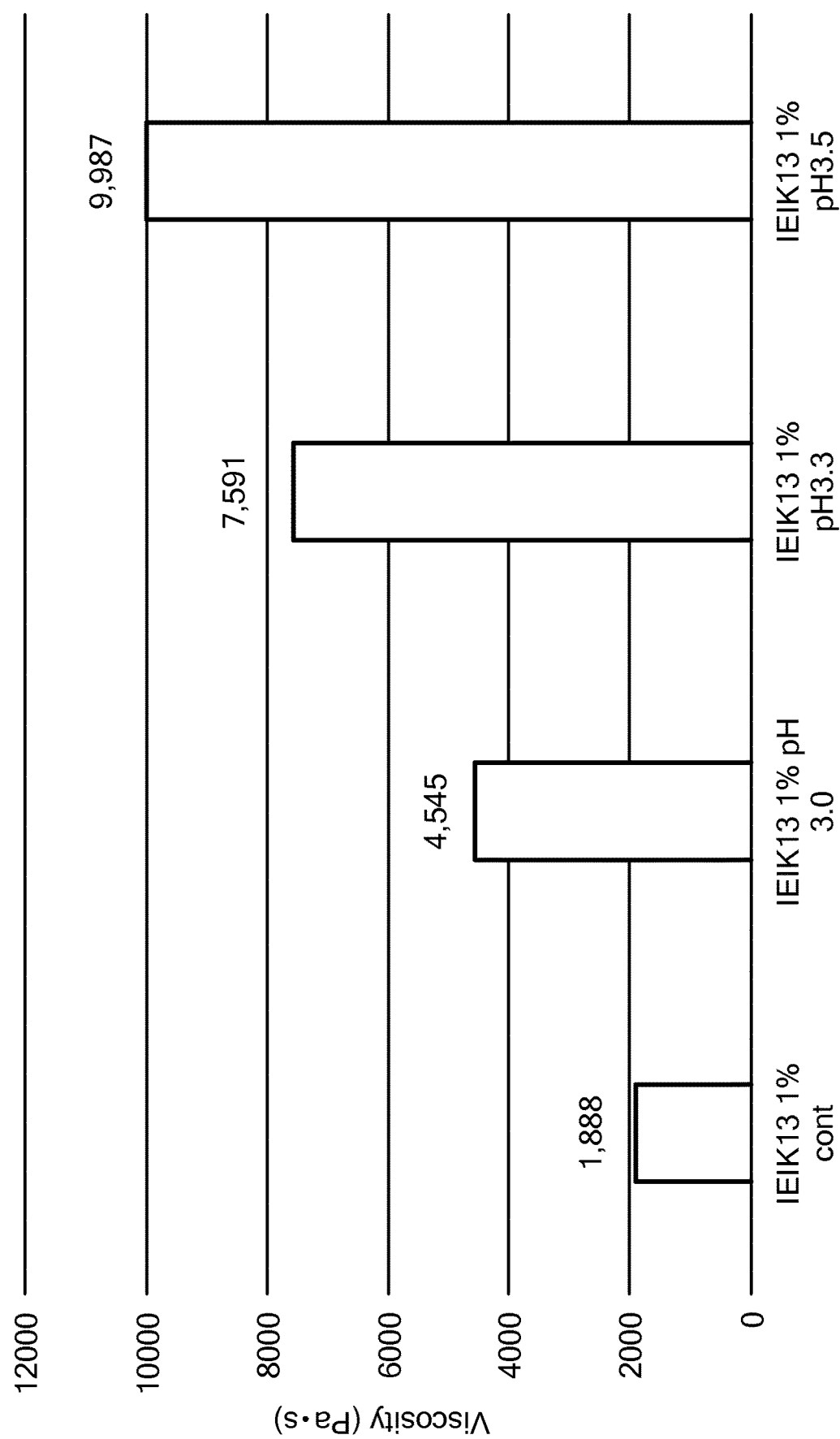
FIG. 20B is a bar graph of exemplary viscosity measurements with the shear rate of 0.003 1/sec.
Figure 21A:
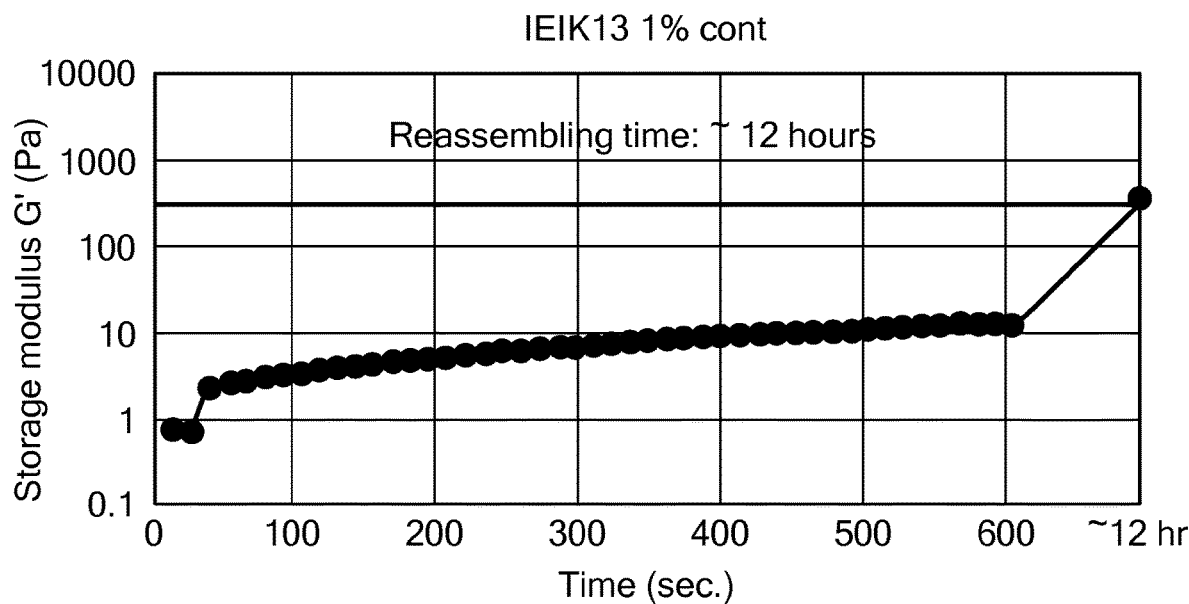
FIGS. 21A, 21B, 21C and 21D show storage modulus measurements as a function of time after applying high shear stress to 1% IEIK13 (SEQ ID NO:3) at pH=2.1, 3.0, 3.3, and 3.5, respectively. The horizontal lines indicate the original storage moduli of 1% IEIK13 (SEQ ID NO:3).
Figure 21B:
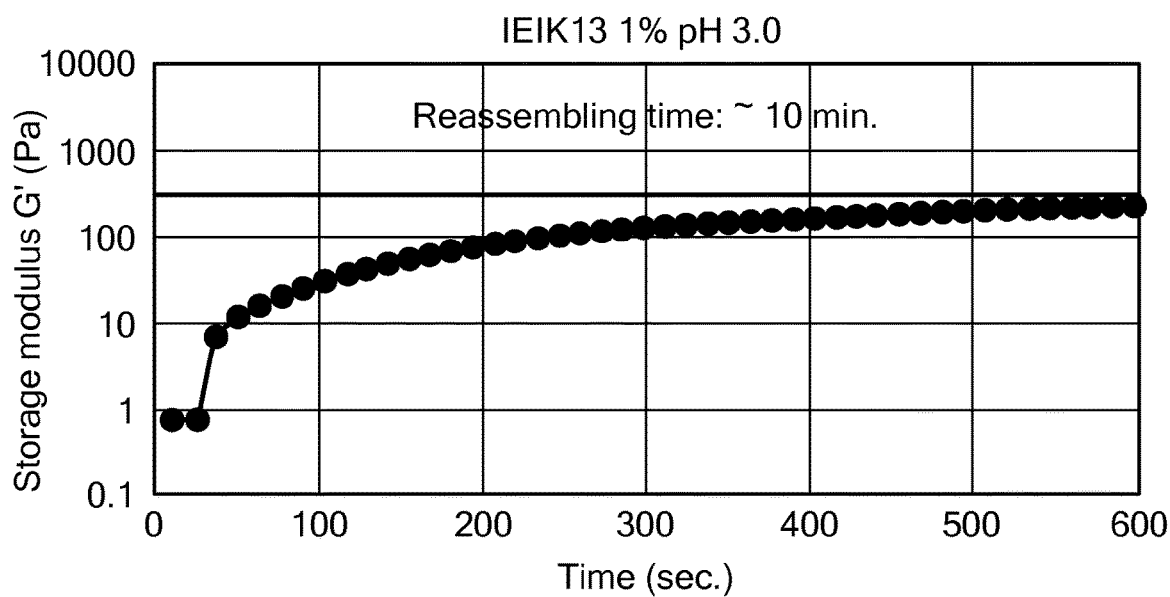
Figure 21C:
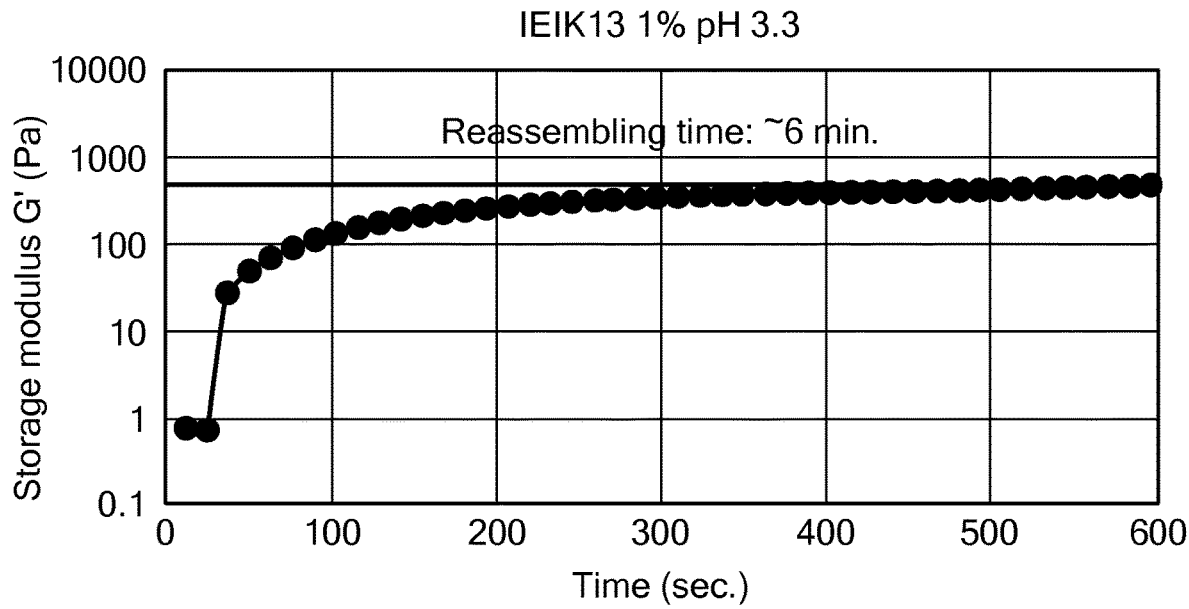
Figure 21D:
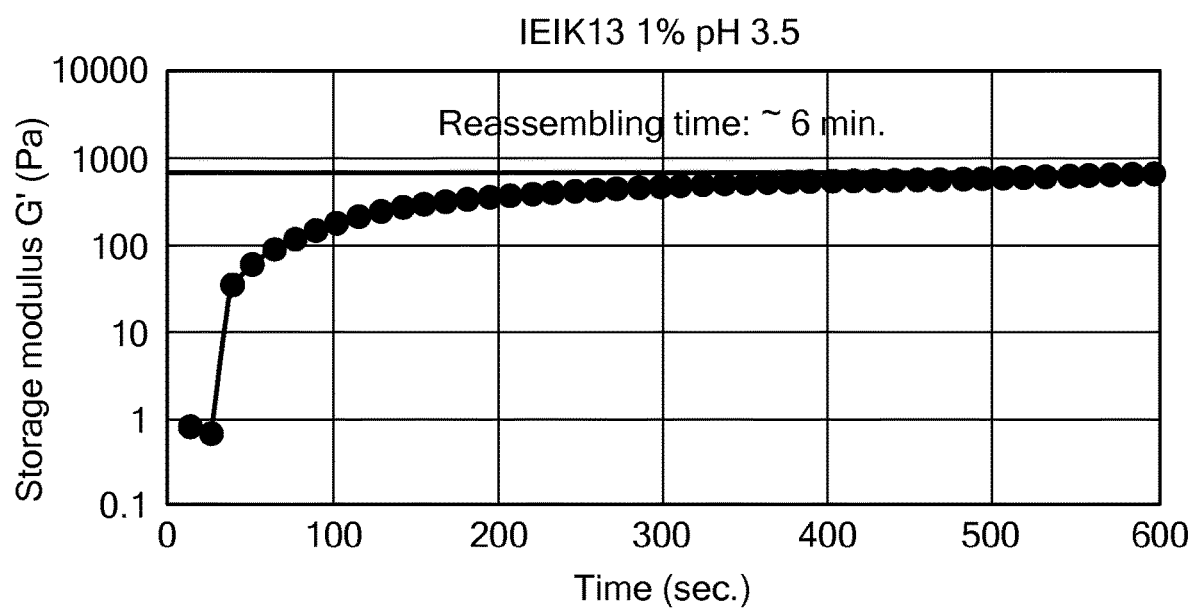

Viscosities of 1% IEIK13 (SEQ ID NO:3) compositions at selected pH levels were evaluated using a rheometer (DHR-1, TA Instruments) with 20 mm plates. Viscosities of IEIK13 (SEQ ID NO:3) compositions increased with pH increase up to 3.5. IEIK13 (SEQ ID NO:3) compositions showed a typical shear thinning property. The results are shown in FIGS. 20A and 20B.

Recovery times of rheological properties were evaluated at selected pH after applying high shear stress to 1% IEIK13 (SEQ ID NO:3) compositions. Using DHR-1 rheometer (TA Instruments), storage modulus changes of 1% IEIK13 (SEQ ID NO:3) were measured with at 1 rad/s at 1 Pa after applying 1000 1/sec of shear rate to samples for 1 min. IEIK13 (SEQ ID NO:3) compositions at selected pH showed a typical thixotropic behavior, which means their rheological properties were slowly recovered. Without wishing to be bound by any particular theory, we propose that rheological property recovery times represent time required for reassembly of peptide molecules to form self-associations (e.g., nano fibers) again in the compositions. Complete reassembling time of 1% IEIK13 (SEQ ID NO:3) control composition (pH 2.3) was up to 12 hours or less, while those of pH-elevated IEIK13 (SEQ ID NO:3) compositions were 6~10 min. Representative results are shown in FIG. 21A-21D for IEIK13 (SEQ ID NO:3).

Example 4: Rheological Properties of Peptide Compositions as a Function of Ionic Strength The present Example describes effects of ionic strength on rheological properties of certain peptide compositions. In some embodiments, ionic strength may be a control parameter of stiffness, viscosity, and/or recovery time of peptide compositions.

Visual observations of RADA16 (SEQ ID NO:1), KLD12 (SEQ ID NO:2), and IEIK13 (SEQ ID NO:3) compositions with selected salts (e.g. KCl, MgCl$_2$, CaCl$_2$) are summarized in Tables 7-9. Peptide compositions at certain ionic strengths were clear and showed higher stiffness than those at lower ionic strength. For RADA16 (SEQ ID NO:1) (Table 7), ionic strength within the range of approximately 0.85~1.15 M (depending on salt identities) did not noticeably change the opacity of RADA16 (SEQ ID NO:1) compositions. For KLD12 (SEQ ID NO:2) (Table 8), ionic strength within the range of approximately 0.25~0.35 M (depending on salt identities) did not noticeably change the opacity of KLD12 (SEQ ID NO:2) compositions. For IEIK13 (SEQ ID NO:3) (Table 9), ionic strength within the range of approximately 0.025~0.035 M (depending on salt identities) did not change the opacity of IEIK13 (SEQ ID NO:3) compositions. Apparent stiffness of RADA16 (SEQ ID NO:1), KLD12 (SEQ ID NO:2) and IEIK13 (SEQ ID NO:3) compositions was increased with increased ionic strength.

Without wishing to be bound by any particular theory, we propose that increased rheological properties may relate to the salting out constant, K, of each salt. The constant K of NaCl for RADA16 (SEQ ID NO:1) may be higher than the other salts. Rheological properties of the RADA16 (SEQ ID NO:1) compositions with NaCl were slightly higher than those with KCl and CaCl$_2$.

TABLE 7

Visual observation of RADA16 compositions with selected salts at room temperature

| Salt solution | Volume of salt solution added in 1.5% RADA16 (SEQ ID NO: 1) composition (μL/mL) | Conc. of RADA16 (SEQ ID NO: 1) (%) | Conc. of salt (M) | Ionic Strength (M) | Observation |
|---|---|---|---|---|---|
| NaCl | 0 | 1.5 | 0 | 0 | Clear, thick gel |
| (3M-as a | 52.6 | 1.43 | 0.15 | 0.15 | Clear, thick, stiffer gel |
| stock | 111.1 | 1.35 | 0.3 | 0.3 | Clear, thick, stiffer gel |
| solution) | 176.5 | 1.27 | 0.45 | 0.45 | Clear, thick, stiffer gel |
| | 250 | 1.2 | 0.6 | 0.6 | Clear, thick, stiffer gel |
| | 333.3 | 1.13 | 0.75 | 0.75 | Clear, thick, stiffer gel |
| | 363.6 | 1.10 | 0.8 | 0.8 | Clear, thick, stiffer gel |
| | 395.3 | 1.08 | 0.85 | 0.85 | Clear, thick, stiffer gel |
| | 428.6 | 1.05 | 0.9 | 0.9 | Slightly cloudy, brittle gel |
| | 463.4 | 1.03 | 0.95 | 0.95 | Cloudy, phase-separated |
| | 500 | 1.0 | 1.0 | 1.0 | Cloudy, phase-separated |
| KCl | 0 | 1.5 | 0 | 0 | Clear, thick gel |
| (3M-as a | 52.6 | 1.43 | 0.15 | 0.15 | Clear, thick, stiffer gel |
| stock | 111.1 | 1.35 | 0.3 | 0.3 | Clear, thick, stiffer gel |
| solution) | 176.5 | 1.27 | 0.45 | 0.45 | Clear, thick, stiffer gel |
| | 250 | 1.2 | 0.6 | 0.6 | Clear, thick, stiffer gel |
| | 333.3 | 1.13 | 0.75 | 0.75 | Clear, thick, stiffer gel |
| | 428.6 | 1.05 | 0.9 | 0.9 | Clear, thick, stiffer gel |
| | 463.4 | 1.03 | 0.95 | 0.95 | Clear, thick, stiffer gel |
| | 500 | 1.0 | 1.0 | 1.0 | Clear, thick, stiffer gel |
| | 538.5 | 0.98 | 1.05 | 1.05 | Slightly cloudy, thick, stiffer gel |
| | 578.9 | 0.95 | 1.1 | 1.1 | Slightly cloudy, brittle gel |
| | 621.6 | 0.93 | 1.15 | 1.15 | Cloudy, phase-separated |
| MgCl$_2$ | 0 | 1.5 | 0 | 0 | Clear, thick gel |
| (3M-as a | 16.9 | 1.48 | 0.05 | 0.15 | Clear, thick, stiffer gel |
| stock | 34.5 | 1.45 | 0.1 | 0.3 | Clear, thick, stiffer gel |
| solution) | 52.6 | 1.43 | 0.15 | 0.45 | Clear, thick, stiffer gel |
| | 71.4 | 1.4 | 0.2 | 0.6 | Clear, thick, stiffer gel |
| | 90.9 | 1.38 | 0.25 | 0.75 | Clear, thick, stiffer gel |
| | 111.1 | 1.35 | 0.3 | 0.9 | Clear, thick, stiffer gel |
| | 132.1 | 1.32 | 0.35 | 1.05 | Clear, thick, stiffer gel |
| | 146.5 | 1.31 | 0.383 | 1.15 | Clear, thick, stiffer gel |

TABLE 7-continued

Visual observation of RADA16 compositions with selected salts at room temperature

| Salt solution | Volume of salt solution added in 1.5% RADA16 (SEQ ID NO: 1) composition (μL/mL) | Conc. of RADA16 (SEQ ID NO: 1) (%) | Conc. of salt (M) | Ionic Strength (M) | Observation |
|---|---|---|---|---|---|
| | 153.8 | 1.3 | 0.4 | 1.2 | Slightly cloudy, thick, stiffer gel |
| | 161.3 | 1.29 | 0.417 | 1.25 | Slightly cloudy, brittle gel |
| | 168.8 | 1.28 | 0.433 | 1.3 | Cloudy, phase-separated |
| CaCl$_2$ (3M-as a stock solution) | 0 | 1.5 | 0 | 0 | Clear, thick gel |
| | 16.9 | 1.48 | 0.05 | 0.15 | Clear, thick, stiffer gel |
| | 34.5 | 1.45 | 0.1 | 0.3 | Clear, thick, stiffer gel |
| | 52.6 | 1.43 | 0.15 | 0.45 | Clear, thick, stiffer gel |
| | 71.4 | 1.4 | 0.2 | 0.6 | Clear, thick, stiffer gel |
| | 90.9 | 1.38 | 0.25 | 0.75 | Clear, thick, stiffer gel |
| | 111.1 | 1.35 | 0.3 | 0.9 | Clear, thick, stiffer gel |
| | 132.1 | 1.32 | 0.35 | 1.05 | Clear, thick, stiffer gel |
| | 146.5 | 1.31 | 0.383 | 1.15 | Clear, thick, stiffer gel |
| | 153.8 | 1.3 | 0.4 | 1.2 | Slightly cloudy, thick, stiffer gel |
| | 161.3 | 1.29 | 0.417 | 1.25 | Slightly cloudy, brittle gel |
| | 168.8 | 1.28 | 0.433 | 1.3 | Cloudy, phase-separated |
| DPBS (pH 3.2) (10X- 1.5M-as a stock solution) | 0 | 1.5 | 0 | 0 | Clear, thick gel |
| | 111.1 | 1.35 | 0.15 | 0.15 | Clear, thick, stiffer gel |
| | 250 | 1.2 | 0.3 | 0.3 | Clear, thick, stiffer gel |
| | 428.6 | 1.05 | 0.45 | 0.45 | Clear, thick, stiffer gel |
| | 666.7 | 0.9 | 0.6 | 0.6 | Clear, thick, stiffer gel |
| | 1000 | 0.75 | 0.75 | 0.75 | Clear, thick, stiffer gel |
| | 1500 | 0.6 | 0.9 | 0.9 | Clear, thick, stiffer gel |
| | 1725 | 0.55 | 0.95 | 0.95 | Slightly cloudy, brittle gel |
| | 2000 | 0.5 | 1.0 | 1.0 | Cloudy, phase-separated |

TABLE 8

Visual observation of KLD12 compositions with selected salts at room temperature

| Salt solution | Volume of salt solution added in 1.5% KLD12 (SEQ ID NO: 2) composition (μL/mL) | Conc. of (SEQ ID NO: 2) KLD12 (%) | Conc. of salt (M) | Ionic Strength (M) | Observation |
|---|---|---|---|---|---|
| NaCl (3M-as a stock solution) | 0 | 1.5 | 0 | 0 | Clear, thick gel |
| | 16.9 | 1.48 | 0.05 | 0.5 | Clear, thick, stiffer gel |
| | 34.5 | 1.45 | 0.1 | 0.1 | Clear, thick, stiffer gel |
| | 52.6 | 1.43 | 0.15 | 0.15 | Clear, thick, stiffer gel |
| | 71.4 | 1.4 | 0.2 | 0.2 | Clear, thick, stiffer gel |
| | 90.9 | 1.38 | 0.25 | 0.25 | Clear, thick, stiffer gel |
| | 111.1 | 1.35 | 0.3 | 0.3 | Slightly cloudy, thick, stiffer gel |
| | 132.1 | 1.32 | 0.35 | 0.35 | Slightly cloudy, brittle gel |
| | 153.8 | 1.3 | 0.4 | 0.4 | Cloudy, phase-separated |
| KCl (3M-as a stock solution) | 0 | 1.5 | 0 | 0 | Clear, thick gel |
| | 16.9 | 1.48 | 0.05 | 0.5 | Clear, thick, stiffer gel |
| | 34.5 | 1.45 | 0.1 | 0.1 | Clear, thick, stiffer gel |
| | 52.6 | 1.43 | 0.15 | 0.15 | Clear, thick, stiffer gel |
| | 71.4 | 1.4 | 0.2 | 0.2 | Clear, thick, stiffer gel |
| | 90.9 | 1.38 | 0.25 | 0.25 | Clear, thick, stiffer gel |
| | 111.1 | 1.35 | 0.3 | 0.3 | Slightly cloudy, thick, stiffer gel |
| | 132.1 | 1.32 | 0.35 | 0.35 | Slightly cloudy, brittle gel |
| | 153.8 | 1.3 | 0.4 | 0.4 | Cloudy, phase-separated |
| MgCl$_2$ (3M-as a stock solution) | 0 | 1.5 | 0 | 0 | Clear, thick gel |
| | 16.9 | 1.48 | 0.05 | 0.15 | Clear, thick, stiffer gel |
| | 22.7 | 1.47 | 0.067 | 0.2 | Clear, thick, stiffer gel |
| | 28.6 | 1.46 | 0.083 | 0.25 | Clear, thick, stiffer gel |
| | 34.5 | 1.45 | 0.1 | 0.3 | Clear, thick, stiffer gel |
| | 40.2 | 1.44 | 0.117 | 0.35 | Clear, thick, stiffer gel |
| | 46.5 | 1.43 | 0.133 | 0.4 | Slightly cloudy, thick, stiffer gel |
| | 52.6 | 1.43 | 0.15 | 0.45 | Slightly cloudy, brittle gel |
| | 58.8 | 1.42 | 0.167 | 0.5 | Cloudy, phase-separated |

TABLE 8-continued

Visual observation of KLD12 compositions with selected salts at room temperature

| Salt solution | Volume of salt solution added in 1.5% KLD12 (SEQ ID NO: 2) composition (μL/mL) | Conc. of (SEQ ID NO: 2) KLD12 (%) | Conc. of salt (M) | Ionic Strength (M) | Observation |
|---|---|---|---|---|---|
| CaCl$_2$ | 0 | 1.5 | 0 | 0 | Clear, thick gel |
| (3M-as a | 16.9 | 1.48 | 0.05 | 0.15 | Clear, thick, stiffer gel |
| stock | 22.7 | 1.47 | 0.067 | 0.2 | Clear, thick, stiffer gel |
| solution) | 28.6 | 1.46 | 0.083 | 0.25 | Clear, thick, stiffer gel |
|  | 34.5 | 1.45 | 0.1 | 0.3 | Clear, thick, stiffer gel |
|  | 40.2 | 1.44 | 0.117 | 0.35 | Clear, thick, stiffer gel |
|  | 46.5 | 1.43 | 0.133 | 0.4 | Slightly cloudy, thick, stiffer gel |
|  | 52.6 | 1.43 | 0.15 | 0.45 | Slightly cloudy, brittle gel |
|  | 58.8 | 1.42 | 0.167 | 0.5 | Cloudy, phase-separated |

TABLE 9

Visual observation of IEIK13 compositions with selected salts at room temperature

| Salt solution | Volume of salt solution added in 1.5% IEIK13 (SEQ ID NO: 3) composition (μL/mL) | Conc. of (SEQ ID NO: 3) IEIK13 (%) | Conc. of salt (M) | Ionic Strength (M) | Observation |
|---|---|---|---|---|---|
| NaCl | 0 | 1.5 | 0 | 0 | Clear, thick gel |
| (0.2M-as | 25.6 | 1.46 | 0.005 | 0.005 | Clear, thick, stiffer gel |
| a stock | 52.6 | 1.43 | 0.01 | 0.01 | Clear, thick, stiffer gel |
| solution) | 81.1 | 1.39 | 0.015 | 0.015 | Clear, thick, stiffer gel |
|  | 111.1 | 1.35 | 0.02 | 0.02 | Clear, thick, stiffer gel |
|  | 142.9 | 1.31 | 0.025 | 0.025 | Clear, thick, stiffer gel |
|  | 176.5 | 1.27 | 0.03 | 0.03 | Slightly cloudy, thick, stiffer gel |
|  | 212.1 | 1.24 | 0.035 | 0.035 | Slightly cloudy, brittle gel |
|  | 250 | 1.2 | 0.04 | 0.04 | Cloudy, phase-separated |
| KCl | 0 | 1.5 | 0 | 0 | Clear, thick gel |
| (0.2M-as | 25.6 | 1.46 | 0.005 | 0.005 | Clear, thick, stiffer gel |
| a stock | 52.6 | 1.43 | 0.01 | 0.01 | Clear, thick, stiffer gel |
| solution) | 81.1 | 1.39 | 0.015 | 0.015 | Clear, thick, stiffer gel |
|  | 111.1 | 1.35 | 0.02 | 0.02 | Clear, thick, stiffer gel |
|  | 142.9 | 1.31 | 0.025 | 0.025 | Clear, thick, stiffer gel |
|  | 176.5 | 1.27 | 0.03 | 0.03 | Clear, thick, stiffer gel |
|  | 212.1 | 1.24 | 0.035 | 0.035 | Slightly cloudy, brittle gel |
|  | 250 | 1.2 | 0.04 | 0.04 | Slightly cloudy, brittle |
|  | 290.3 | 1.16 | 0.045 | 0.045 | Cloudy, phase-separated |
| MgCl$_2$ | 0 | 1.5 | 0 | 0 | Clear, thick gel |
| (0.2M-as | 25.6 | 1.46 | 0.005 | 0.015 | Clear, thick, stiffer gel |
| a stock | 34.5 | 1.45 | 0.0067 | 0.02 | Clear, thick, stiffer gel |
| solution) | 43.5 | 1.44 | 0.0083 | 0.025 | Clear, thick, stiffer gel |
|  | 52.6 | 1.43 | 0.01 | 0.03 | Clear, thick, stiffer gel |
|  | 61.9 | 1.41 | 0.0117 | 0.035 | Clear, thick, stiffer gel |
|  | 71.4 | 1.40 | 0.0133 | 0.04 | Slightly cloudy, thick, stiffer gel |
|  | 81.1 | 1.39 | 0.015 | 0.045 | Slightly cloudy, stiffer gel |
|  | 91.1 | 1.37 | 0.0167 | 0.05 | Slightly cloudy, brittle gel |
|  | 100.9 | 1.36 | 0.0183 | 0.055 | Cloudy, phase-separated |
| CaCl$_2$ | 0 | 1.5 | 0 | 0 | Clear, thick gel |
| (0.2M-as | 25.6 | 1.46 | 0.005 | 0.015 | Clear, thick, stiffer gel |
| a stock | 34.5 | 1.45 | 0.0067 | 0.02 | Clear, thick, stiffer gel |
| solution) | 43.5 | 1.44 | 0.0083 | 0.025 | Clear, thick, stiffer gel |
|  | 52.6 | 1.43 | 0.01 | 0.03 | Clear, thick, stiffer gel |
|  | 61.9 | 1.41 | 0.0117 | 0.035 | Clear, thick, stiffer gel |
|  | 71.4 | 1.40 | 0.0133 | 0.04 | Slightly cloudy, thick, stiffer gel |
|  | 81.1 | 1.39 | 0.015 | 0.045 | Slightly cloudy, thick, stiffer gel |
|  | 91.1 | 1.37 | 0.0167 | 0.05 | Slightly cloudy, brittle gel |
|  | 100.9 | 1.36 | 0.0183 | 0.055 | Cloudy, phase-separated |

Critical ion strengths were determined from the visual observations recorded in Tables 7-9. When the ionic strengths of peptide compositions were higher than 0.9 M (RADA16 (SEQ ID NO:1)), 0.3 M (KLD12 (SEQ ID NO:2)) or 0.03 M (IEIK13 (SEQ ID NO:3)), the peptide compositions began phase separation. 0.9 M, 0.3 M and 0.03 M may represent critical ion strengths for RADA16 (SEQ ID NO:1), KLD12 (SEQ ID NO:2) and IEIK13 (SEQ ID NO:3), respectively.

Figure 27:
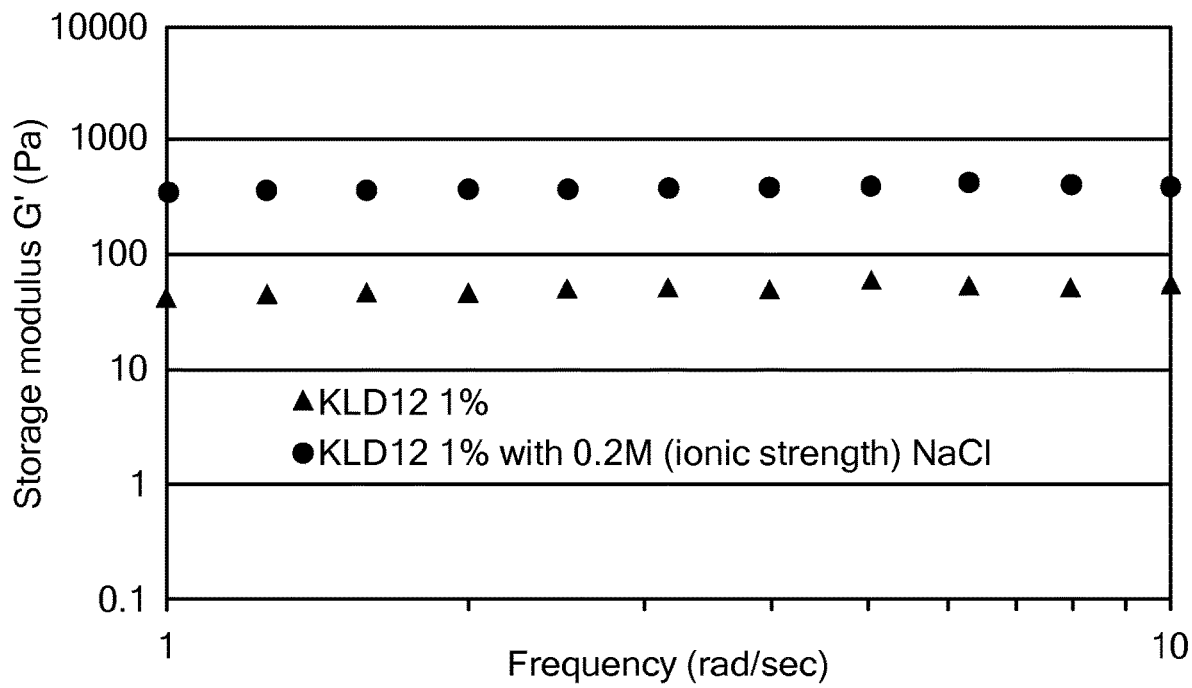
FIGS. 27-29 show exemplary frequency sweep tests from 1 rad/s to 10 rad/s at 1 Pa.
Figure 28:
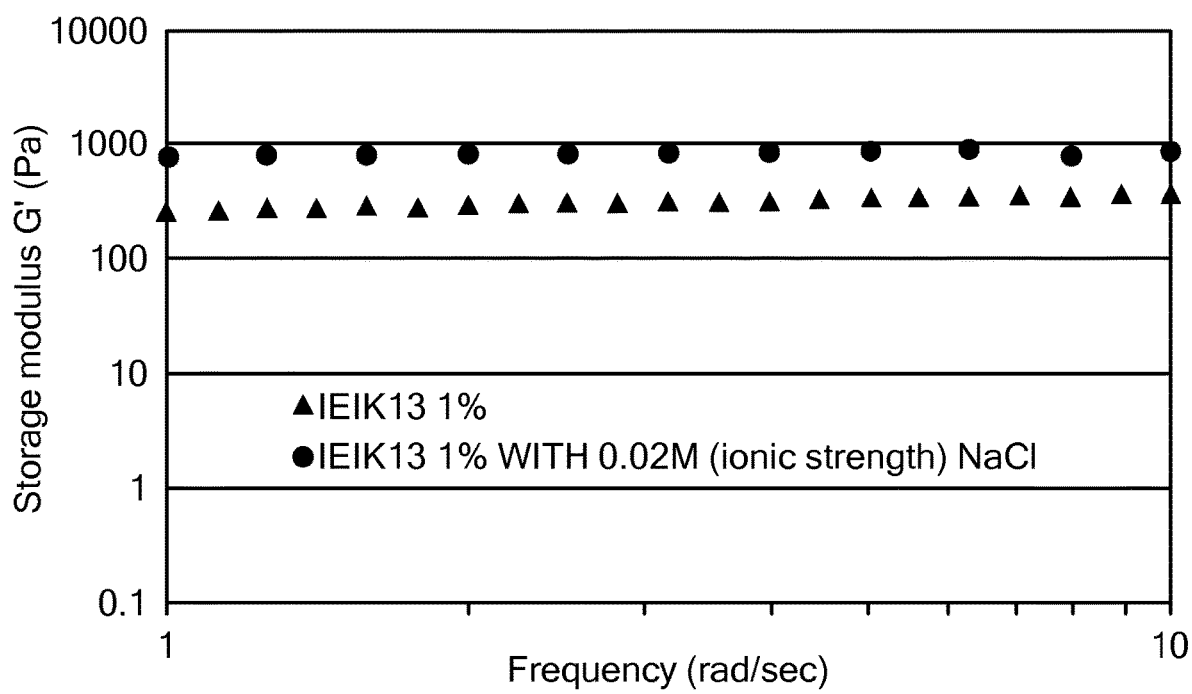
Figure 29:
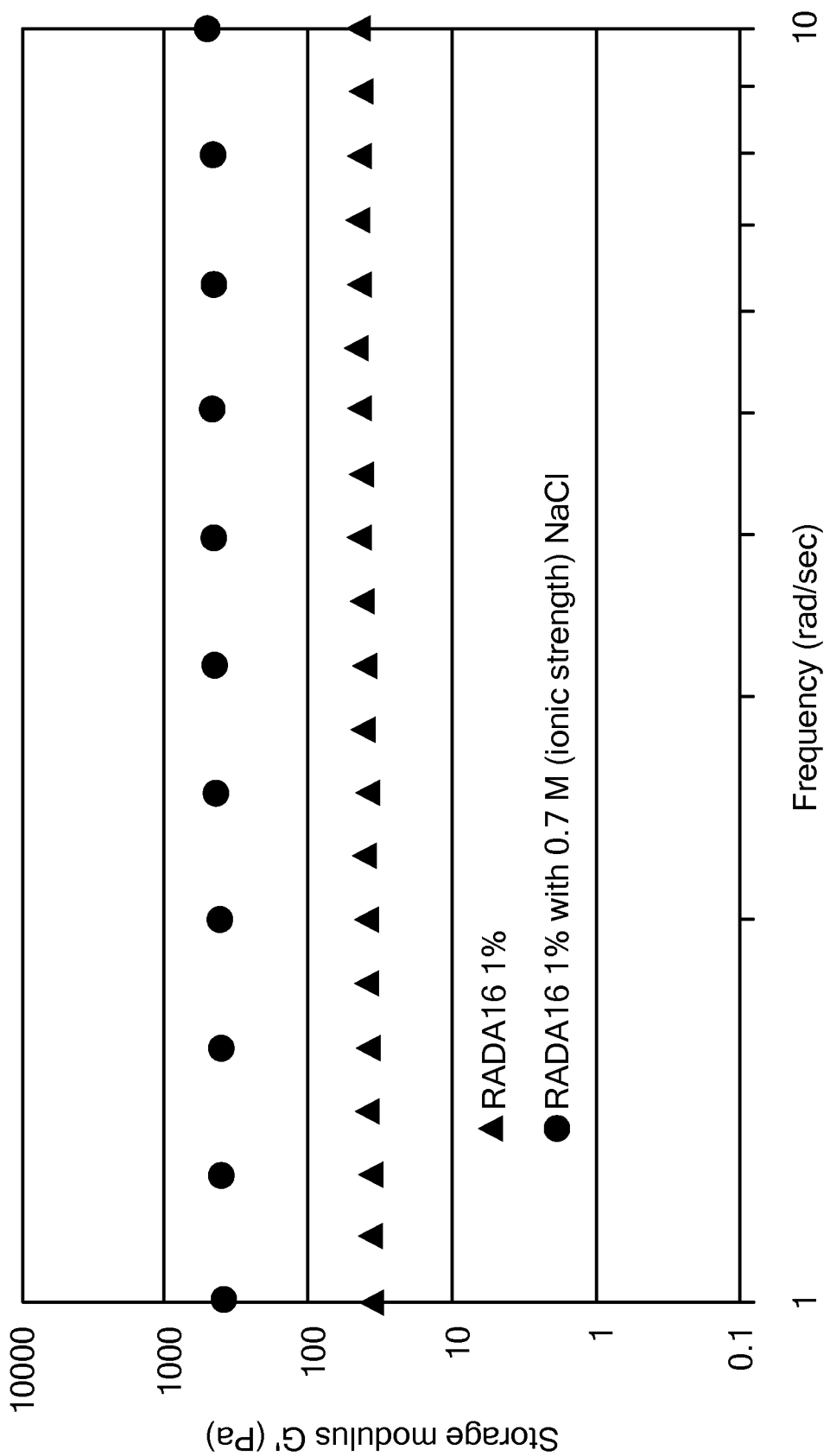

FIGS. 27-29 show rheological properties measured with a rheometer (DHR-1, TA Instruments) with 20 mm plates when ion strengths are slightly lower than the critical ion strengths. Ion strengths of RADA16 (SEQ ID NO:1), KLD12 (SEQ ID NO:2) and IEIK13 (SEQ ID NO:3) were 0.7 M, 0.2 M and 0.02M, respectively for the measurements. Rheological properties of RADA16 (SEQ ID NO:1), KLD12 (SEQ ID NO:2) and IEIK13 (SEQ ID NO:3) compositions were higher after adjusting their ionic strength levels with NaCl to 0.7 M (RADA16 (SEQ ID NO:1)), 0.2 M (KLD12 (SEQ ID NO:2)) or 0.02 M (IEIK13 (SEQ ID NO:3)).

Figure 30:
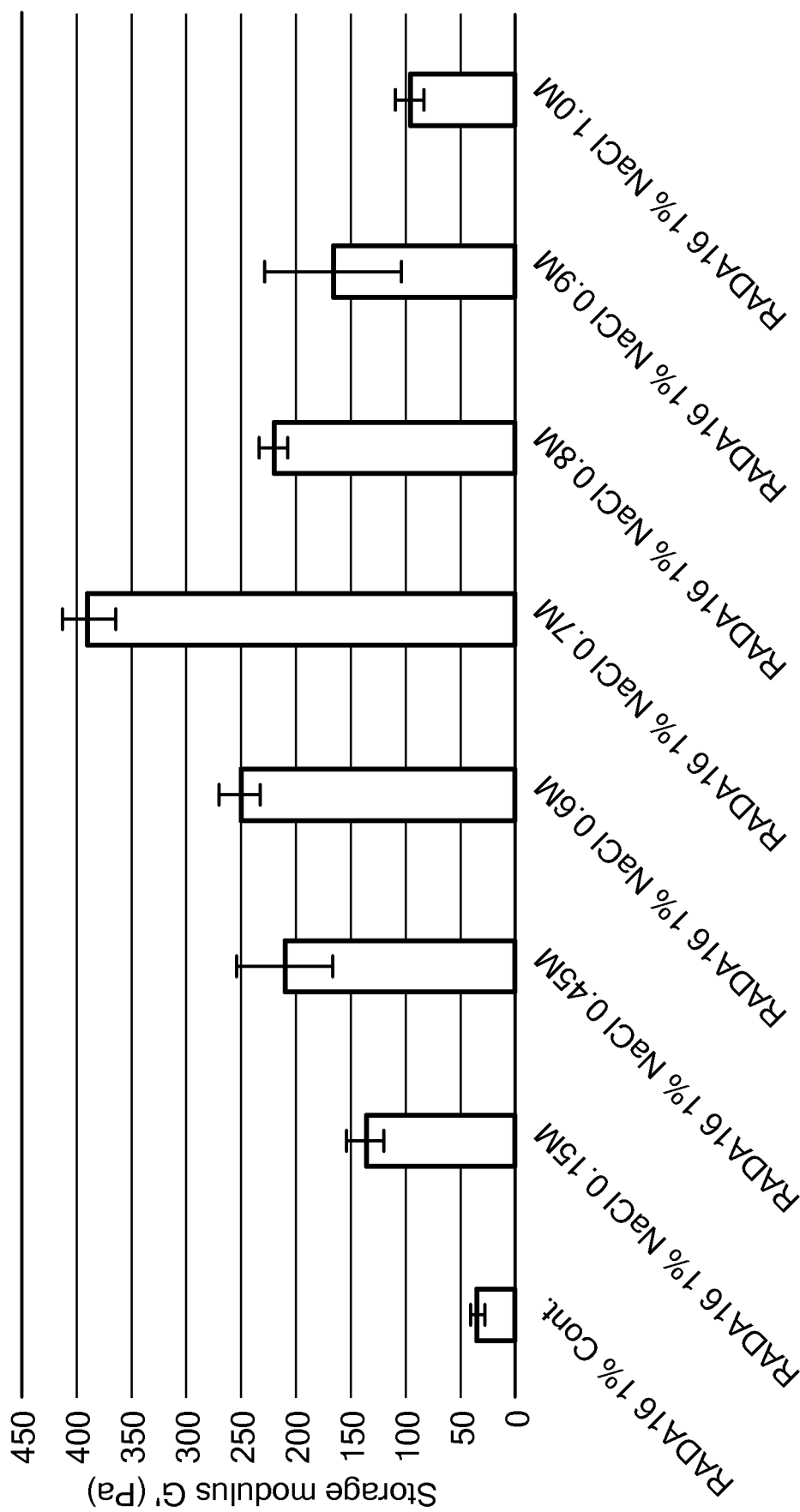
FIG. 30 is a bar graph of storage modulus at 1 rad/s. 1.0% RADA16 (SEQ ID NO:1) was exposed to NaCl of which ionic strengths varied from 0 to 1.0 M.
Figure 31:
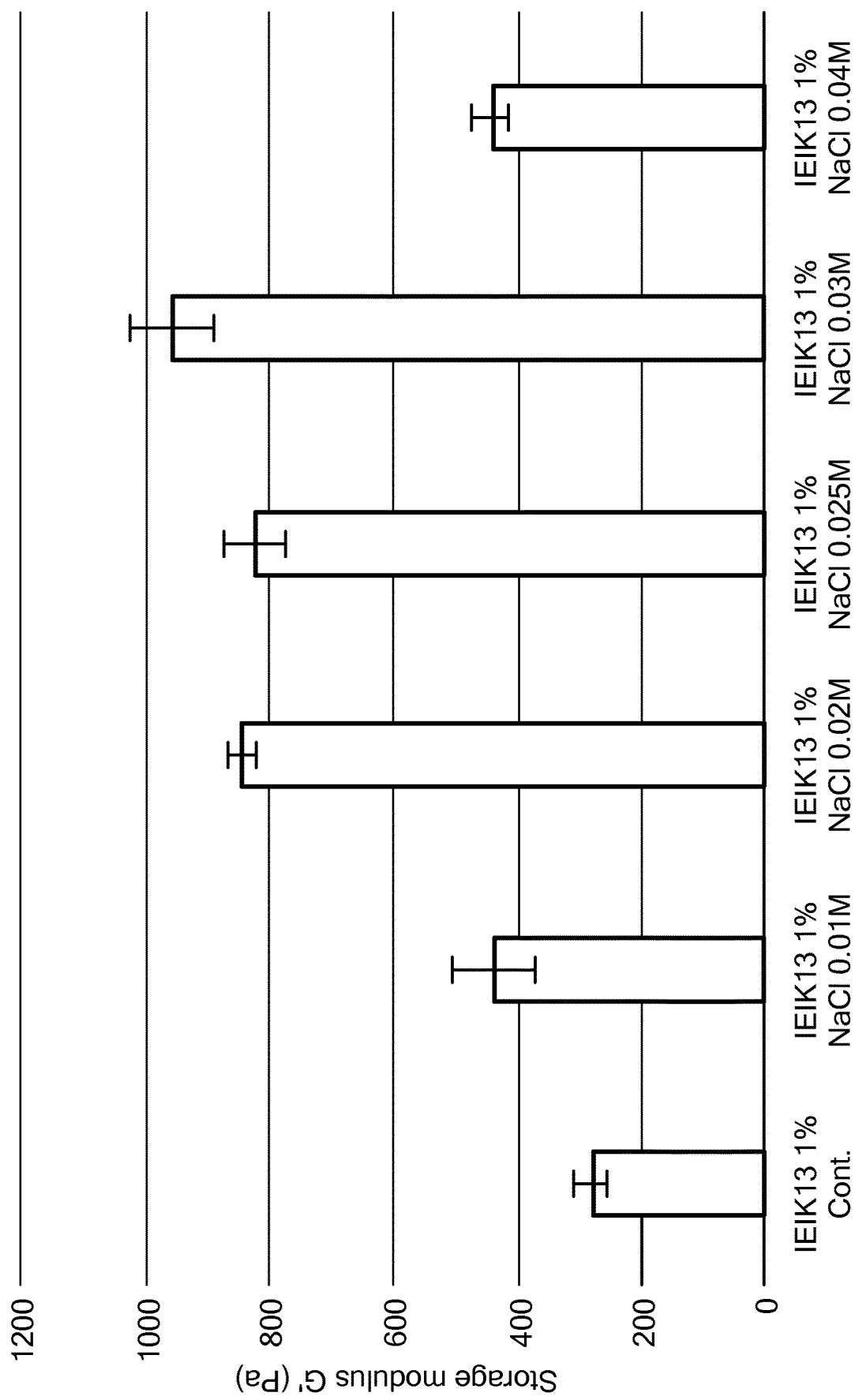
FIG. 31 is a bar graph of storage modulus at 1 rad/s. 1.0% IEIK13 (SEQ ID NO:3) was exposed to NaCl of which ionic strengths varied from 0 to 0.04 M.

Rheological properties of peptide compositions at selected ionic strengths were measured using a rheometer (DHR-1, TA Instruments) with 20 mm plates. Rheological properties of 1% RADA16 (SEQ ID NO:1) compositions were increased with ionic strength adjustment up to 0.7 M, while decreased with ionic strength higher than 0.7 M. Rheological properties of 1% IEIK13 (SEQ ID NO:3) compositions were increased with ionic strength adjustment up to 0.03 M, while decreased with ionic strength higher than 0.03 M. Results well matched with visual inspections of peptide compositions at selected salt ionic strengths. Results are shown in FIG. 30 for RADA16 (SEQ ID NO:1) and in FIG. 31 for IEIK13 (SEQ ID NO:3).

Figure 32A:
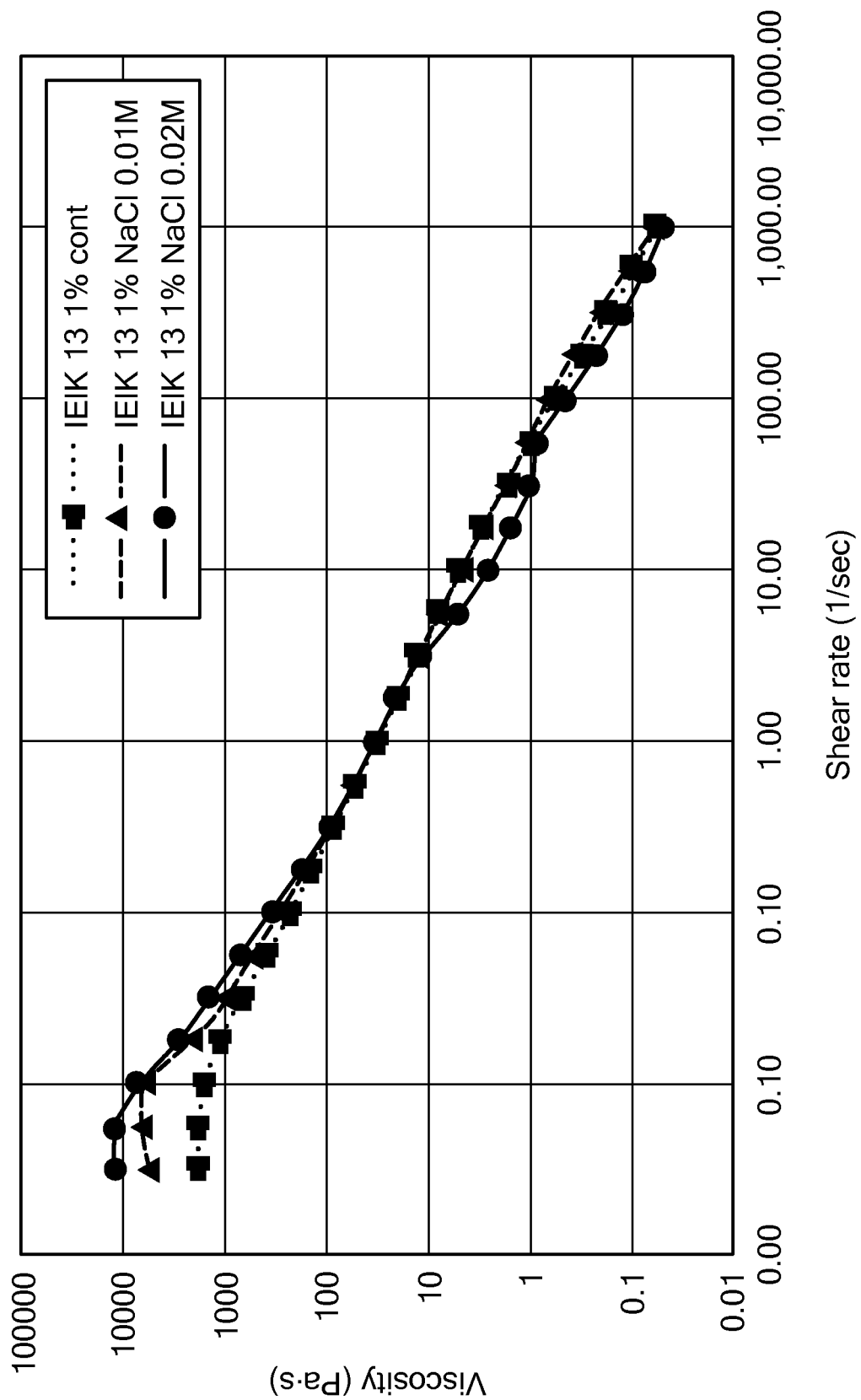
FIG. 32A shows flow viscosity tests of 1% IEIK13 (SEQ ID NO:3) at NaCl ionic strengths of 0, 0.01 and 0.02 M.
Figure 32B:
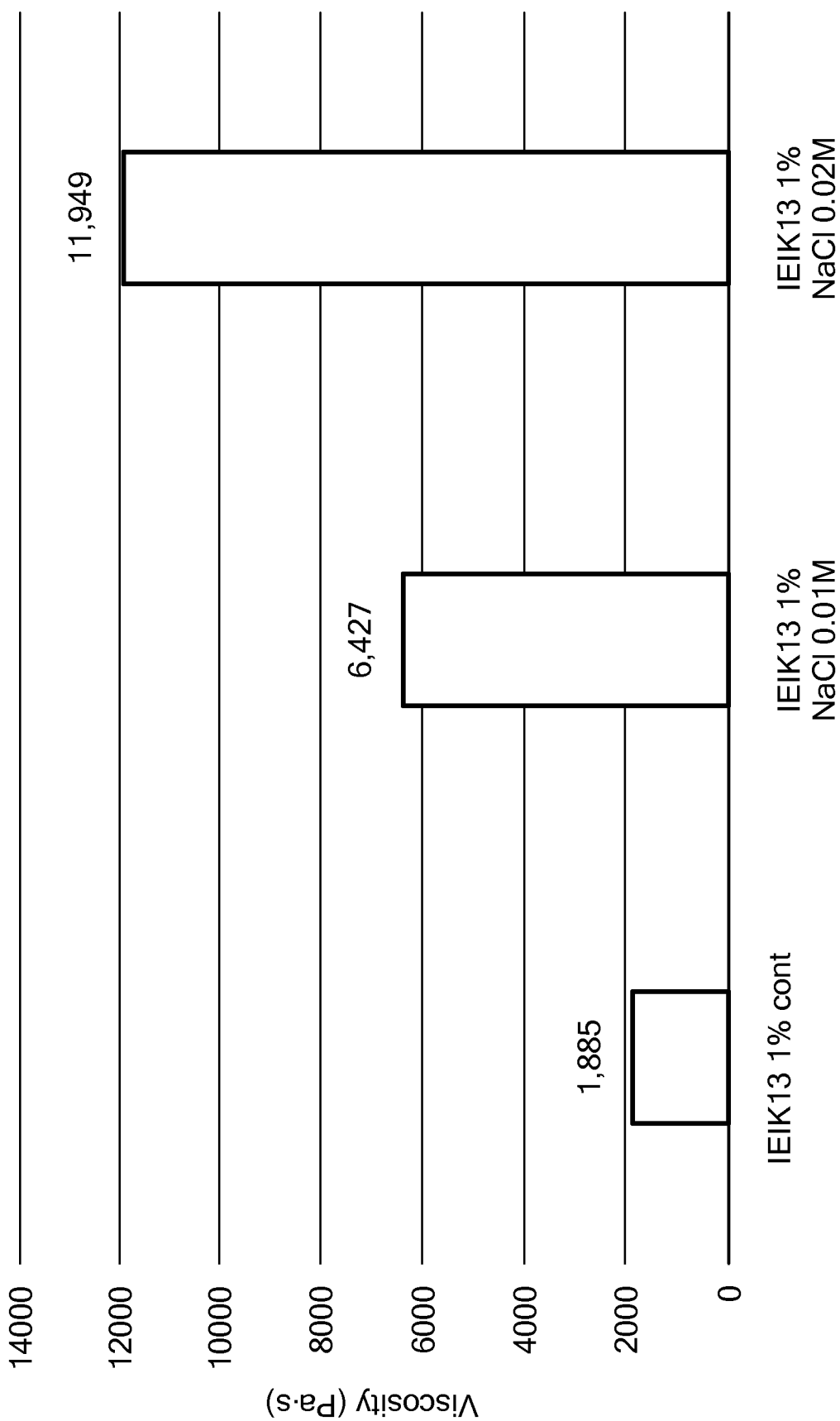
FIG. 32B is a bar graph of viscosity with the shear rate of 0.003 1/sec.

Viscosities of peptide compositions at selected ionic strength levels were evaluated. Viscosities of IEIK13 (SEQ ID NO:3) compositions were increased with the increased ionic strength. 1% IEIK13 (SEQ ID NO:3) compositions showed a typical shear thinning property. Viscosities of 1% IEIK13 (SEQ ID NO:3) compositions were evaluated using a rheometer (DHR-1, TA Instruments) with 20 mm plates. The results are shown in FIGS. 32A and 32B for IEIK13 (SEQ ID NO:3).

Figure 33A:
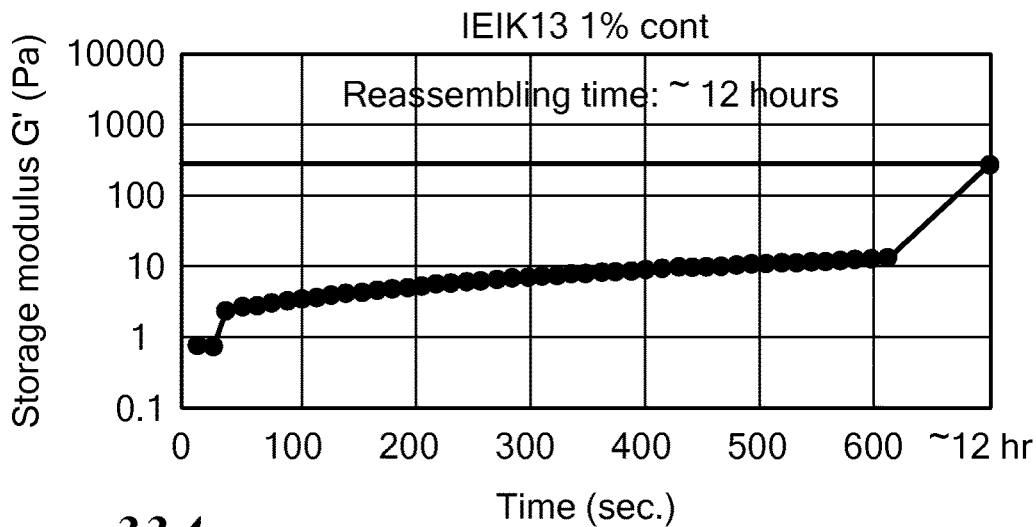
FIGS. 33A, 33B and 33C show storage modulus measurements as a function of time after applying high shear stress to 1% IEIK13 (SEQ ID NO:3) at NaCl ionic strength of 0, 0.01, and 0.02, respectively. The horizontal lines indicate the original storage moduli of each 1% IEIK13 (SEQ ID NO:3) compositions.
Figure 33B:
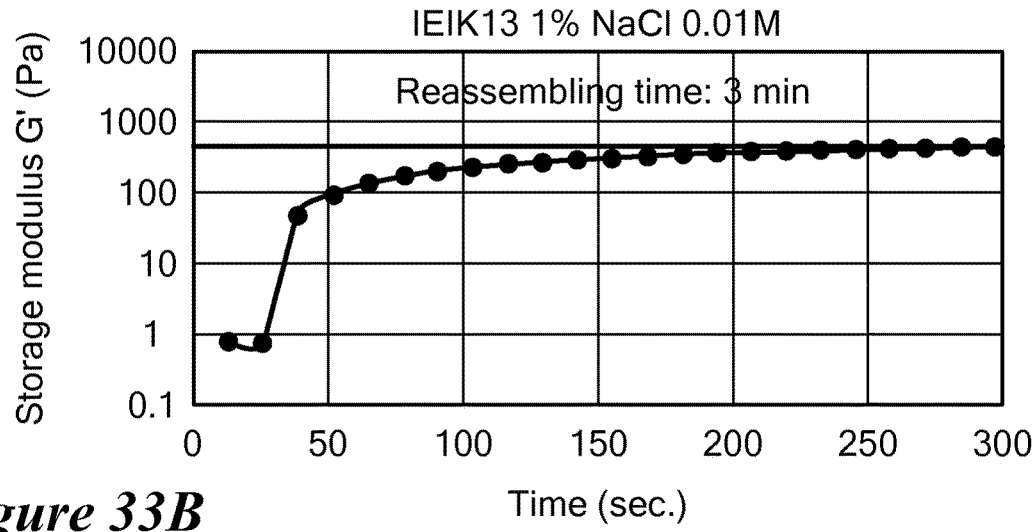
Figure 33C:
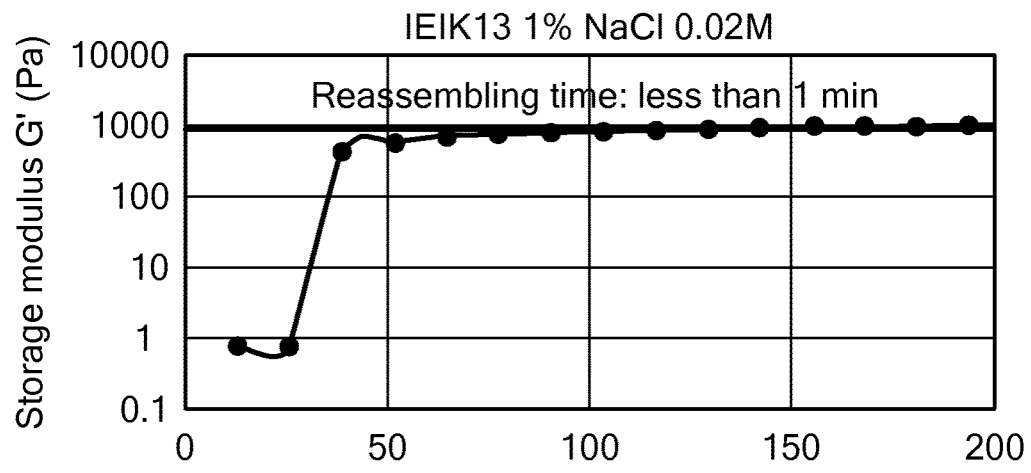

Recovery times of rheological properties were evaluated after applying high shear stress to 1% IEIK13 (SEQ ID NO:3) compositions at selected ionic strengths. Using a DHR-1 rheometer (TA Instruments), storage modulus changes of 1% IEIK13 (SEQ ID NO:3) were measured with time sweep tests at 1 rad/s at 1 Pa after applying 1000 l/sec of shear rate to samples for 1 min. IEIK13 (SEQ ID NO:3) compositions at selected ionic strengths showed a typical thixotropic behavior, recovering their rheological properties slowly. Recovery times of rheological properties are based on reassembly of peptide molecules to form nano fibers again. Complete reassembling time of 1% IEIK13 (SEQ ID NO:3) control compositions without salt addition was up to 12 hours or less, while those of IEIK13 (SEQ ID NO:3) compositions with NaCl 0.01M and 0.02M were less than 1 min-3 min. The results are shown in FIGS. 33A-33C for IEIK13 (SEQ ID NO:3).

Example 5: Rheological Properties of Peptide Compositions as a Function of Both pH and Ionic Strength The present Example describes rheological properties of peptide compositions at increased pH and ionic strength. In particular, the present Example describes effects of a physiological medium, such as a cell culture medium, on rheological properties of certain peptide compositions.

Effects of Dulbecco's modified Eagle's medium (DMEM) (pH 7.4) on rheological properties of IEIK13 (SEQ ID NO:3), KLD12 (SEQ ID NO:2), and RADA16 (SEQ ID NO:1) compositions were evaluated using a rheometer (AR500, TA Instruments) with 40 mm plates. DMEM is a cell culture medium that contains 6.4 g/L of NaCl, 3.4 g/L $NaHCO_3$ (sodium bicarbonate), minor amounts of other salts, various amino acids, and 4.5 g/L of glucose. The pH of DMEM is 7.2±0.2 and the osmolality is 335±30 mOsm/Kg $H_2O$. DMEM is close to human physiological fluids, for example, blood.

Before being mixed with the DMEM solution, 1% peptide compositions were kept in 4° C. for at least 48 hours. To perform experiments, 1 mL of peptide composition was gently pipetted and placed on the plate of the rheometer. 2 mL of the DMEM solution was gently added around the peptide composition. The peptide composition was treated with the DMEM for two minutes, then medium was removed, and the plates were placed at a measuring geometry gap at around 450 μm. Measurements were performed at 37° C. after 2 min of relaxation. Frequency tests were performed from 1 rad/s to 100 rad/s at 1 Pa of oscillation stress.

Figure 5A:
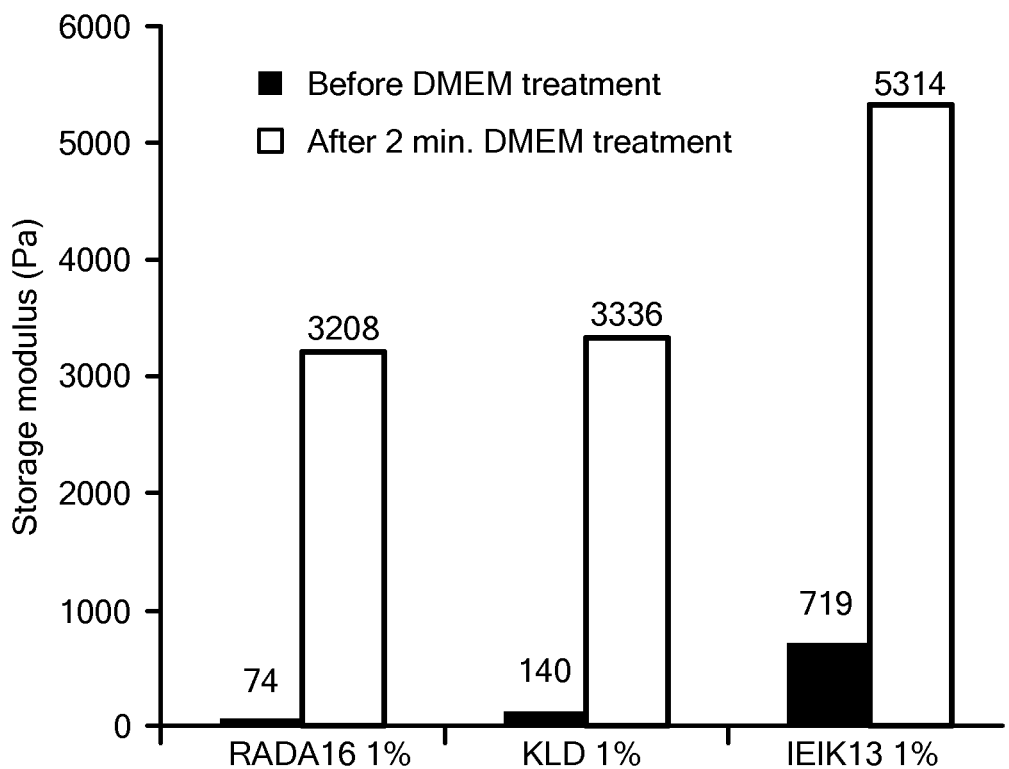
FIGS. 5A and 5B are bar graphs showing the effect of DMEM (Dulbecco's modified Eagle's medium) treatment on 1% peptide compositions.
Figure 5B:
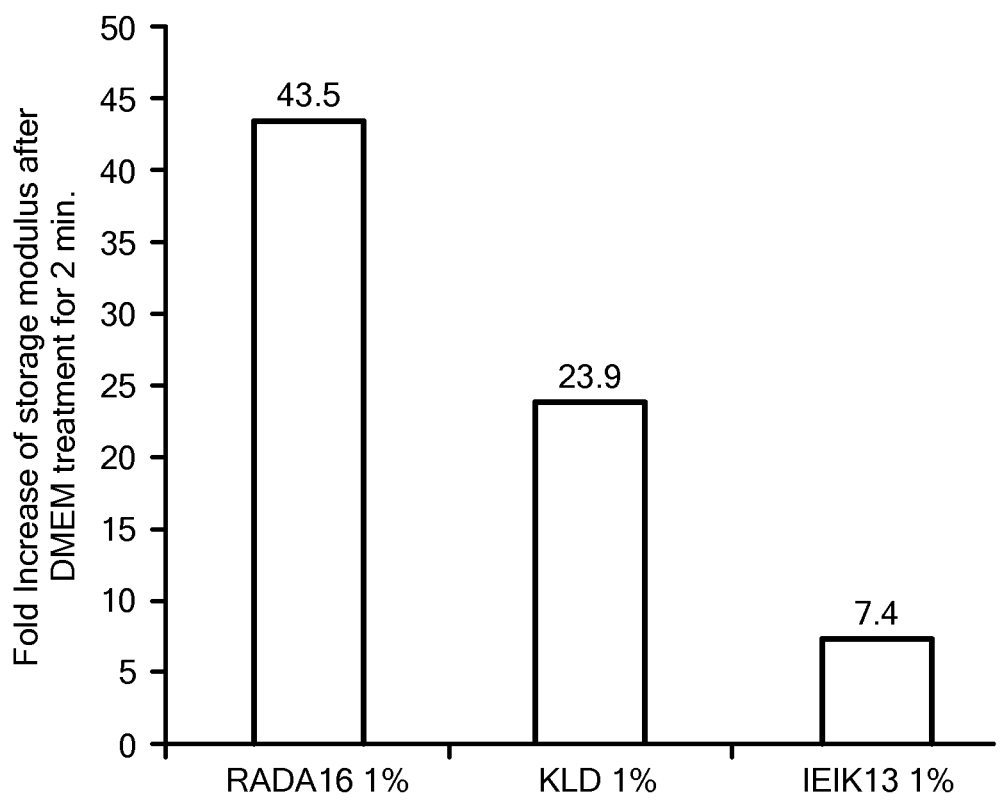

Rheological properties of 1% peptide compositions were measured before and after the DMEM treatment for 2 minutes; results are presented in FIG. 5A. The fold increase of storage moduli after the DMEM treatment is shown in FIG. 5B. As can be seen, peptide compositions showed large increases of storage moduli after DMEM treatment. Fold differences between RADA16 (SEQ ID NO:1), KLD12 (SEQ ID NO:2), and IEIK13 (SEQ ID NO:3) after the DMEM treatment were relatively small compared to that before the DMEM treatment. Similarly, stiffer peptide compositions (e.g., IEIK13 (SEQ ID NO:3)) showed lower-fold increase of storage modulus than less stiff peptide compositions (e.g., RADA16 (SEQ ID NO:1)) after the DMEM treatment. Critical intermolecular interactions were increased after the DMEM treatment, which may determine final stiffness.

Figure 22A:
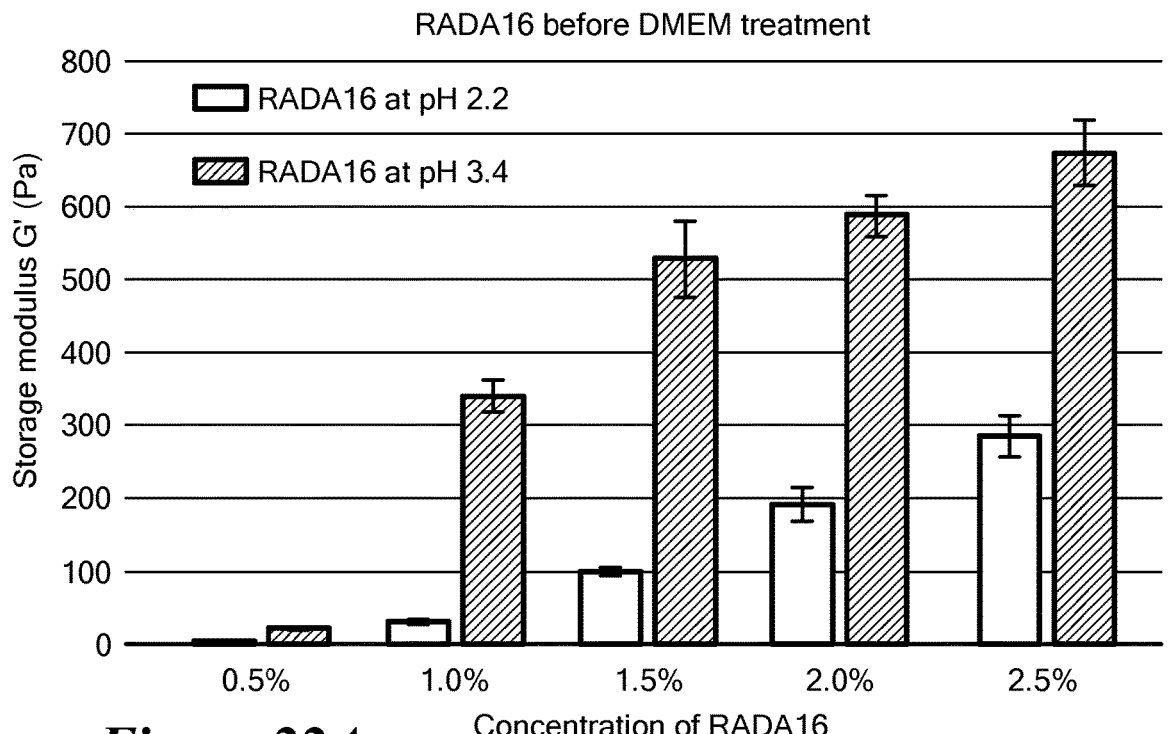
FIGS. 22A and 22B are bar graphs of storage modulus as a function of RADA16 (SEQ ID NO:1) concentration at pH 2.2 and 3.4.
Figure 22B:
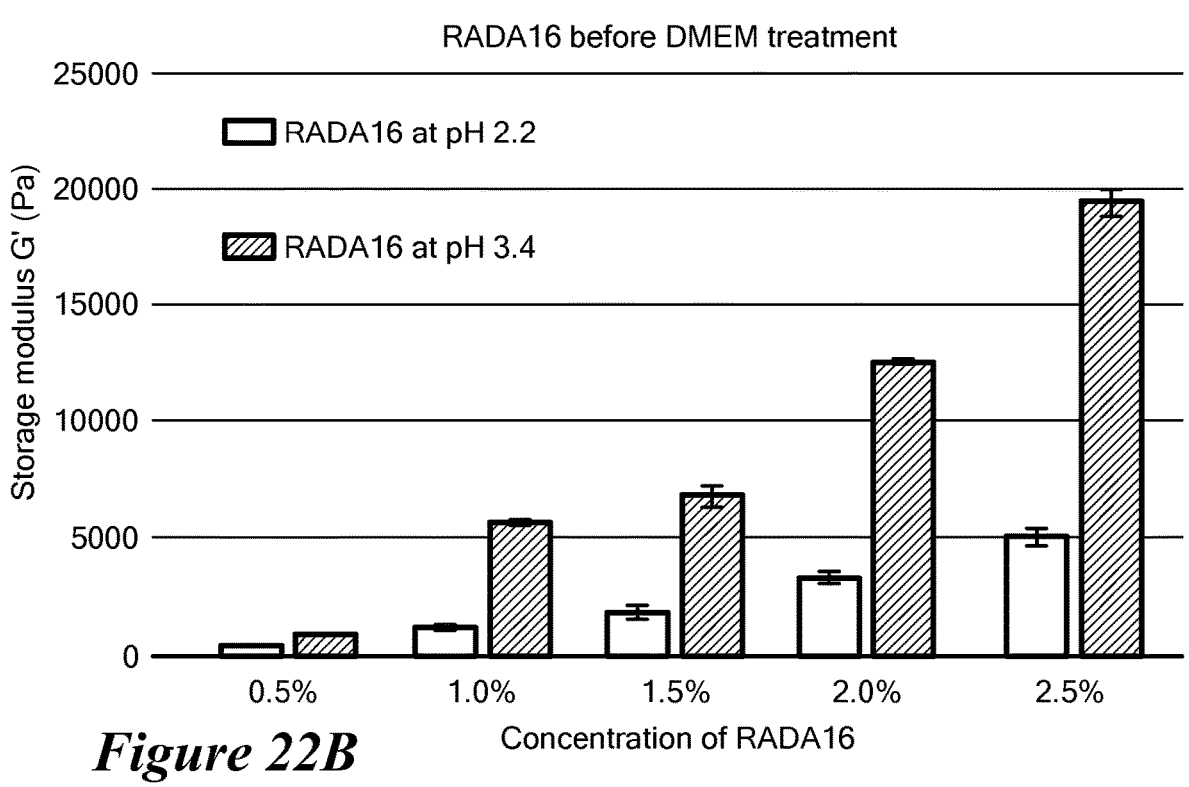
Figure 23A:
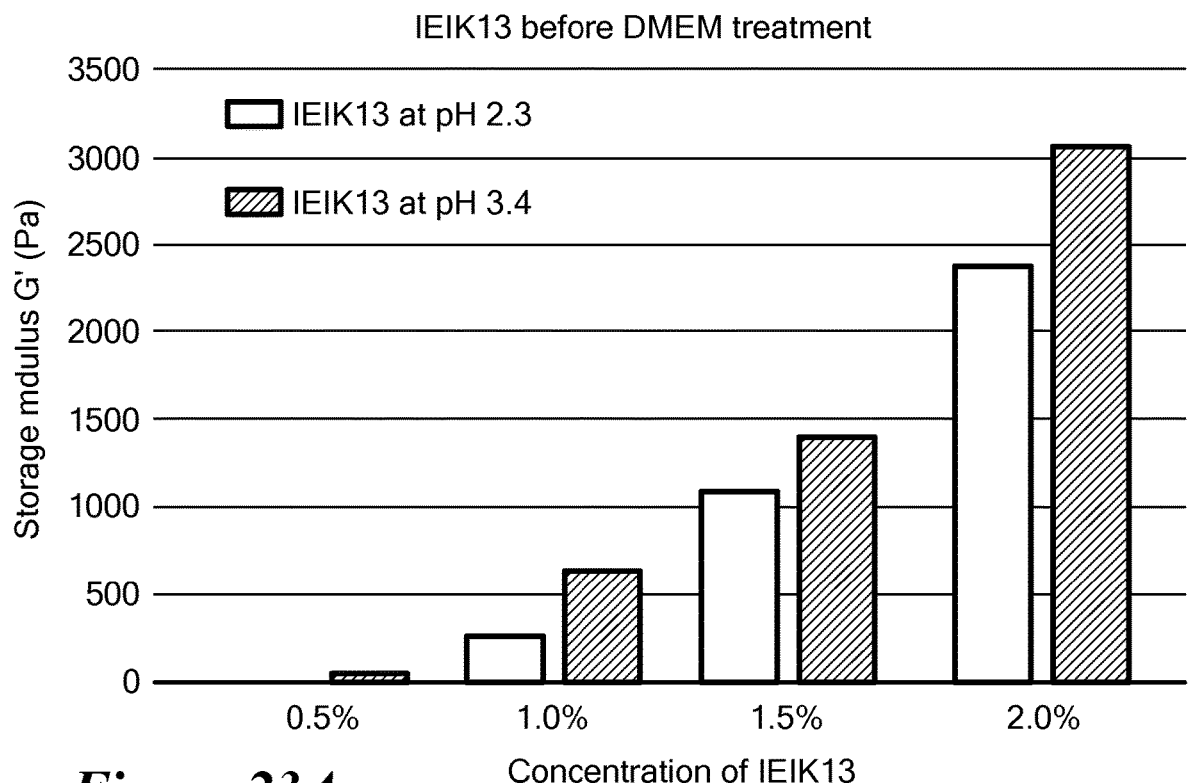
FIGS. 23A and 23B are bar graphs of storage modulus as a function of IEIK13 (SEQ ID NO:3) concentration at pH 2.3 and 3.4.
Figure 23B:
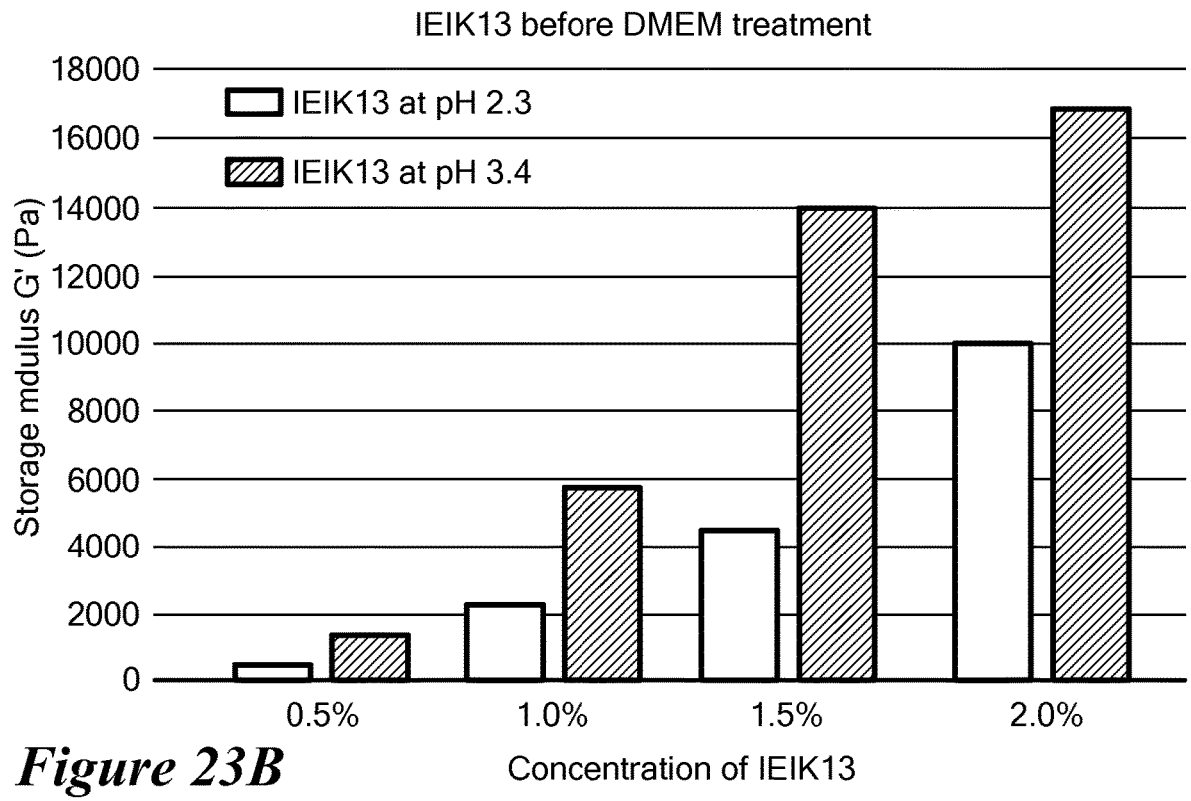

Using a DHR-1 rheometer (TA Instruments), rheological properties of peptide compositions at selected concentrations were measured before and after the DMEM treatment. Frequency sweep tests were performed from 1 rad/sec to 10 rad/sec at 1 Pa and the storage moduli in the graphs were at 1 rad/sec. Rheological properties of RADA16 (SEQ ID NO:1) and IEIK13 (SEQ ID NO:3) compositions were increased with the DMEM treatment and/or pH elevation. Results are shown in FIGS. 22A and 22B for RADA16 (SEQ ID NO:1) and FIGS. 23A and 23B for IEIK13 (SEQ ID NO:3), respectively.

Figure 34:
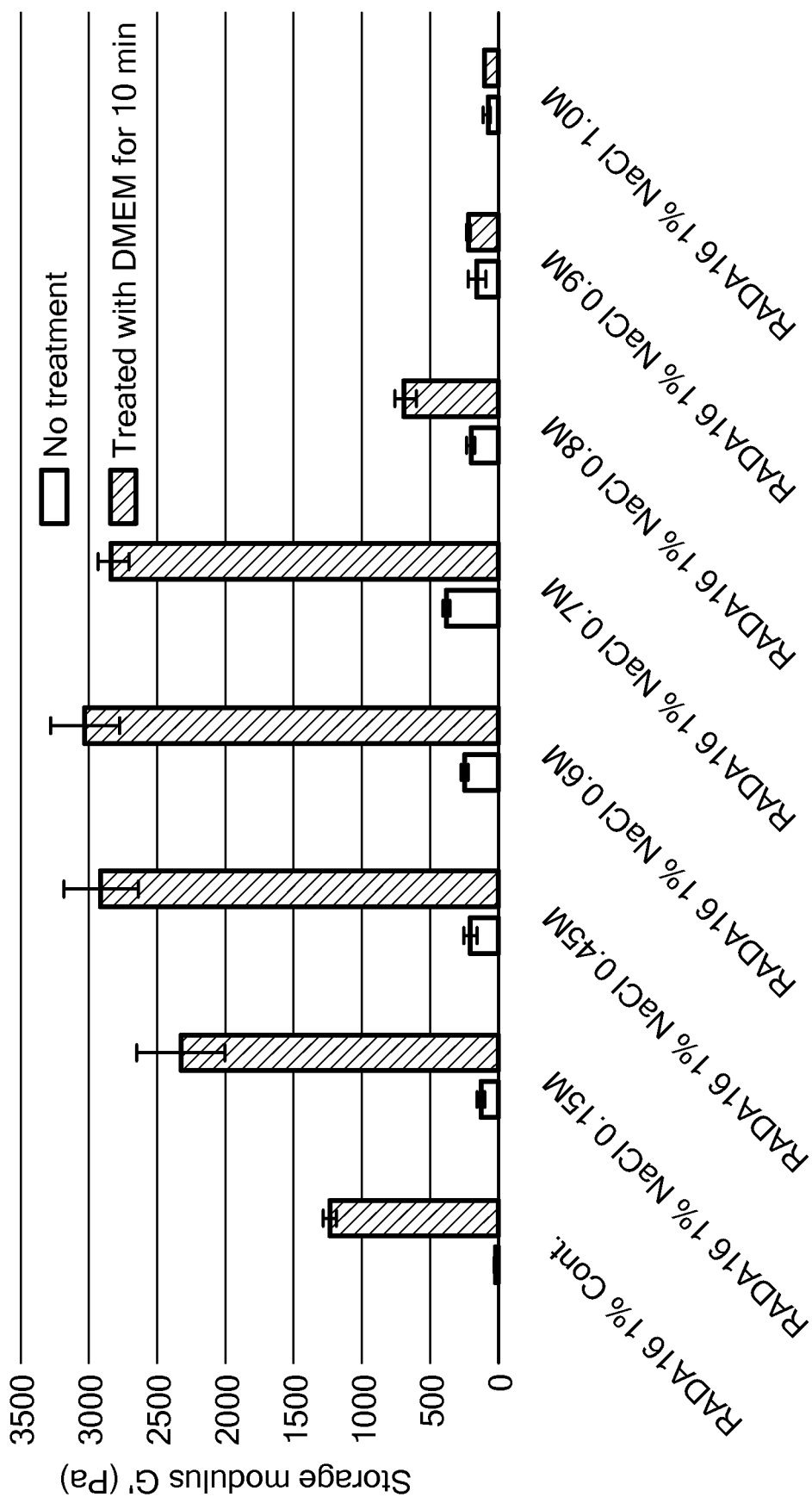
FIG. 34 shows exemplary storage moduli of 1% RADA16 (SEQ ID NO:1) at 1 Pa as a function of NaCl ionic strength before or after the DMEM treatment.
Figure 35:
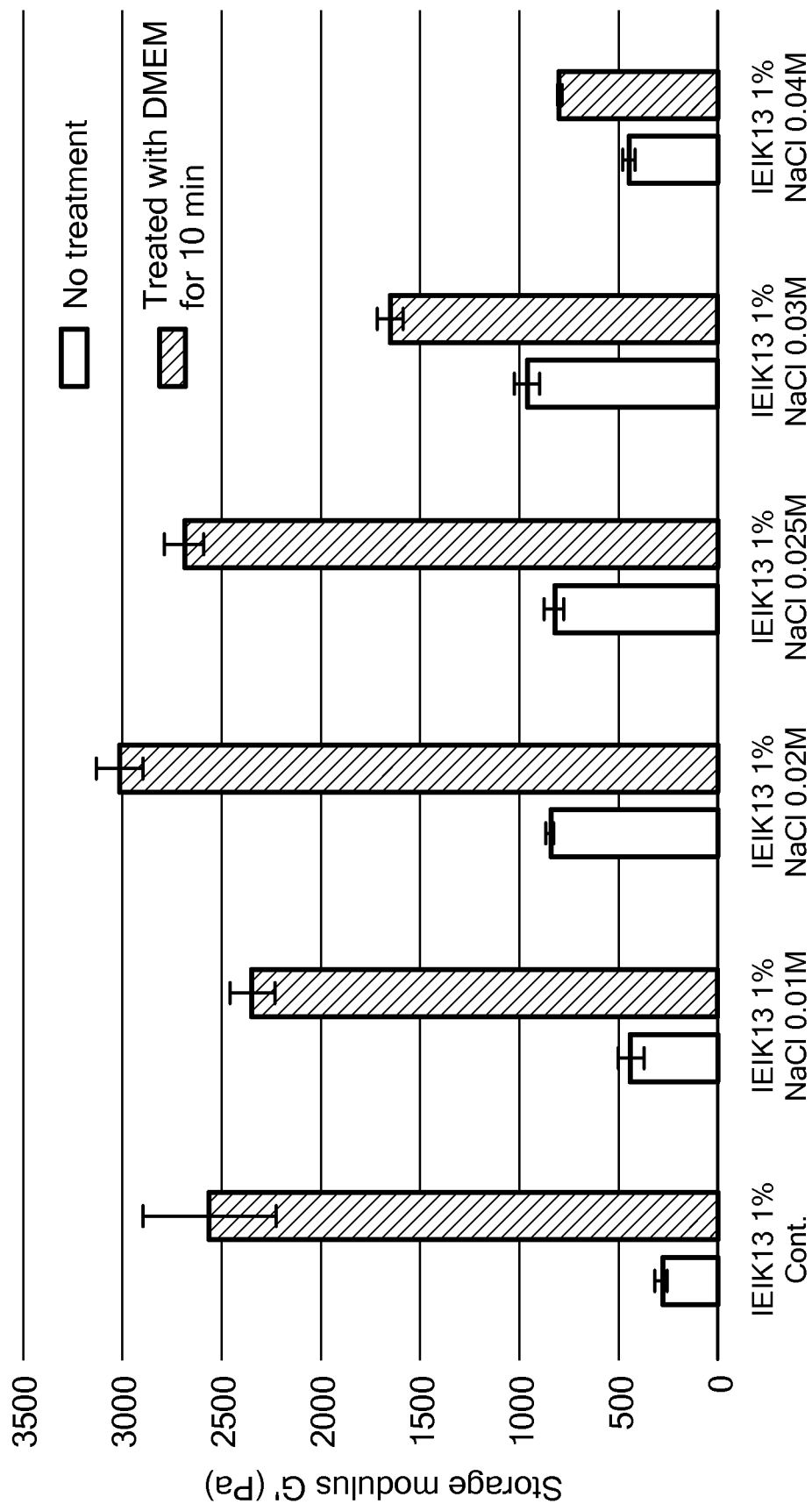
FIG. 35 shows exemplary storage moduli of 1% IEIK13 (SEQ ID NO:3) at 1 Pa as a function of NaCl ionic strength before or after the DMEM treatment.
Figure 36:
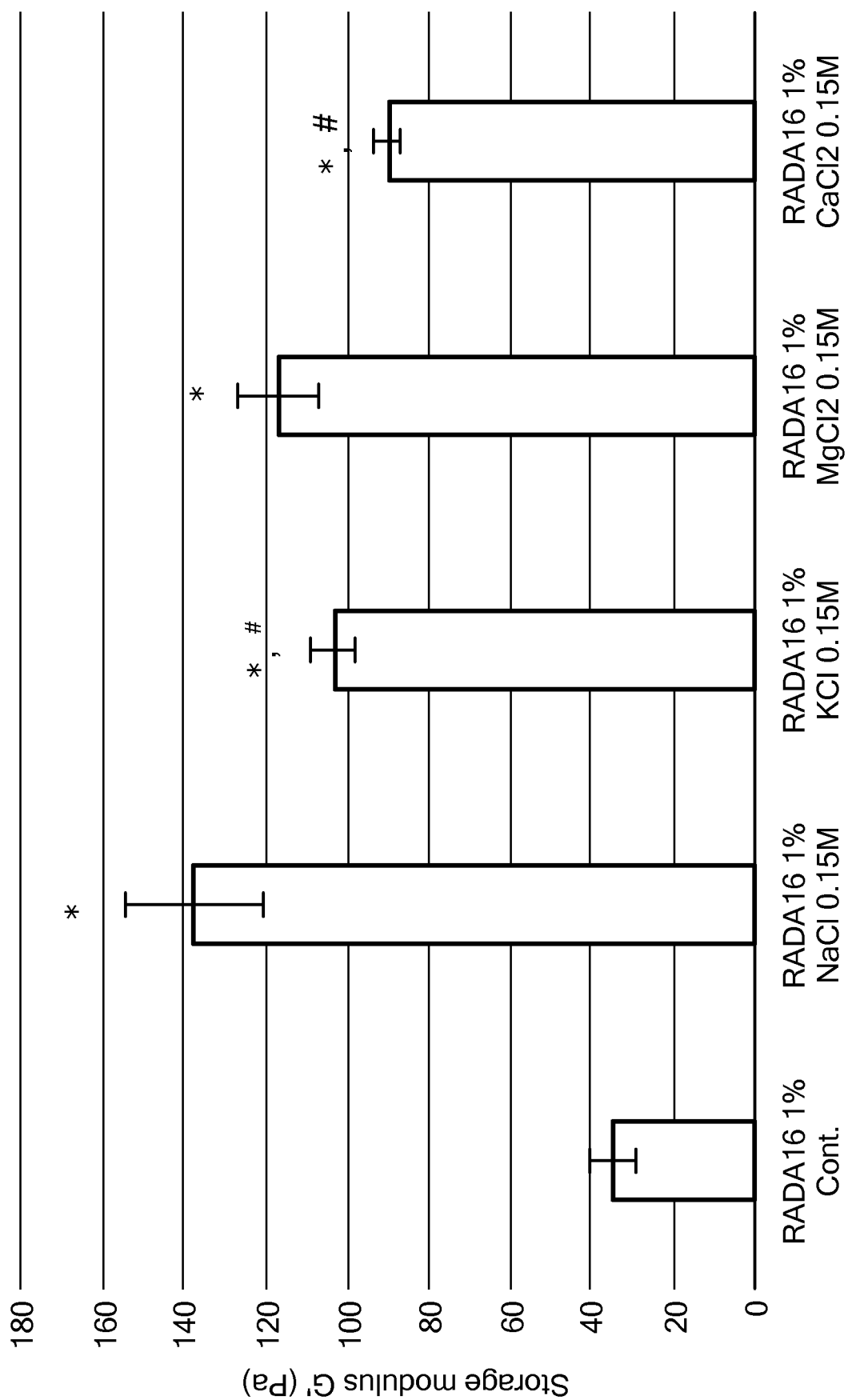
FIG. 36 shows exemplary storage moduli of 1% RADA16 (SEQ ID NO:1) with selected salts (NaCl, KCl, $MgCl_2$, and $CaCl_2$). * denotes that G' is significantly higher than control (no salt) (P<0.05). # denotes that G' is significantly lower than 1% RADA16 (SEQ ID NO:1) with NaCl ionic strength of 0.15M (P<0.05).
Figure 37:
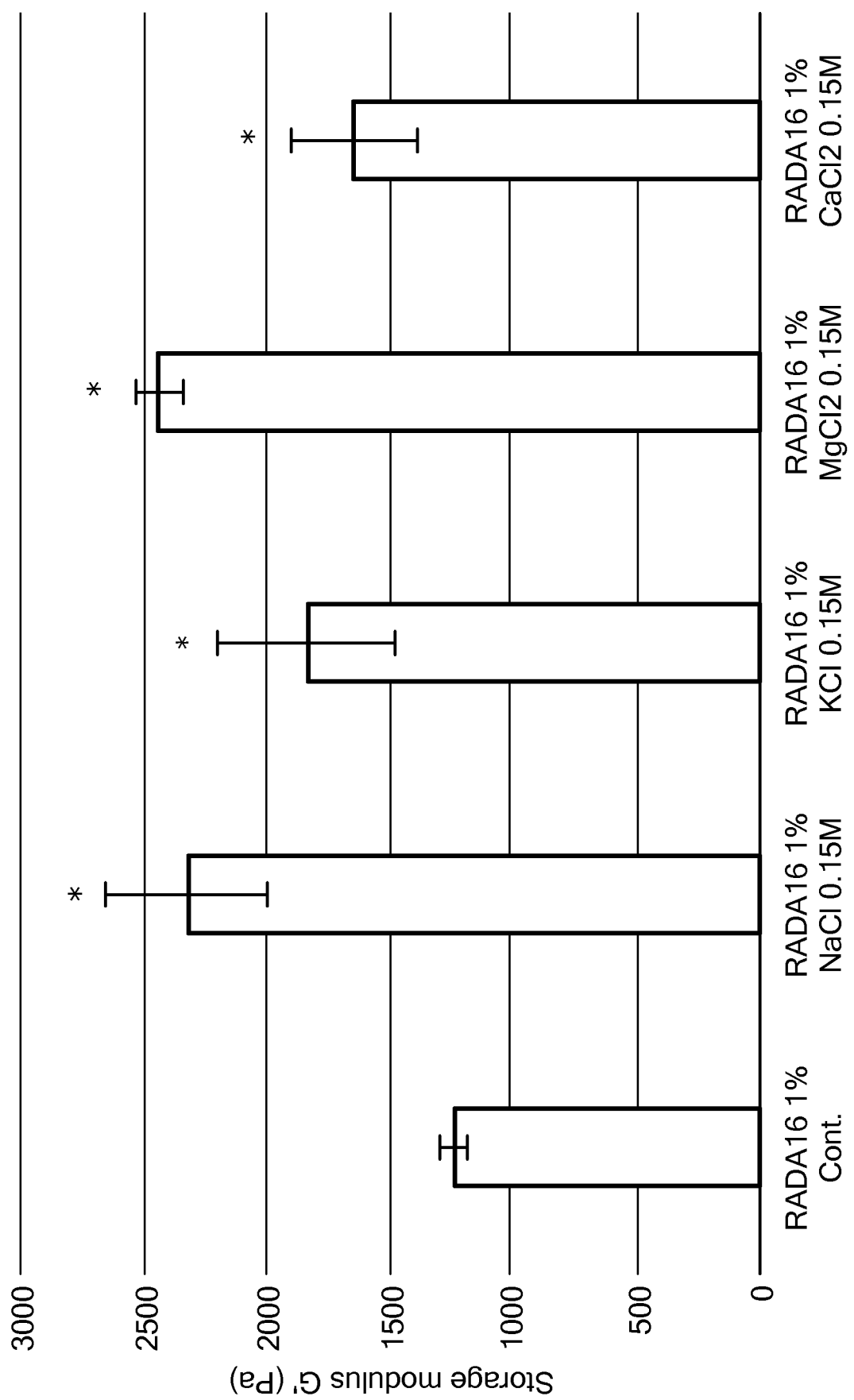
FIG. 37 shows exemplary storage moduli of 1% RADA16 (SEQ ID NO:1) with selected salts (NaCl, KCl, $MgCl_2$, and $CaCl_2$) after the DMEM treatment. * denotes that G' is significantly higher than control (no salt, after DMEM treatment) (P<0.05).
Figure 38:
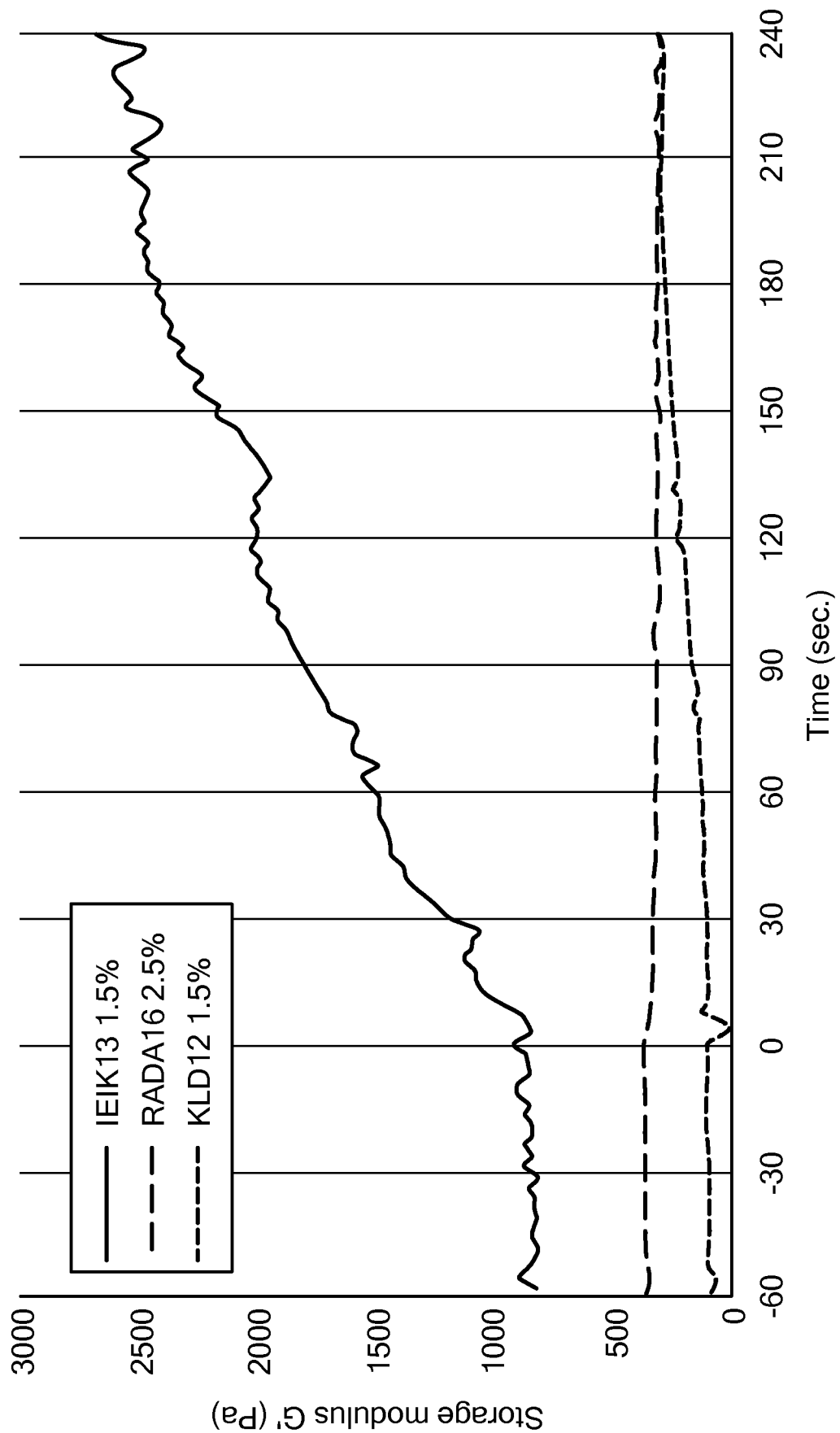
FIG. 38 shows exemplary storage modulus measurements as a function of time for 1.5% IEIK13 (SEQ ID NO:3), 1.5% KLD12 (SEQ ID NO:2), and 2.5% RADA16 (SEQ ID NO:1) after the saline buffer treatment. Time sweep tests were performed at 1 rad/sec and at 1 Pa with 20 mm plates and 500 μm gap distance. During time sweep tests, the saline buffer was added into the chamber surrounding the measuring plates to soak the peptides at time=0.
Figure 39:
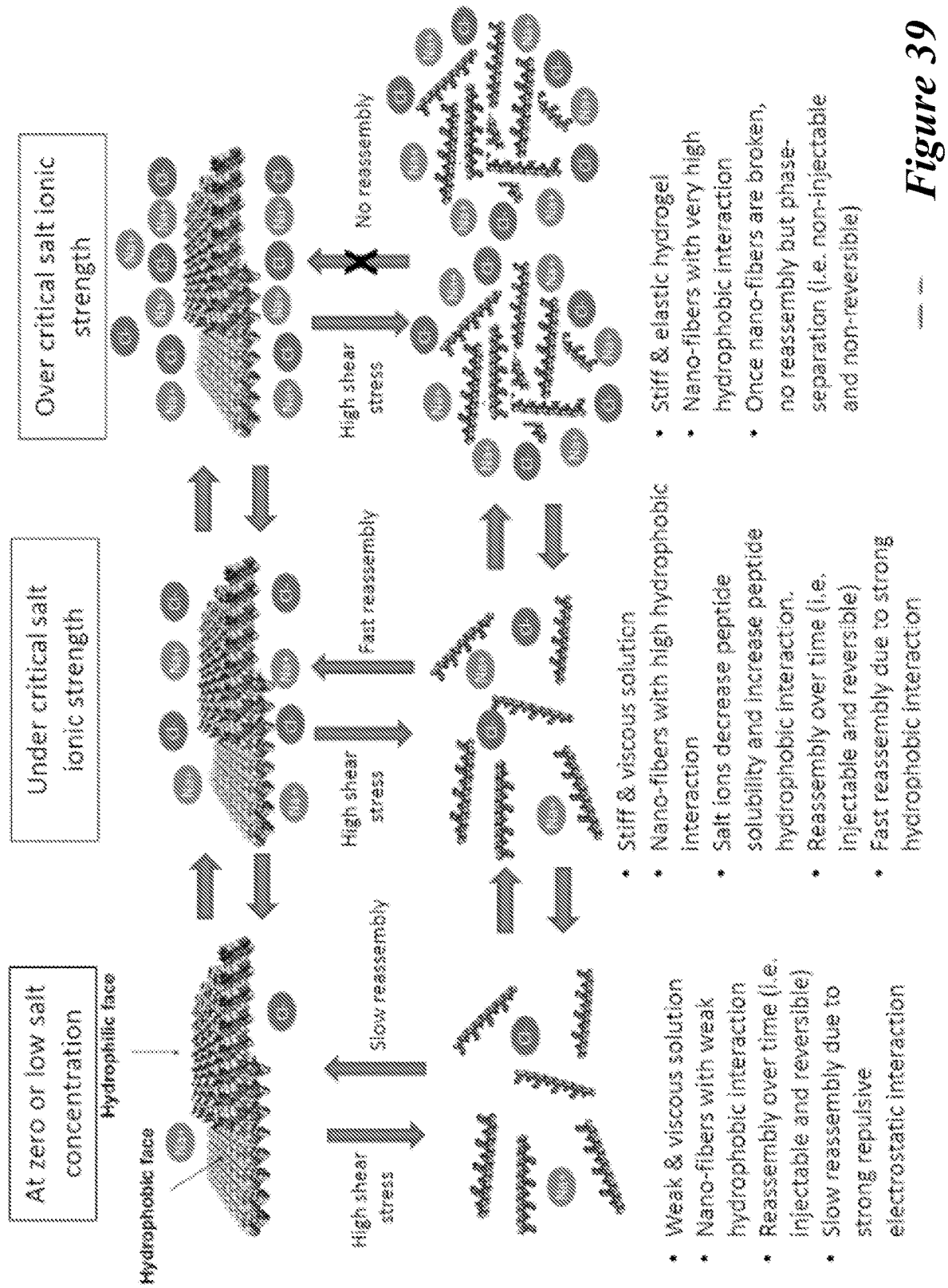
FIG. 39 illustrates nanostructures and/or reassembly of RADA16 (SEQ ID NO:1), KLD12 (SEQ ID NO:2), and IEIK13 (SEQ ID NO:3), at certain ionic strengths. High shear stress may change the nanostructures and/or reassembly.

Using a DHR-1 rheometer (TA Instruments), rheological properties of peptide compositions at selected ion strengths were evaluated 10 mins after the DMEM treatment. Frequency sweep tests were performed from 1 rad/sec to 10 rad/sec at 1 Pa and the storage modulus at 1 rad/sec was selected for data. Rheological properties of RADA16 (SEQ ID NO:1) compositions were increased with ionic strength adjustment up to 0.7 M, while they were decreased with 0.7 M or higher. At 0.9 M or higher ionic strengths of NaCl, RADA16 (SEQ ID NO:1) compositions became cloudy. Rheological properties of RADA16 (SEQ ID NO:1) did not change with the DMEM treatment (e.g. no gelation). However, rheological properties of IEIK13 (SEQ ID NO:3)

compositions were increased with the DMEM treatments at selected ionic strengths. Results are shown in FIG. 34-35.

Figure 40:
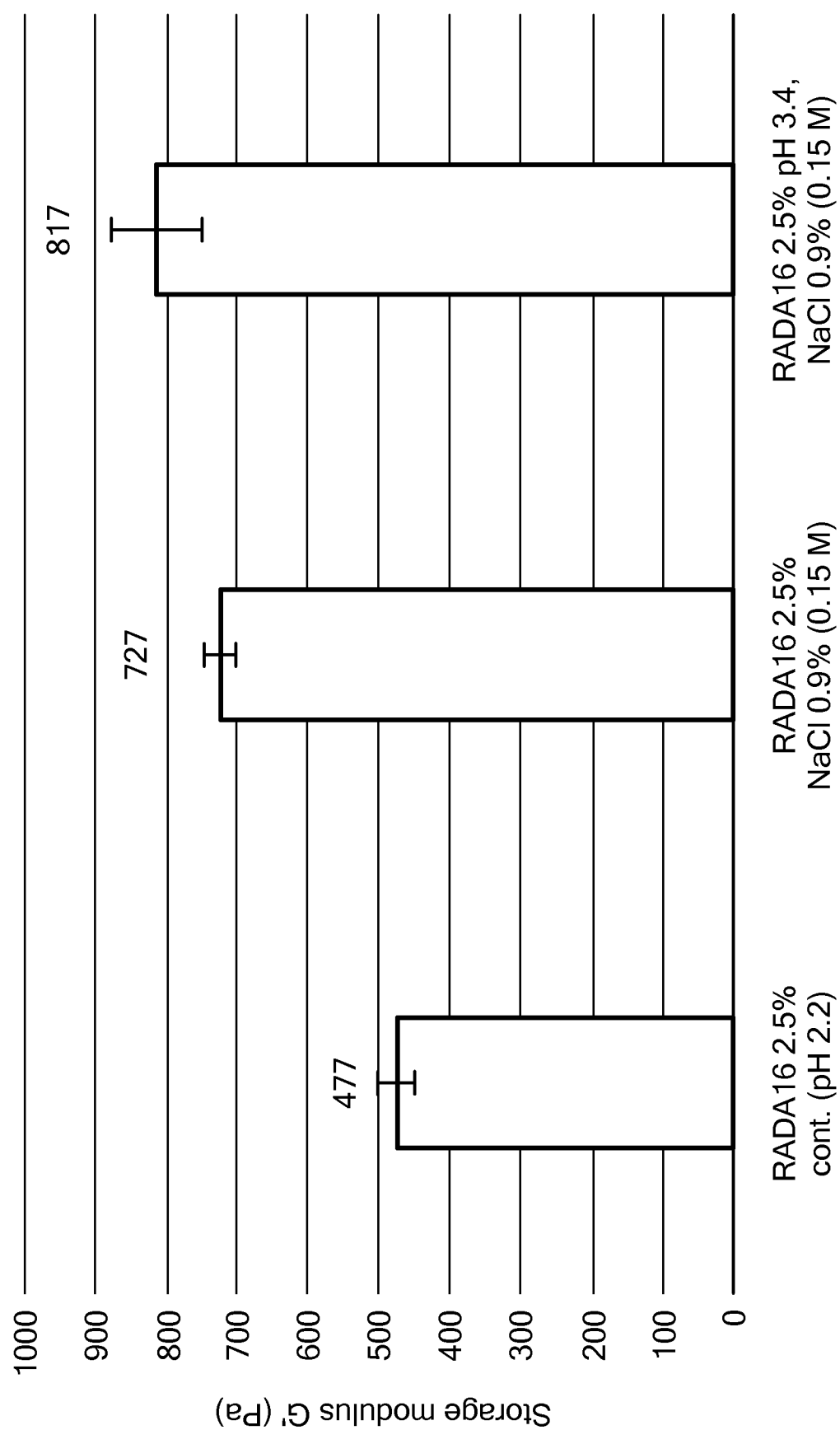
FIG. 40 shows storage moduli of 2.5% RADA16 (SEQ ID NO:1) at 1 rad/sec. NaCl addition and pH elevation increased storage moduli of 2.5% RADA16 (SEQ ID NO:1).
Figure 42C:
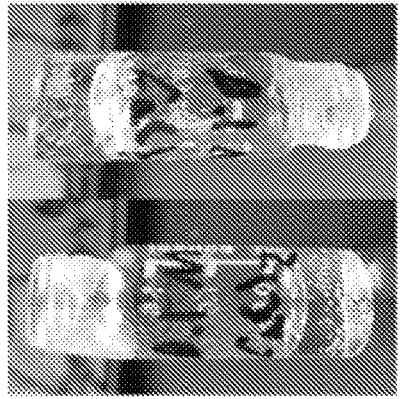
Figure 42B:
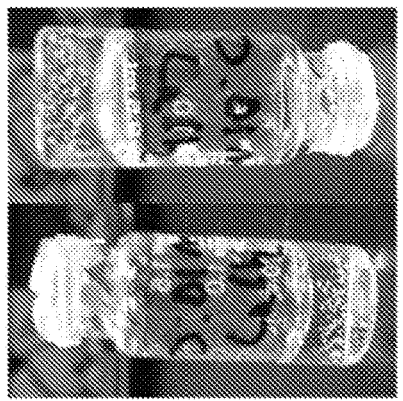
Figure 42A:
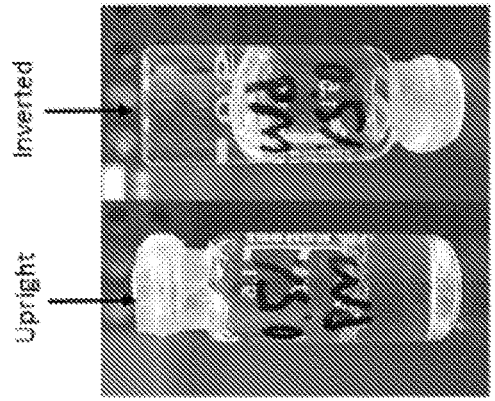
Figure 42G:
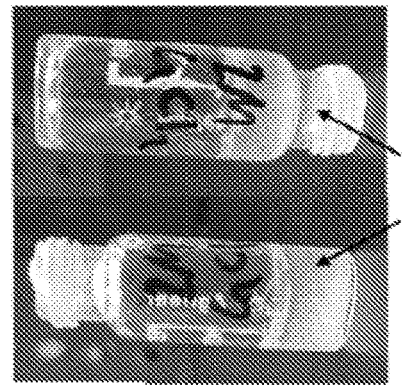

IEIK13 (SEQ ID NO:3), KLD12 (SEQ ID NO:2), and RADA16 (SEQ ID NO:1) were dissolved in salt buffer (e.g. NaCl) and kept at elevated pH level adjusted with alkali salt buffer (e.g. NaOH). The compositions had their pH levels about 2.5-4.0 and lower ionic strength than their critical points. With respect to RADA16 (SEQ ID NO:1), KLD12 (SEQ ID NO:2) and IEIK13 (SEQ ID NO:3), peptide compositions were still clear with 0.9% NaCl (i.e. ionic strength of 0.15 M) at pH 3.4 (adjusted with NaOH). Rheological properties of RADA16 (SEQ ID NO:1) with 0.9% NaCl at pH 3.4 were stiffer than those of RADA16 control (i.e. no ionic strength and pH elevation) and RADA16 (SEQ ID NO:1) with 0.9% NaCl (no pH elevation). Results are shown in FIG. 40.

A Congo Red assay was performed to determine gel formation of peptide compositions in a PBS (Phosphate buffered saline) solution (pH 7.4), as shown in FIG. 1. 100 µl of each gel at selected concentrations were plated on a glass slide. After 30 seconds, 500 µl of 1% Congo Red solution was added around and on top of each of the composition aliquots and then the excess Congo Red solution was wiped off prior to examination. RADA16 (SEQ ID NO:1), IEIK13 (SEQ ID NO:3), and KLD12 (SEQ ID NO:2) were plated at selected concentrations of 0.5%, 1.0%, 1.5%, 2.0% and 2.5%. Visual observation determined the success or failure of gelation at each concentration. RADA16 (SEQ ID NO:1), IEIK13 (SEQ ID NO:3), and KLD12 (SEQ ID NO:2) gelled at all concentrations.

Example 6: Cell Viability

The present Example describes ability of certain peptide compositions to support cell viability. In some embodiments, provided peptide compositions are characterized in that they support high cell viability, particularly as compared with appropriate reference compositions.

Figure 14:
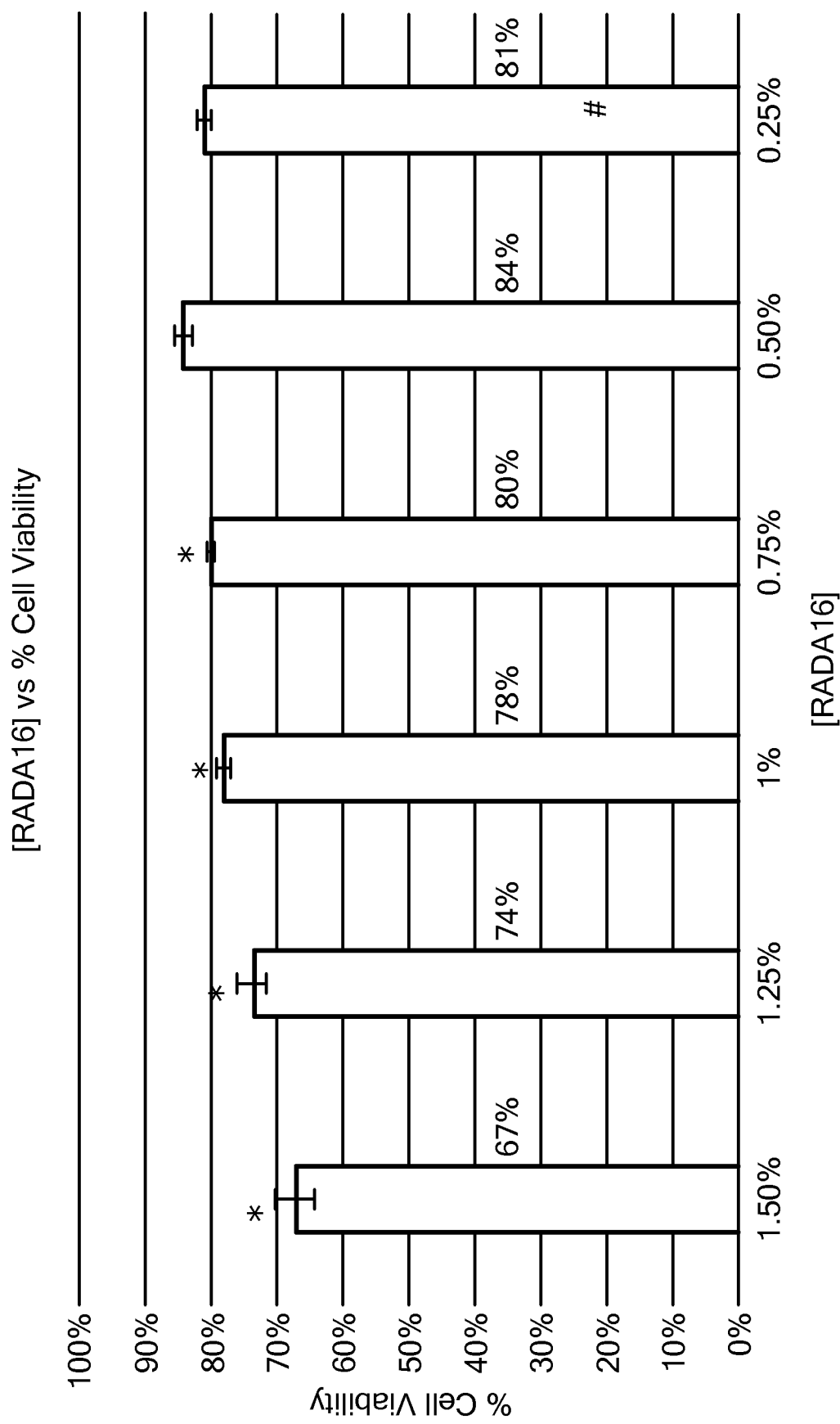
FIGS. 14-16 show cell viabilities (mMSCs) of RADA16 (SEQ ID NO:1), IEIK13 (SEQ ID NO:3) and KLD12 (SEQ ID NO:2), respectively, at selected concentrations. * is denoted that the cell viability is significantly lower than the cell viability at next left column (p-value<0.05). # is denoted that the cell viability is significantly higher than the cell viability at next left column (p-value<0.05).
Figure 15:
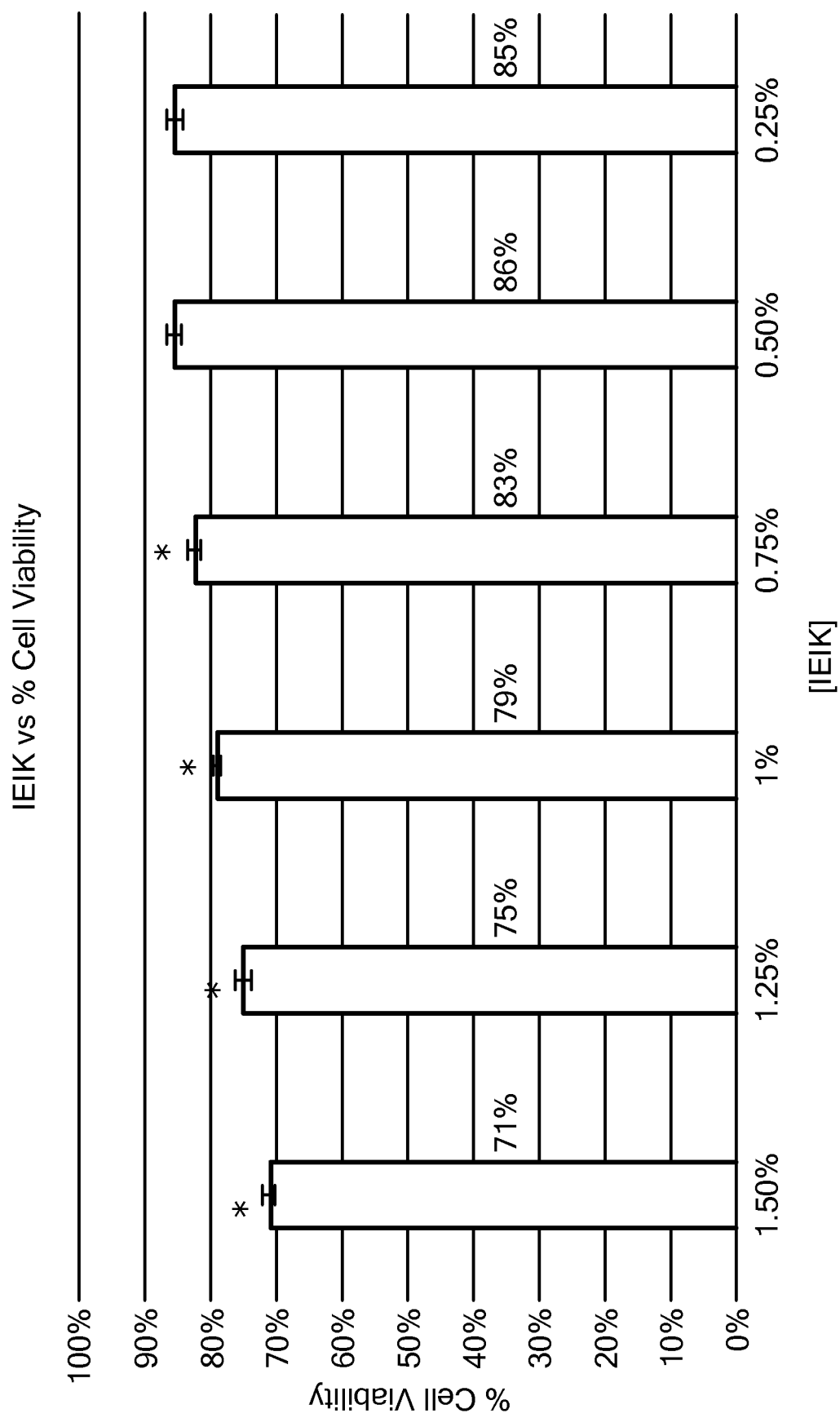
Figure 16:
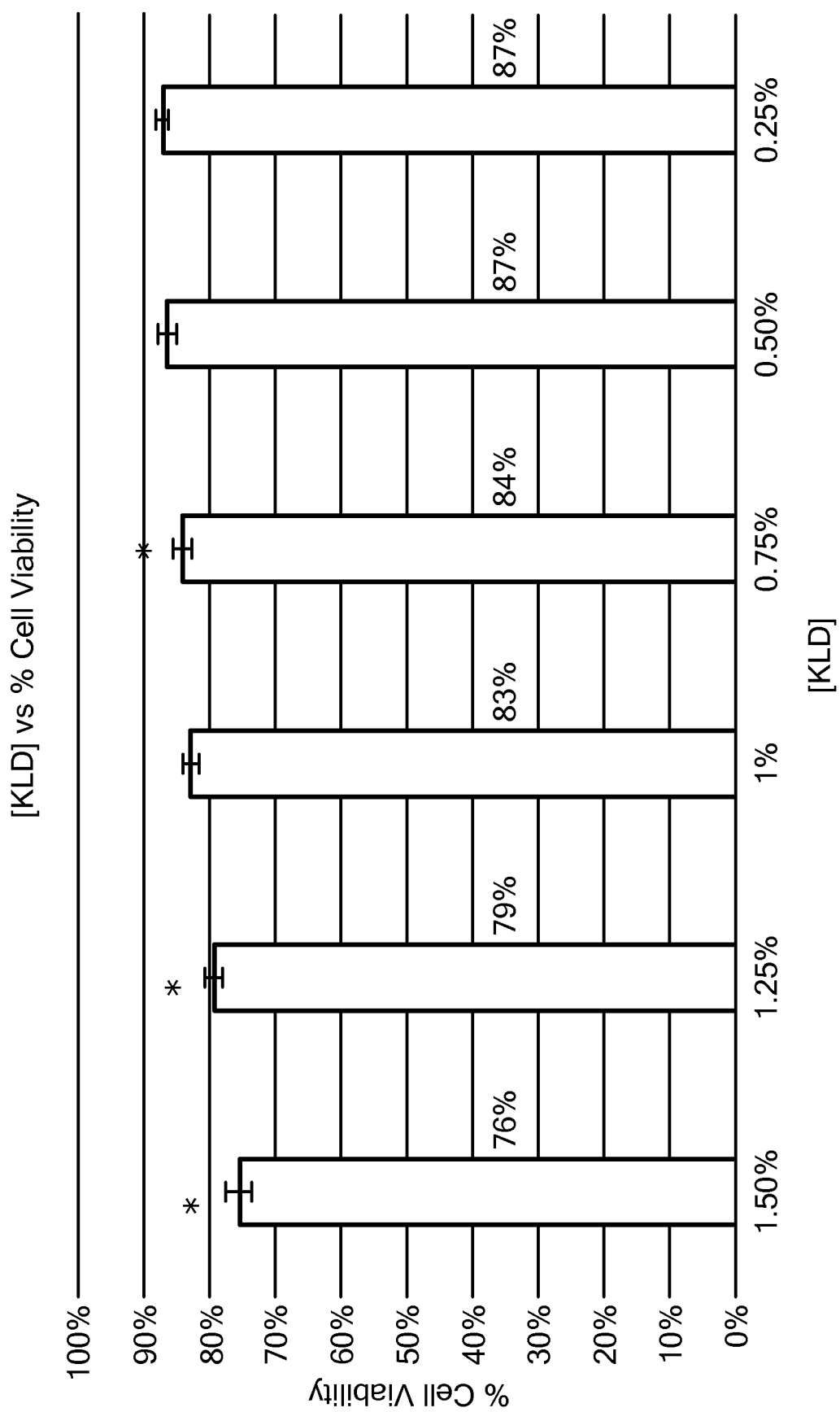

A cell viability (cytotoxicity) assay was performed to measure the viability of C57 BL/6 Mouse Mesenchymal Stem Cells (mMSCs) with IEIK13 (SEQ ID NO:3), KLD12 (SEQ ID NO:2) and RADA16 (SEQ ID NO:1) compositions as described herein. mMSCs are a frequently used cell line in hydrogel tissue culture systems. Peptide compositions were prepared at a concentration of 2.5%, and then were diluted to concentrations of 1.5%, 1.25%, 1.0%, 0.75%, and 0.50% with sucrose. The final concentration of sucrose was 10%. Cells were washed and re-suspended in 10% sucrose to a final concentration of 5 million cells/ml. Cells were centrifuged and the supernatant was removed. The cells were re-suspended in peptide compositions with 10% sucrose. The protocol was then followed for plating drop cultures and subsequent isolation as described in the PuraMatrix® Guidelines for Use (BD/Corning website). Results are shown in FIGS. 14-16 for RADA16 (SEQ ID NO:1), IEIK13 (SEQ ID NO:3), and KLD12 (SEQ ID NO:2), respectively.

The cell viabilities in IEIK13 (SEQ ID NO:3) and KLD12 (SEQ ID NO:2) compositions at 0.5% were similar to those at 0.25%. Cell viability in RADA16 (SEQ ID NO:1) compositions at 0.5% is significantly higher than that at 0.25%. However, cell viabilities significantly decreased when the concentrations of peptides were over 0.75%. KLD12 (SEQ ID NO:2) and IEIK13 (SEQ ID NO:3) compositions showed similar or higher cell viability compared to RADA16 (SEQ ID NO:1) at all tested concentrations within the range 0.25% to 1.5%. The order of overall cell viability among these peptide compositions was KLD12 (SEQ ID NO:2)>IEIK13 (SEQ ID NO:3)>RADA16 (SEQ ID NO:1). The tested peptide compositions with concentrations of 0.75% or less showed cell viabilities higher than 80%.

Example 7: Rheological Properties of RADA16 Compositions with Different Salts

The present Example describes, among other things, studies that achieved controlled mechanical enhancement of self-assembling peptide gels while still maintaining gel reversibility (e.g., without compromising gel formation and its mechanical integrity post mechanical perturbation). These described studies also achieved control of gelation kinetics through mixing of cations and anions at selected concentrations in combination with various self-assembling peptides, most notably, RADARADARADARADA (or RADA-16 (SEQ ID NO:1)).

The present Example, particularly when taken in context with the present specification, confirms that parameters have been defined that permit peptide compositions to be specifically formulated to have material and/or rheological characteristics particularly useful for certain applications. For example, the technology described herein permits preparation of self-assembling peptide compositions that are specifically tailored to function well as sealants (which may require or benefit from, for example, enhanced stiffness), lubricants (which may require or benefit from, for example, enhanced kinetics), drug mixtures (which may require or benefit from, for example, reversibility and enhanced kinetics), injectables (which may require or benefit from, for example, reversibility), etc. Alternatively or additionally, technology described herein permits preparation of peptide compositions and/or selection of parameters included in or applied to them, that can assist in general handling and/or manufacture of useful peptide compositions and/or devices that include them.

For example, as demonstrated herein, by systematically controlling the type, e.g. Na, K, and Ca, and/or concentration of cation included in self-assembling peptide compositions, the mechanical strength (i.e. the stiffness) can be adjusted while still maintaining reversibility and gelation kinetics. Alternatively or additionally, by systematically controlling the type e.g. Cl, SO4, PO4, and/or concentration of anion, the gelation kinetics can be controlled while maintaining reversibility.

As demonstrated in the present Example, in some embodiments (and in particular, in embodiments that utilize a RADA16 (SEQ ID NO:1) peptide), Ca will allow for greater enhanced stiffness in peptide gels compared to Na and K. In addition, in some embodiments (and in particular, in embodiments that utilize a RADA16 (SEQ ID NO:1) peptide), Cl will allow for faster gelation kinetics in peptide gels compared to SO4. Moreover, in some embodiments (and in particular, in embodiments that utilize a RADA16 (SEQ ID NO:1) peptide), CaCl2 will allow for optimally mechanically enhanced reversible gels at a concentration of ≥0.125 and <0.500 M. In the particular studies reported in this Example, concentrations≥0.500 M compromised the mechanical properties of certain gels, or rendered them unusable to post-gelation mechanical perturbations.

In general, findings reported in the present Example demonstrate that, through the use of a variety of salts and salt concentrations, attributes such as stiffness, gelation kinetics, and reversibility of gelation can be determined by selection of parameters such as concentration of peptide, identity (e.g., amino acid sequence) of peptide, concentration of cations/anions, identity of cation/anion, etc. It has been observed that both cation and anion, independently and in combination, can impact attributes. Teachings provided by the present disclosure, including the present Example, provide a system for tailoring peptide mixtures in accordance with desired attributes (e.g., performance characteristics), for example as may be appropriate for a particular application or situation.

The present Example specifically demonstrates that certain particular types of cations and/or anions, and/or concentrations thereof/have desired beneficial effects; among other things, the present Example defines such anions/cations and concentrations with respect to the exemplified contexts, and moreover provides a framework permitting those skilled in the art to do the same for other cases (e.g., other peptides, etc.).

The present Example particularly and surprisingly identifies a problem with current strategies for providing useful compositions of self-assembling peptides. That is, it has been theorized that the capacity for self-assembly is dependent on the amount of charged groups available for attack by ionic salts, which is the peptide's capacity for saturation [P. Chen. (2005). "Self-assembly of ionic-complementary peptides: a physicochemical viewpoint." Colloids and Surfaces]. However, the present Example documents that, in at least some cases, peptides are not proportionally affected by salt concentration, and thus, the mechanical properties and the reversibility do not increase linearly and are not rate dependent.

FIGS. 41A-41D depict the protocol used to follow peptide dissolution and to assess effects of particular anions and/or cations, and/or their concentration, on certain RADA16 (SEQ ID NO:1) compositions. As shown, peptide powder in a vial was dissolved in deionized water with vortexing and sonication. The particular peptide composition utilized in this Example was a 1% composition of RADA16 (SEQ ID NO:1) that was mixed at a 1:1 ratio with a 2× salt solution to obtain a final concentration of 0.5% RADA16 (SEQ ID NO:1) and the desired molar concentration of salt.

Salt Concentration Study

The protocol depicted in FIGS. 41A-41D was followed to prepare 0.5% solutions of RADA16 (SEQ ID NO:1) with different concentrations of $CaCl_2$. Mixed solutions were allowed to sit for a relaxation period of about 24 hours. Vials were then inverted upside down so that gel properties could be assessed. If the composition remained entirely in place when the vial containing it was inverted, the composition was considered a fully functional gel. If more than half of the composition remained in place when the vial containing it was inverted, it was considered a semi-functional gel. If more than half of the composition, and particularly if substantially all of the composition fell to the opposite end of the vial containing it upon inversion, it was considered a non-functional gel.

FIGS. 42A-42G show images of results achieved, specifically depicting upright and inverted vials for each of a variety of concentrations of $CaCl_2$. As can be seen, for these 0.5% RADA16 (SEQ ID NO:1) compositions, fully functional gel was formed with 0.250 M $CaCl_2$ (Panel E), semi-functional gel was formed with 0.500 M $CaCl_2$ (Panel F), and a non-functional gel was formed at 1M $CaCl_2$ (Panel G).

Cation Selection Study

Figure 43:
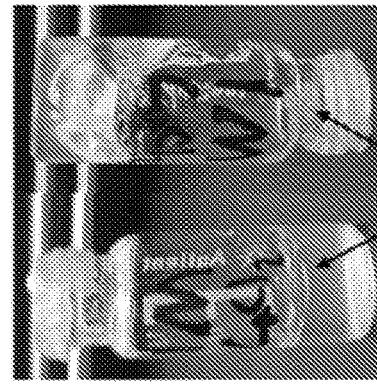
FIG. 43 shows storage modulus measurements of 0.5% RADA16 (SEQ ID NO:1) mixed with NaCl, KCl, and CaCl2 at concentrations of 0.125, 0.250, and 0.500 M.
Figure 42E:
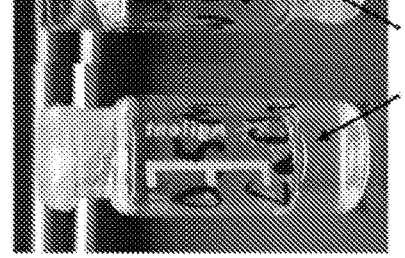
Figure 42D:
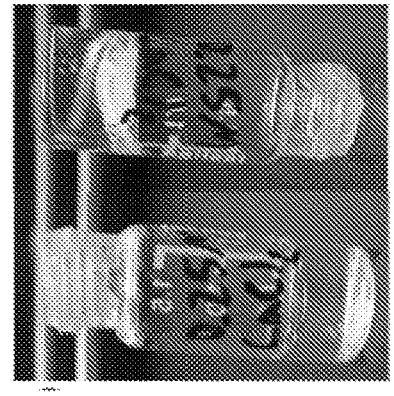
Figure 43:
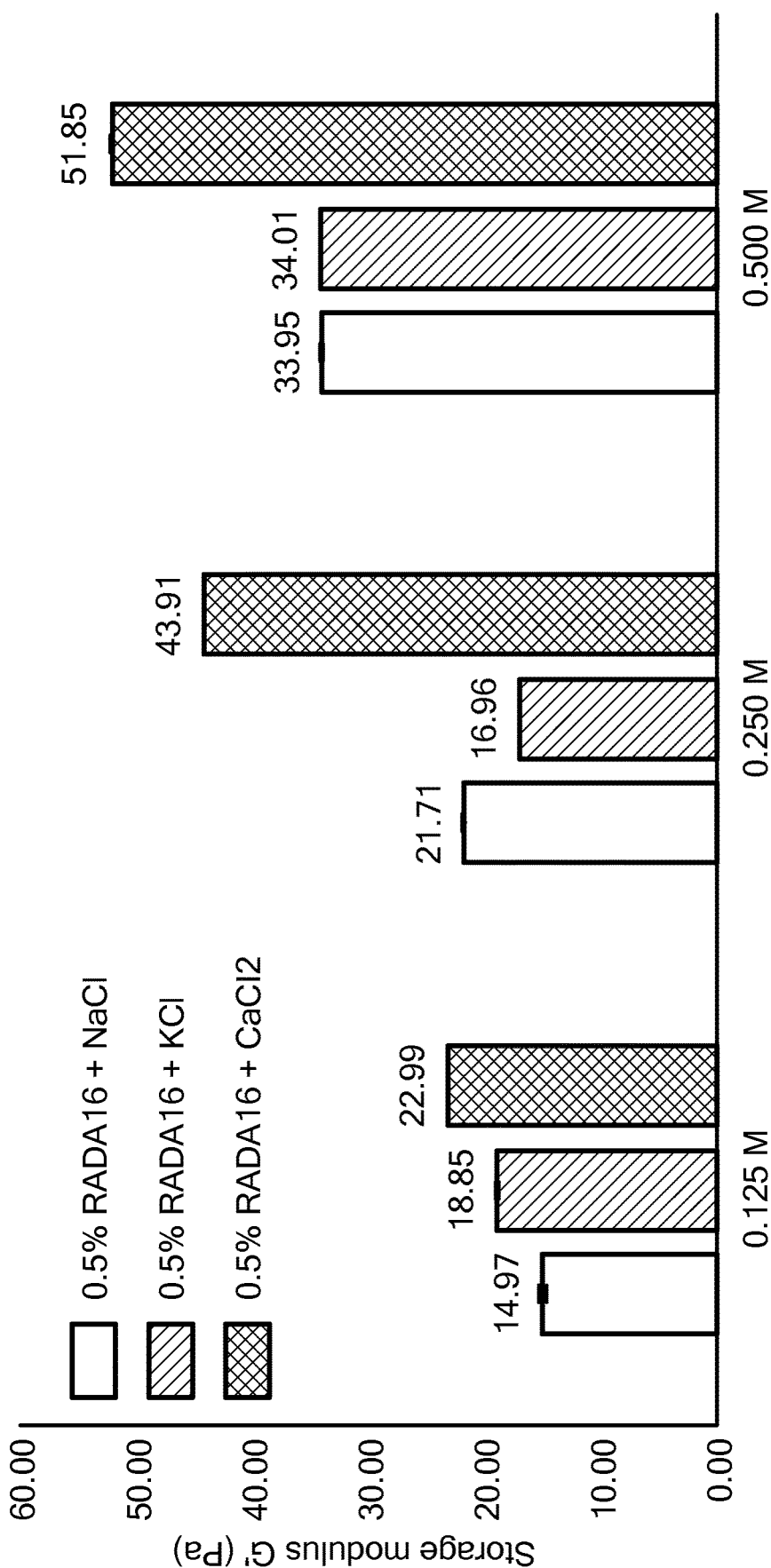

The protocol depicted in FIGS. 41A-41D was followed to prepare 0.5% solutions of RADA16 (SEQ ID NO:1) with 0.005, 0.05, 0.125, 0.25, 0.5, and 1 M NaCl, KCl, and $CaCl_2$ were prepared. The anion, chloride ($Cl^-$), was kept the same to observe the effect of the cations, sodium ($Na^+$), potassium ($K^+$), and calcium ($Ca^{2+}$). Results are depicted in FIG. 43, which provides a basic understanding of how varying the cations of a salt solution affects viscoelastic properties and the stiffness of the resulting compositions.

Mechanical Strength Study

Figure 44:
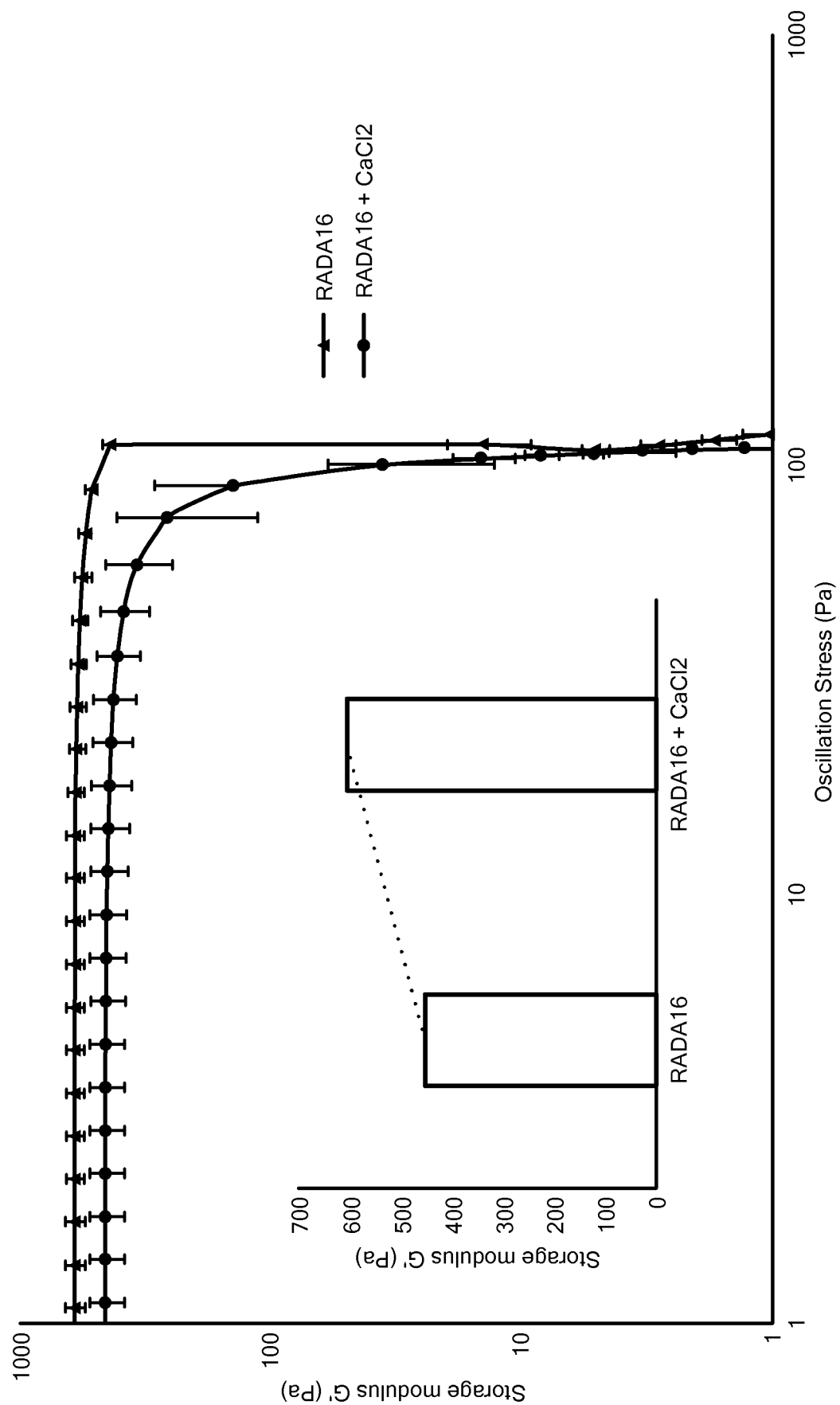
FIG. 44 shows storage modulus measurements of 2.5% RADA16 (SEQ ID NO:1) and 2.5% RADA16 (SEQ ID NO:1) with 0.125 M CaCl2.

The protocol depicted in FIGS. 41A-41D was followed to analyze stiffness of peptide compositions containing either 2.5% RADA16 (SEQ ID NO:1) and no added salt or 2.5% RADA16 (SEQ ID NO:1) and 0.125 M $CaCl_2$. Results are shown in FIG. 44, which provides a basic understanding of the viscoelastic properties of the resulting compositions. As can be seen, there is noticeable increase in stiffness between the two solutions when a cation solution is mixed in.

Reversibility Study

Figure 45A:
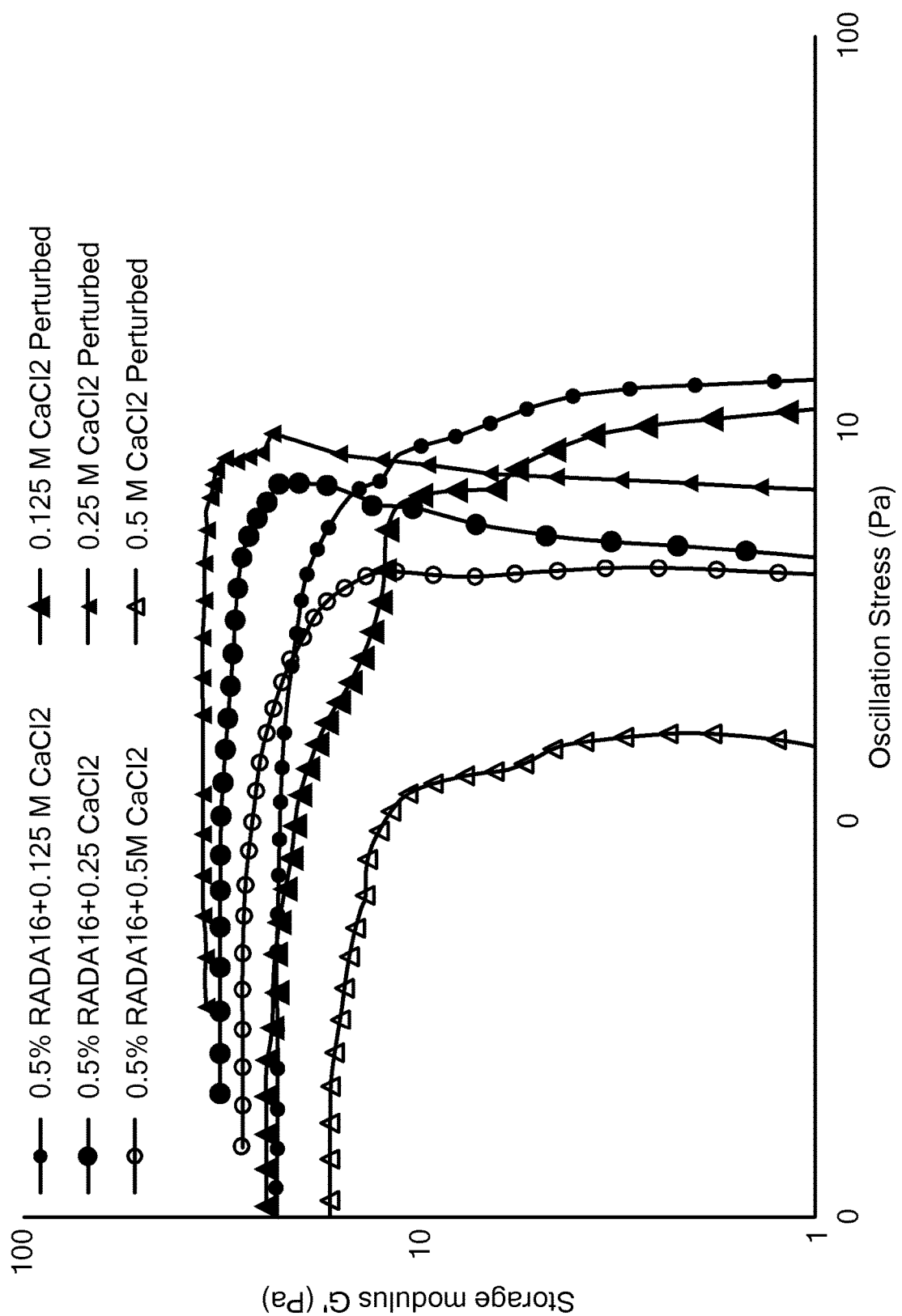
FIGS. 45A and 45B show shows storage modulus measurements of RADA16 (SEQ ID NO:1) with 0.125, 0.250, and 0.500 M after mechanical perturbation. The * denotes that the control sample and the perturbed sample are significantly different.
Figure 45B:
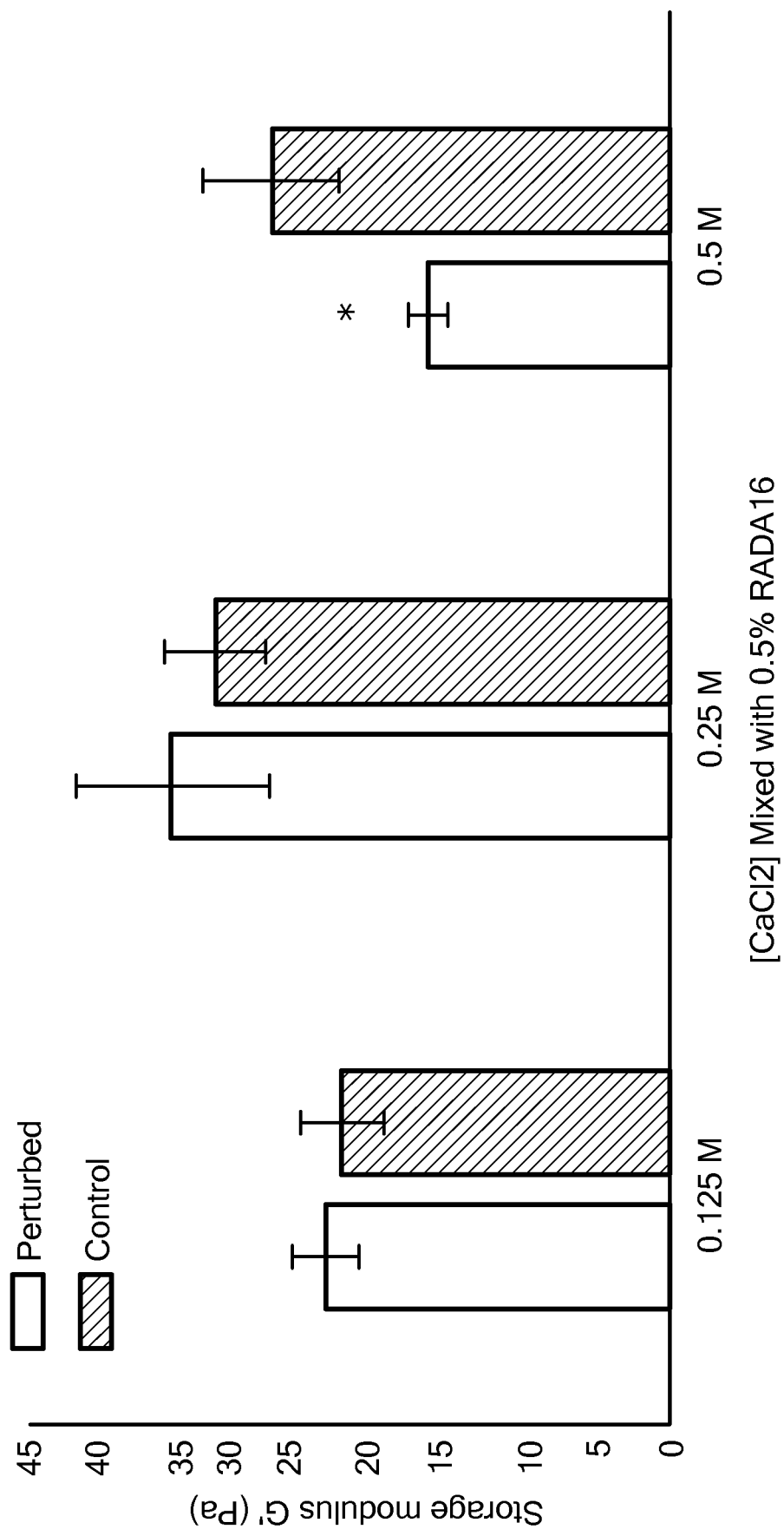
Figure 46:
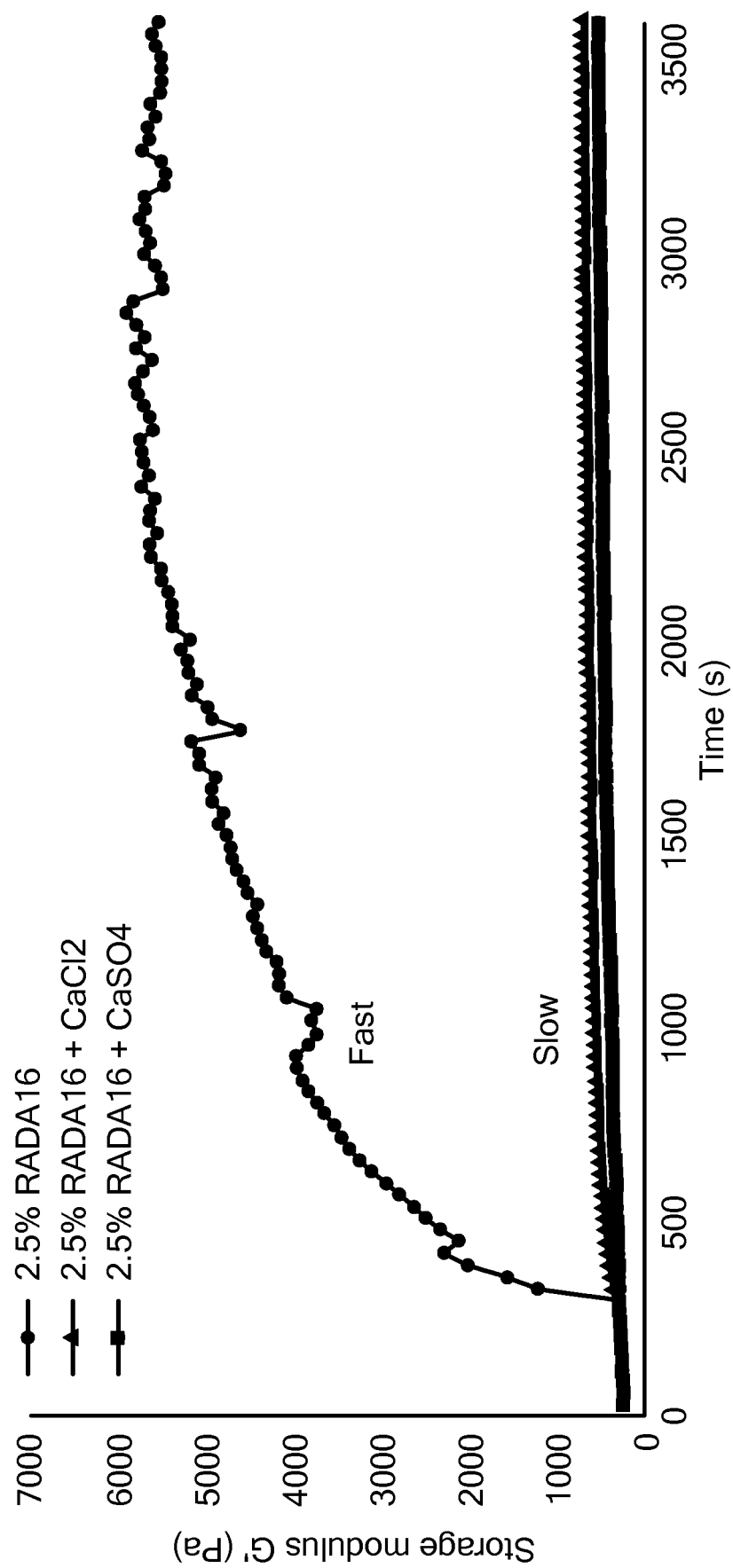
FIG. 46 is storage modulus measures of 2.5% RADA16 (SEQ ID NO:1) treated with $CaCl_2$ and $CaSO_4$ as a function of time.
Figure 47A:
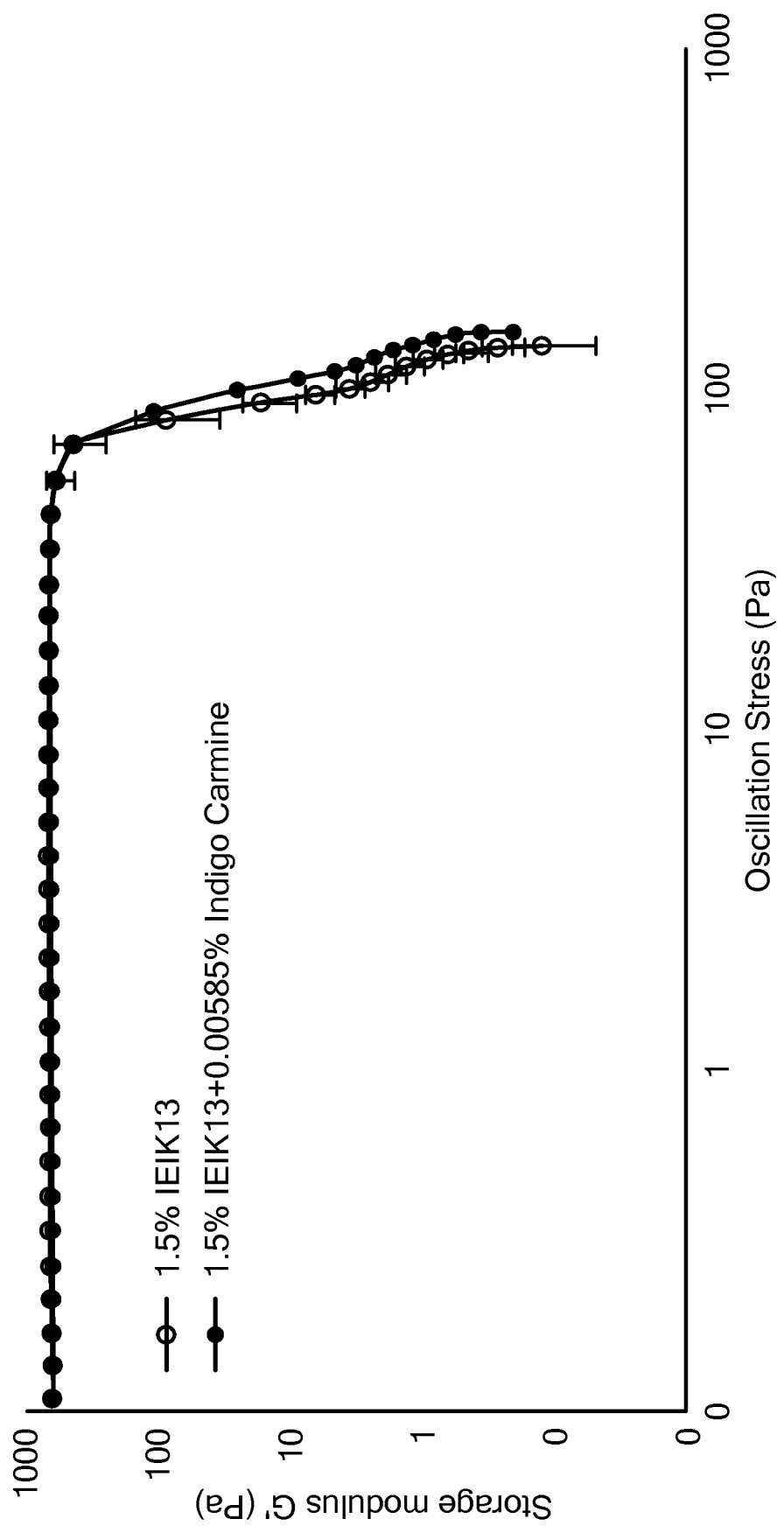
FIG. 47A is exemplary rheological data of IEIK13 (SEQ ID NO:3) and IEIK13 (SEQ ID NO:3) with Indigo Carmine.
Figure 47B:
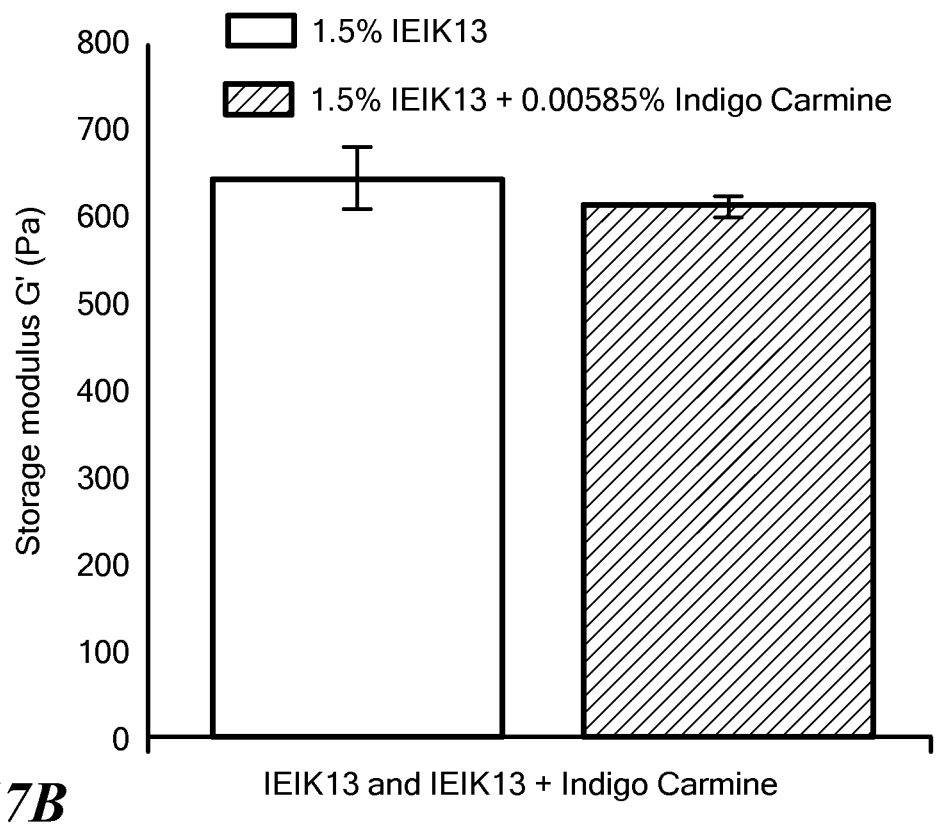
FIG. 47B shows stiffness of IEIK13 (SEQ ID NO:3) and IEIK13 (SEQ ID NO:3) with Indigo Carmine.
Figure 47C:
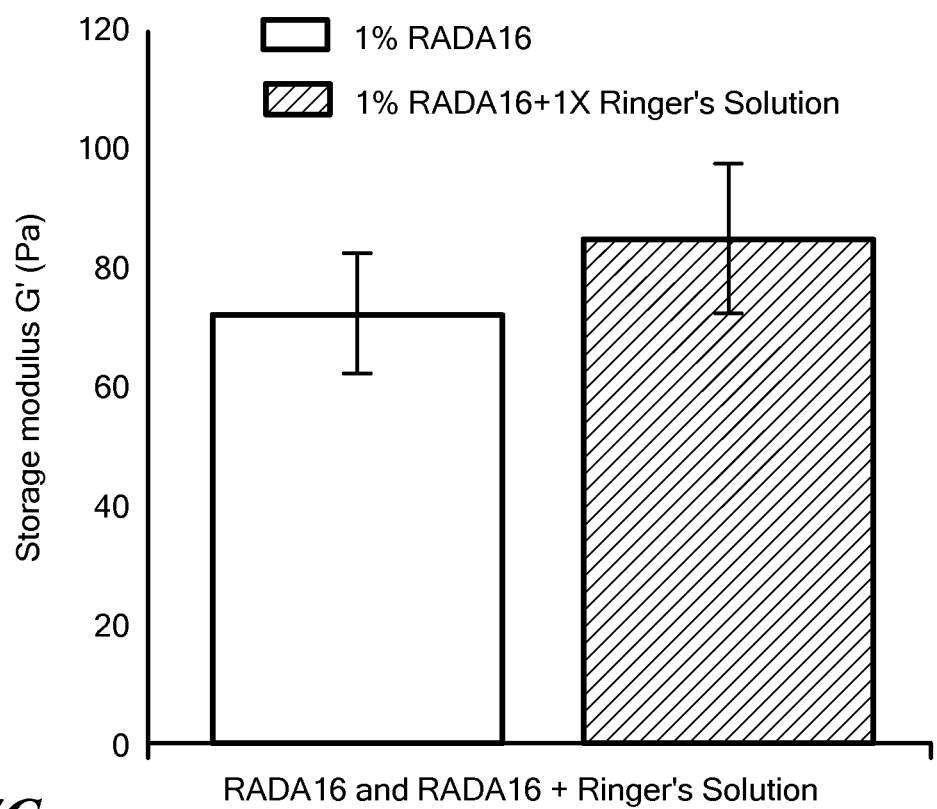
FIG. 47C shows stiffness of RADA16 (SEQ ID NO:1) and RADA16 (SEQ ID NO:1) with Ringer's Solution.
Figure 48:
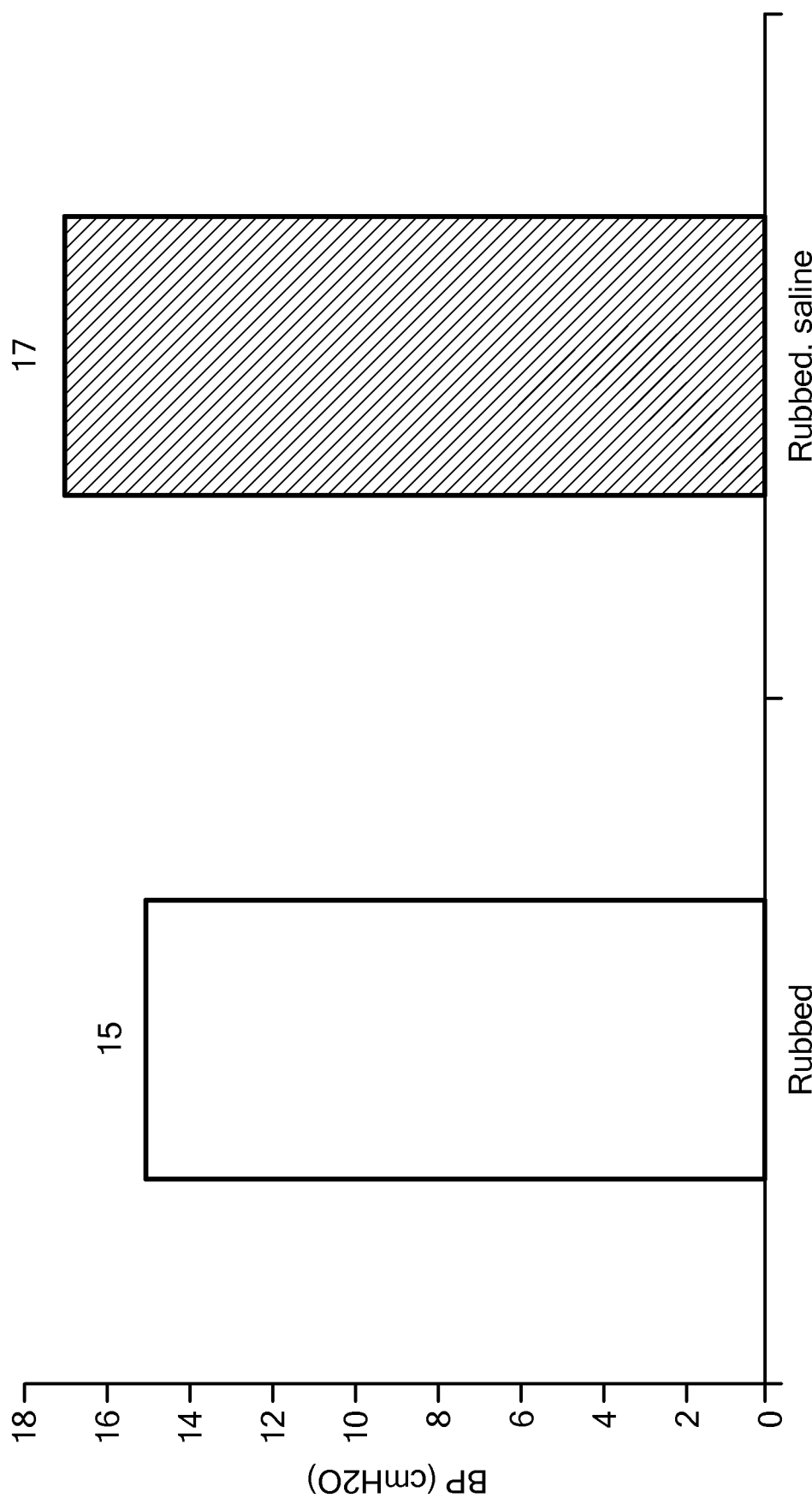
FIG. 48 is a graph of 2.5% RADA16 (SEQ ID NO:1) and 2.5% RADA16 (SEQ ID NO:1) with NaCl, showing an increase in burst pressure of a lung.

The protocol depicted in FIGS. 41A-41D was followed to prepare solutions of 0.5% RADA16 mixed with 0.125, 0.25, or 0.5 M $CaCl_2$ were prepared. The compositions were subjected to mechanical stress through vortexing and sonication, so that their structure was thoroughly disrupted (e.g., randomized). Disrupted compositions were then placed at room temperature for 48 hours to allow self-assembly to take place. FIGS. 45A and 45B present results from this study, and reveal basic viscoelastic properties of the peptide compositions, showing that that reversibility can be maintained even after perturbation of any structure in the composition when 0.125 or 0.25 M $CaCl_2$ is included. By contrast, a composition with 0.5 M $CaCl_2$ shows dramatically less stiffness (reflecting dramatically reduced ability to restore structure) after disruption.

REFERENCES

[1] P. Chen. (2005). "Self-assembly of ionic-complementary peptides: a physicochemical viewpoint." *Colloids and Surfaces.*

[2] Mishra A., et al. (2013). "Influence of metal salts on the hydrogelation properties of ultrashort aliphatic peptides." *RSC Advances.*

[3] Shuguang, Z., et al. (1999). "Peptide self-assembly in functional polymer science and Engineering." *Reactive and Functional Polymers.*

[4] Yanlian, Y., et al. (2009). "Designer self-assembling peptide nanomaterials." *Nano Today.*

[5] Zhaoyang, Y., et al. (2008). "Temperature and pH effects on biophysical and morphological properties of self-assembling peptide RADA16-I." *Journal of Peptide Science.*

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims.

We claim:

1. An IEIK13 composition comprising:
an IEIK13 peptide comprising an amino acid sequence as set forth in SEQ ID NO:3 at a concentration of at least 0.25% weight to volume;
which composition has a pH within the range of 2.5 to 4.0 and an ionic strength within the range of 0 to 0.03 M.

2. The composition of claim 1, wherein the ionic strength is adjusted/given by common salts, wherein the common salts are selected from the group consisting of NaCl, KCl, $MgCl_2$, $CaCl_2$, and $CaSO_4$.

3. The composition of claim 1, wherein the composition has storage modulus within the range of 100 to 10000 Pa at 1 rad/sec of frequency and 1 Pa of oscillation stress.

4. The composition of claim 1, wherein the composition further comprises a solution comprising sodium hydroxide, potassium hydroxide, calcium hydroxide, sodium carbonate, sodium acetate, sodium sulfide, or Dulbecco's modified Eagle's medium (DMEM).

5. The composition of claim 1, wherein:
the IEIK13 peptide is present at a concentration of less than 3% and/or
the composition has a pH within the range of 2.7 to 3.7.

6. The composition of claim 5, which composition exhibits a storage modulus of more than 500 Pa at 1 rad/sec of frequency and 1 Pa of oscillation stress.

7. The composition of claim 1, wherein the composition is buffered with a sodium hydroxide, potassium hydroxide, calcium hydroxide, sodium carbonate, sodium acetate, or sodium sulfide, so that the pH of the composition is regulated.

8. A liquid peptide composition comprising:
a peptide having a length within the range of 6 to 20 amino acids and an amino acid sequence of alternating hydrophobic amino acid and hydrophilic amino acids, which composition is at a pH within a range of 2.5 to 4.0 and is characterized in that:
the liquid peptide composition has a viscosity within the range of 1 Pa·s to 500,000 Pa·s at room temperature;
the liquid peptide composition has a storage modulus at 1 rad/sec of frequency and 1 Pa of oscillation stress within the range of 1 to 5000 Pa; and
within a time period 0 to 30 s, the liquid peptide composition forms chemical or physical crosslinked networks
wherein the peptide comprises IEIK13 comprising an amino acid sequence as set forth in SEQ ID NO:3, and the liquid peptide composition has an ionic strength within the range of 0 to 0.03 M.

9. The composition of claim 8, wherein the composition comprises one or more common salts, wherein the common salts are selected from the group consisting of NaCl, KCl, $MgCl_2$, $CaCl_2$, and $CaSO_4$, and has an ionic strength within the range of 0.0001 M to 0.03 M.

10. The composition of claim 8, wherein the composition comprises one or more common salts, wherein the common salts are composed of one or more salt forming cations and one or more salt forming anions, wherein the salt forming cations are selected from the group consisting of ammonium, calcium, iron, magnesium, potassium, pyridinium, quaternary ammonium, and sodium, wherein the salt forming anions are selected from the group consisting of acetate, carbonate, chloride, citrate, cyanide, floored, nitrate, nitrite, and phosphate.

11. The composition of claim 8, wherein the composition is buffered with a sodium hydroxide, potassium hydroxide, calcium hydroxide, sodium carbonate, sodium acetate, or sodium sulfide, so that the pH of the composition is regulated.

12. The composition of claim 8, which is an aqueous composition.

13. The composition of claim 1, wherein the salt forming cations are selected from the group consisting of ammonium, calcium, iron, magnesium, potassium, pyridinium, quaternary ammonium, and sodium.

14. The composition of claim 1, wherein the salt forming anions are selected from the group consisting of acetate, carbonate, chloride, citrate, cyanide, fluoride, nitrate, nitrite, and phosphate.

* * * * *

SEQUENCE LISTING

<160> NUMBER OF SEQ ID NOS: 6

<210> SEQ ID NO 1
<211> LENGTH: 16
<212> TYPE: PRT
<213> ORGANISM: Artificial Sequence
<220> FEATURE:
<223> OTHER INFORMATION: synthetic

<400> SEQUENCE: 1

Arg Ala Asp Ala Arg Ala Asp Ala Arg Ala Asp Ala Arg Ala Asp Ala
1               5                   10                  15

<210> SEQ ID NO 2
<211> LENGTH: 12
<212> TYPE: PRT
<213> ORGANISM: Artificial Sequence
<220> FEATURE:
<223> OTHER INFORMATION: synthetic

<400> SEQUENCE: 2

Lys Leu Asp Leu Lys Leu Asp Leu Lys Leu Asp Leu
1               5                   10

<210> SEQ ID NO 3
<211> LENGTH: 13
<212> TYPE: PRT
<213> ORGANISM: Artificial Sequence
<220> FEATURE:
<223> OTHER INFORMATION: synthetic

<400> SEQUENCE: 3

Ile Glu Ile Lys Ile Glu Ile Lys Ile Glu Ile Lys Ile
1               5                   10

<210> SEQ ID NO 4
<211> LENGTH: 4
<212> TYPE: PRT
<213> ORGANISM: Artificial Sequence
<220> FEATURE:
<223> OTHER INFORMATION: synthetic

<400> SEQUENCE: 4

Arg Ala Asp Ala
1

<210> SEQ ID NO 5
<211> LENGTH: 4
<212> TYPE: PRT
<213> ORGANISM: Artificial Sequence
<220> FEATURE:
<223> OTHER INFORMATION: synthetic

<400> SEQUENCE: 5

Lys Leu Asp Leu
1

<210> SEQ ID NO 6
<211> LENGTH: 4
<212> TYPE: PRT
<213> ORGANISM: Artificial Sequence
<220> FEATURE:
<223> OTHER INFORMATION: synthetic

<400> SEQUENCE: 6

Ile Glu Ile Lys
1